US006701774B2

(12) United States Patent
Srinivasan et al.

(10) Patent No.: US 6,701,774 B2
(45) Date of Patent: Mar. 9, 2004

(54) PARALLEL GAS CHROMATOGRAPH WITH MICRODETECTOR ARRAY

(75) Inventors: Ravi Srinivasan, Mountain View, CA (US); Daniel Meron Pinkas, Kensington, CA (US); Shenheng Guan, Palo Alto, CA (US); Michael Myslovaty, San Jose, CA (US); Michael Spitkovsky, Sunnyvale, CA (US); James R. Engstrom, Ithaca, NY (US); H. Sam Bergh, San Francisco, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/801,430

(22) Filed: Mar. 7, 2001

(65) Prior Publication Data

US 2002/0014106 A1 Feb. 7, 2002

Related U.S. Application Data

(60) Provisional application No. 60/222,540, filed on Aug. 2, 2000.

(51) Int. Cl.[7] ........................ G01N 30/04; B01D 53/02; B01D 15/08; C02F 1/28
(52) U.S. Cl. ................... 73/23.42; 210/198.2; 210/656; 96/102
(58) Field of Search ............................ 73/23.42, 61.52; 210/198.2, 656; 436/100, 149, 518; 96/102, 103, 106

(56) References Cited

U.S. PATENT DOCUMENTS

| 3,373,872 A | 3/1968 | Hrdina |
| 4,424,127 A | 1/1984 | Roeraade ................. 210/198.2 |

(List continued on next page.)

FOREIGN PATENT DOCUMENTS

| DE | 41 36 413 A1 | 11/1991 | .......... G01N/27/62 |
| EP | 0 719 411 B1 | 3/1999 | .......... G01N/33/00 |

(List continued on next page.)

OTHER PUBLICATIONS

Angell, J.B. et al., "Silicon Micomechanical Devices", *Sci. Am.*, Apr. 1983, 36, pp. 44–55.
Ehrfeld et al., "Microreactors: New Technology for Modern Chemistry", *Wiley VCH*, 2000.
Ehrfeld et al., "Implementation of Microreaction Technology in Process Engineering", pp. 14–34.
Emmer et al., "Fabrication and Characterization of a Silicon Microvalve", *J. Microcol.* Sep., 1992, 4, pp. 13–15.
Schiewe et al., "Polymer Membranes for Product Enrichment in Microreaction Technology", pp. 550–555.
Siemens, Flexible Tools for Maximum Capability, Feb. 21, 2001.

*Primary Examiner*—Hezron Williams
*Assistant Examiner*—Jay L Politzer
(74) *Attorney, Agent, or Firm*—Senniger, Powers, Leavitt & Roedel

(57) ABSTRACT

Gas chromatographs of the invention generally comprise four or more analysis channels. Specifically, four or more gas chromatography columns are configured for parallel analysis of four or more gaseous samples with detection being effected using a microdetector array comprising four or more microdetectors. In one embodiment, the four or more microdetectors 510 are microfabricated detectors, and are integrally formed with a substrate or with one or more microchip bodies mounted on a substrate. In a preferred embodiment, a microdetector array comprises four or more thermal conductivity detectors having one or more thin-film detection filaments. A preferred heated environment for highly parallel gas chromatographs is also disclosed.

51 Claims, 43 Drawing Sheets

U.S. PATENT DOCUMENTS

| | | | |
|---|---|---|---|
| 4,580,439 A | 4/1986 | Manaka | 73/23 |
| 4,584,867 A | 4/1986 | Forster | 73/23 |
| 4,594,879 A | 6/1986 | Maeda et al. | 73/27 R |
| 4,735,082 A | 4/1988 | Kolloff | 73/27 |
| 4,806,314 A | 2/1989 | Fertig et al. | 422/78 |
| 4,893,108 A | 1/1990 | Kolesar, Jr. | 338/34 |
| 4,985,356 A | 1/1991 | Sawai et al. | 435/69.4 |
| 4,988,870 A | 1/1991 | Diehl | 250/288 |
| 5,027,499 A | 7/1991 | Prohaska | 29/595 |
| 5,049,509 A | 9/1991 | Szakasits et al. | 436/140 |
| 5,141,534 A | 8/1992 | Sacks et al. | 55/197 |
| 5,165,292 A | 11/1992 | Prohaska | 73/866 |
| 5,205,845 A | 4/1993 | Sacks et al. | 55/197 |
| 5,356,756 A | 10/1994 | Cavicchi et al. | 430/315 |
| 5,356,819 A | 10/1994 | Ritschel | 436/147 |
| 5,376,252 A | 12/1994 | Ekstrom et al. | 204/603 |
| 5,377,527 A | 1/1995 | Kamiunten | 73/25.03 |
| 5,463,899 A | 11/1995 | Zemel et al. | 73/195 |
| 5,535,614 A | 7/1996 | Okamoto et al. | 73/23.31 |
| 5,576,626 A | 11/1996 | Lo | 324/464 |
| 5,772,321 A | 6/1998 | Rhodes | 374/44 |
| 5,801,297 A | 9/1998 | Mifsud et al. | 73/23.34 |
| 5,801,380 A | 9/1998 | Sinha | 250/299 |
| 5,831,146 A | 11/1998 | Newman | 73/23.31 |
| 5,872,010 A | 2/1999 | Karger et al. | 436/173 |
| 5,872,306 A | 2/1999 | Arnold | 73/23.37 |
| 5,895,591 A | 4/1999 | Kojima et al. | 219/209 |
| 5,918,257 A | 6/1999 | Mifsud et al. | 73/23.34 |
| 5,922,106 A | 7/1999 | Mowry et al. | 95/87 |
| 5,959,297 A | 9/1999 | Weinberg et al. | 250/288 |
| 5,985,356 A | 11/1999 | Schultz et al. | 427/8 |
| 6,004,617 A | 12/1999 | Schultz et al. | 427/8 |
| 6,030,917 A | 2/2000 | Weinberg et al. | 502/104 |
| 6,062,065 A | 5/2000 | Sugimoto et al. | 73/23.42 |
| 6,063,633 A | 5/2000 | Willson, III | 436/37 |
| 6,068,684 A | 5/2000 | Overton | 96/104 |
| 6,149,882 A | 11/2000 | Guan et al. | 422/211 |
| 6,197,198 B1 | 3/2001 | Messinger et al. | 210/656 |
| 6,227,034 B1 | 5/2001 | Trochesset | 73/23.42 |
| 6,438,497 B1 | 8/2002 | Mansky et al. | 702/22 |
| 6,455,316 B1 | 9/2002 | Turner et al. | 436/37 |

FOREIGN PATENT DOCUMENTS

| | | | |
|---|---|---|---|
| GB | 1 262 529 | 4/1969 | G01N/31/08 |
| GB | 1262529 | 2/1972 | |
| JP | 62019760 | 1/1997 | B01D/15/08 |
| WO | WO 91/16966 | 11/1991 | B01D/57/02 |
| WO | WO 99/12626 | 3/1999 | B01D/15/08 |
| WO | WO 99/51980 | 10/1999 | G01N/30/02 |
| WO | WO 99/60396 | 11/1999 | G01N/31/10 |
| WO | WO 99/64160 | 12/1999 | B01L/3/02 |
| WO | WO 00/09255 | 2/2000 | B01J/19/00 |
| WO | WO 00/14529 | 3/2000 | G01N/31/02 |
| WO | WO 00/23734 | 4/2000 | F16K/11/02 |
| WO | WO 00/23921 | 4/2000 | G06F/17/50 |
| WO | WO 00/32308 | 6/2000 | B01J/19/00 |
| WO | 00/36410 | 6/2000 | G01N/31/00 |
| WO | WO 00/51720 | 9/2000 | B01J/19/00 |

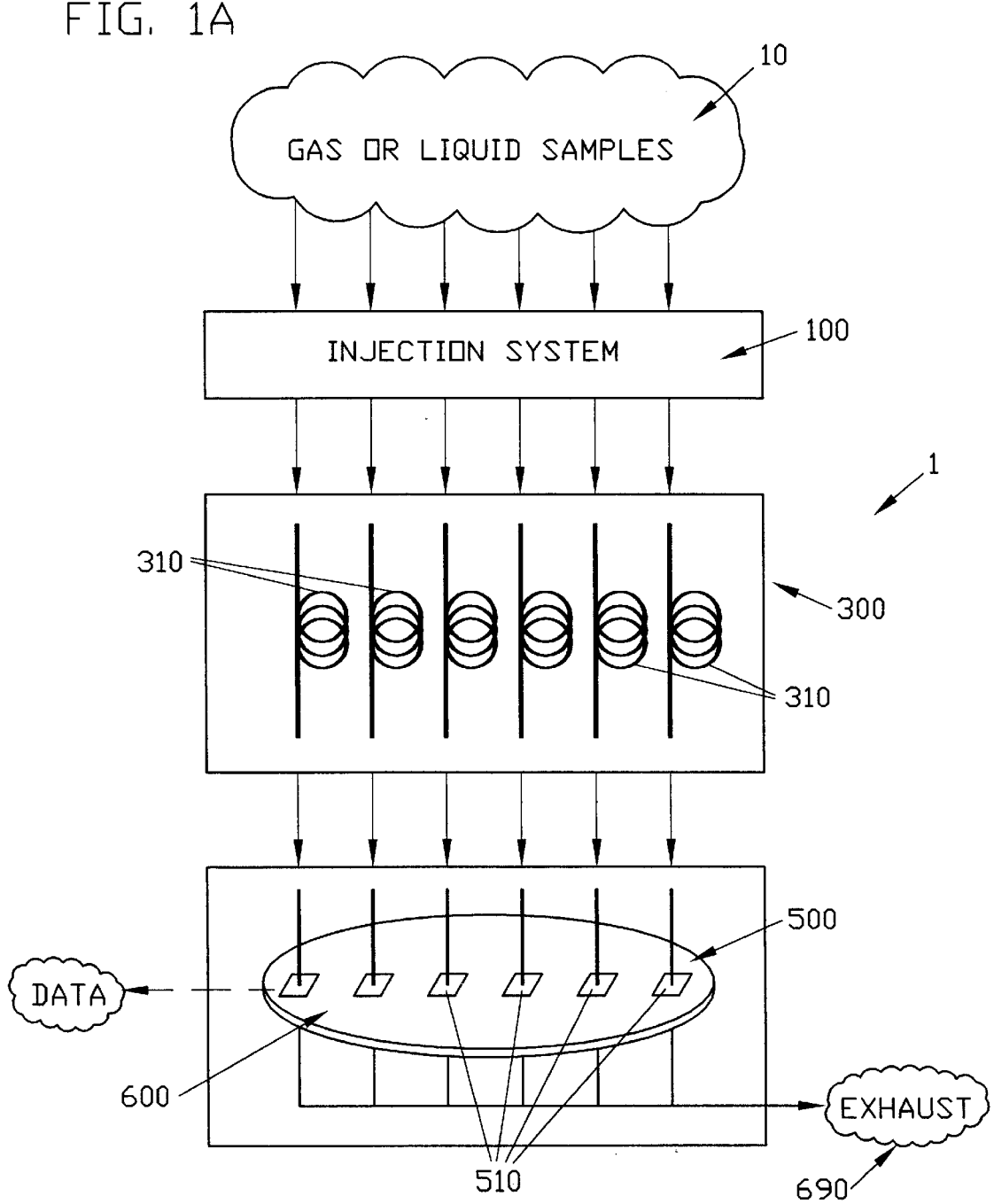

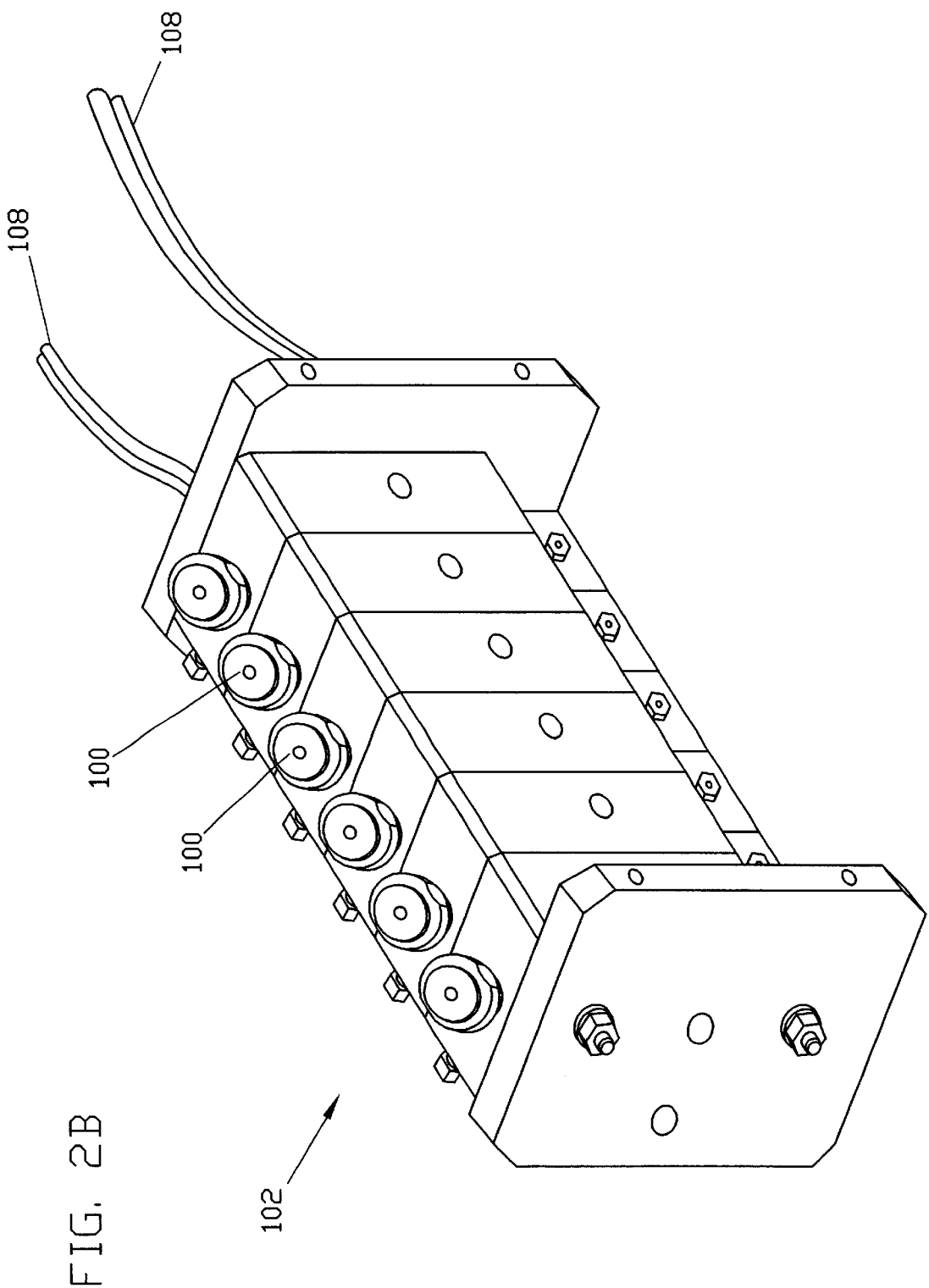

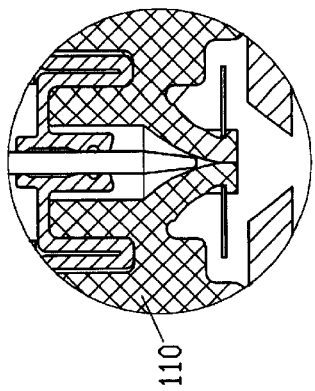
FIG. 2D
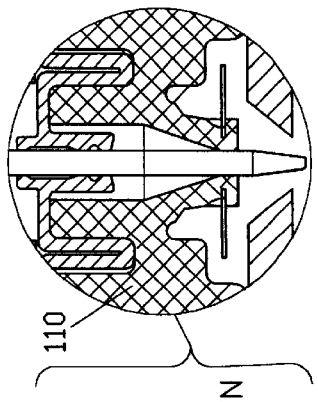
FIG. 2E
FIG. 2C
INJECTION PORT CROSS SECTION
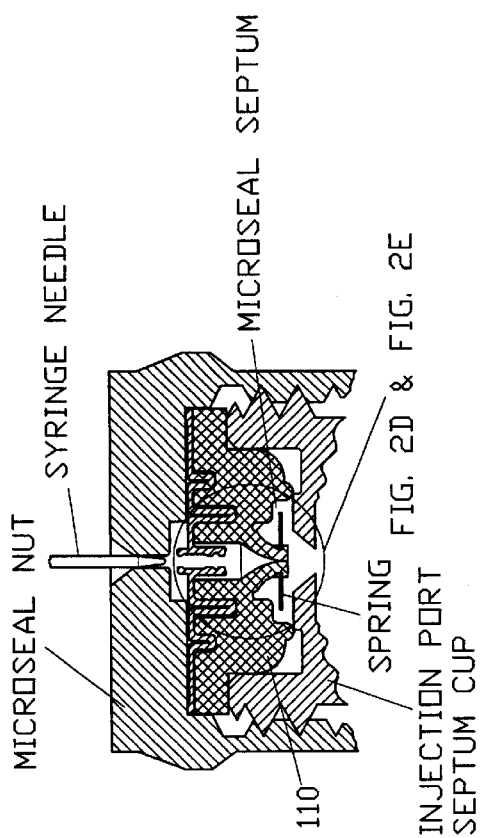
- MICROSEAL NUT
- SYRINGE NEEDLE
- MICROSEAL SEPTUM
- SPRING   FIG. 2D & FIG. 2E
- INJECTION PORT SEPTUM CUP
INJECTION SEQUENCE
1. SLIDING SEAL IS MADE AROUND NEEDLE AS IT IS INSERTED
2. SYRINGE NEEDLE FORCES DUCKBILL LIPS TO OPEN
3. SAMPLE INJECTED
4. SPRING FORCES DUCKBILL CLOSED AS NEEDLE IS WITHDRAWN
5. NEEDLE IS REMOVED FROM SLIDING SEAL

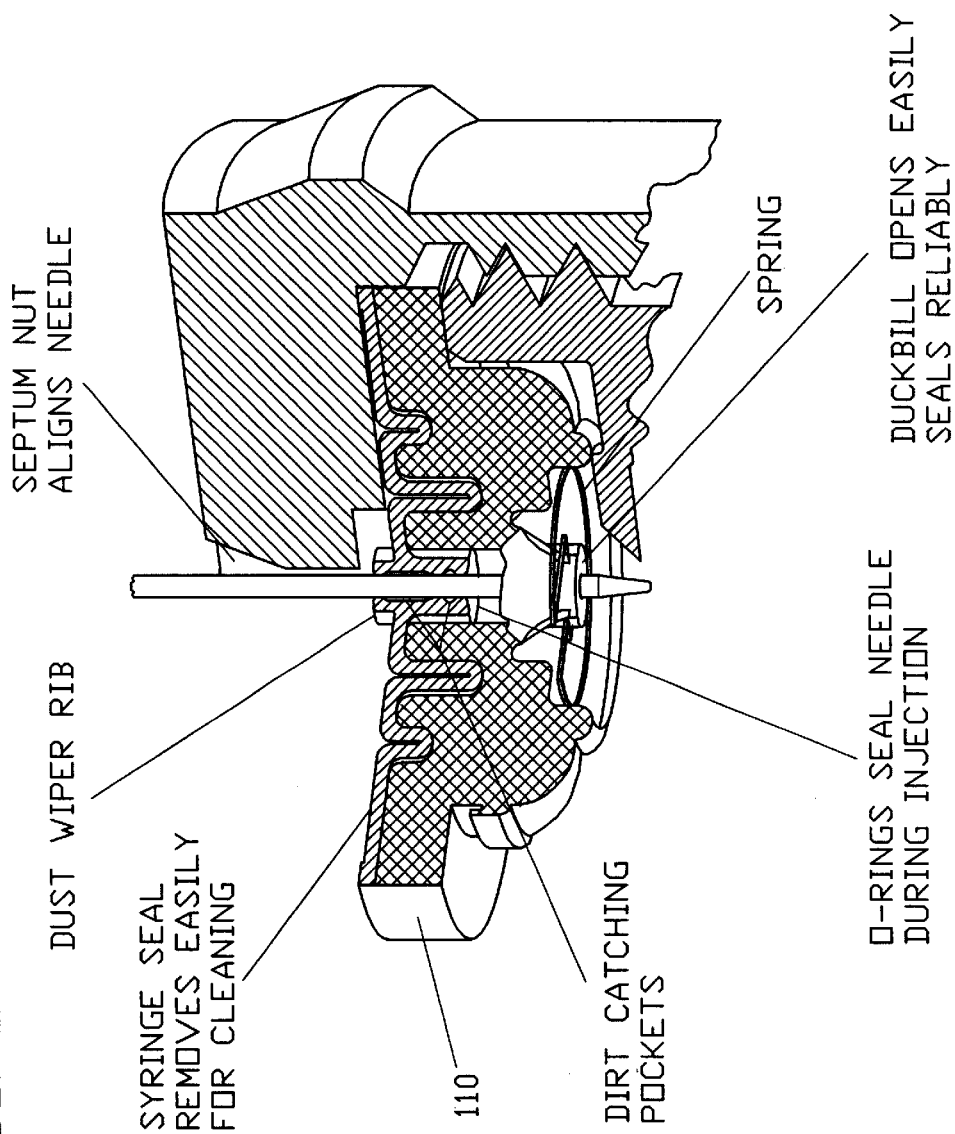

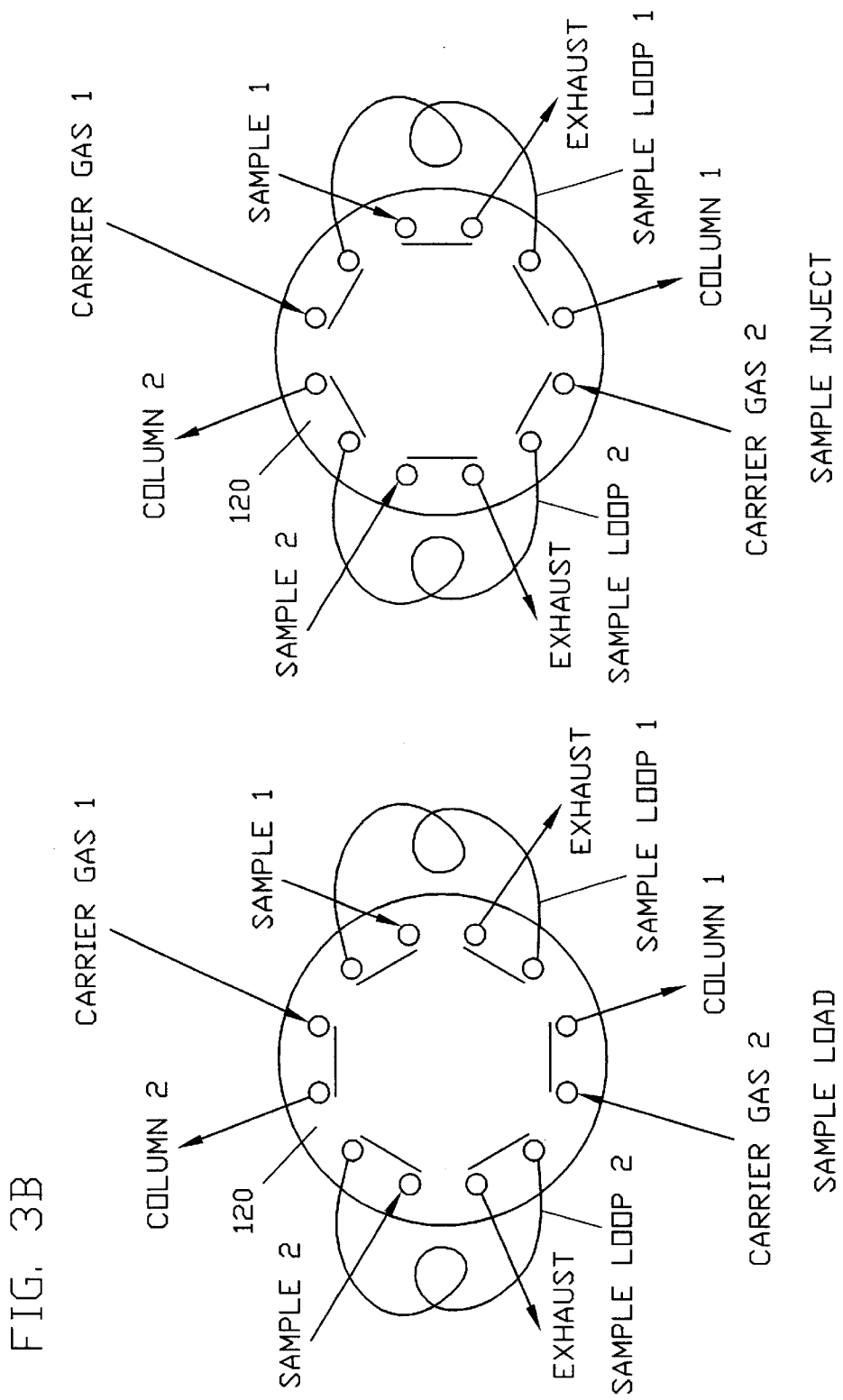

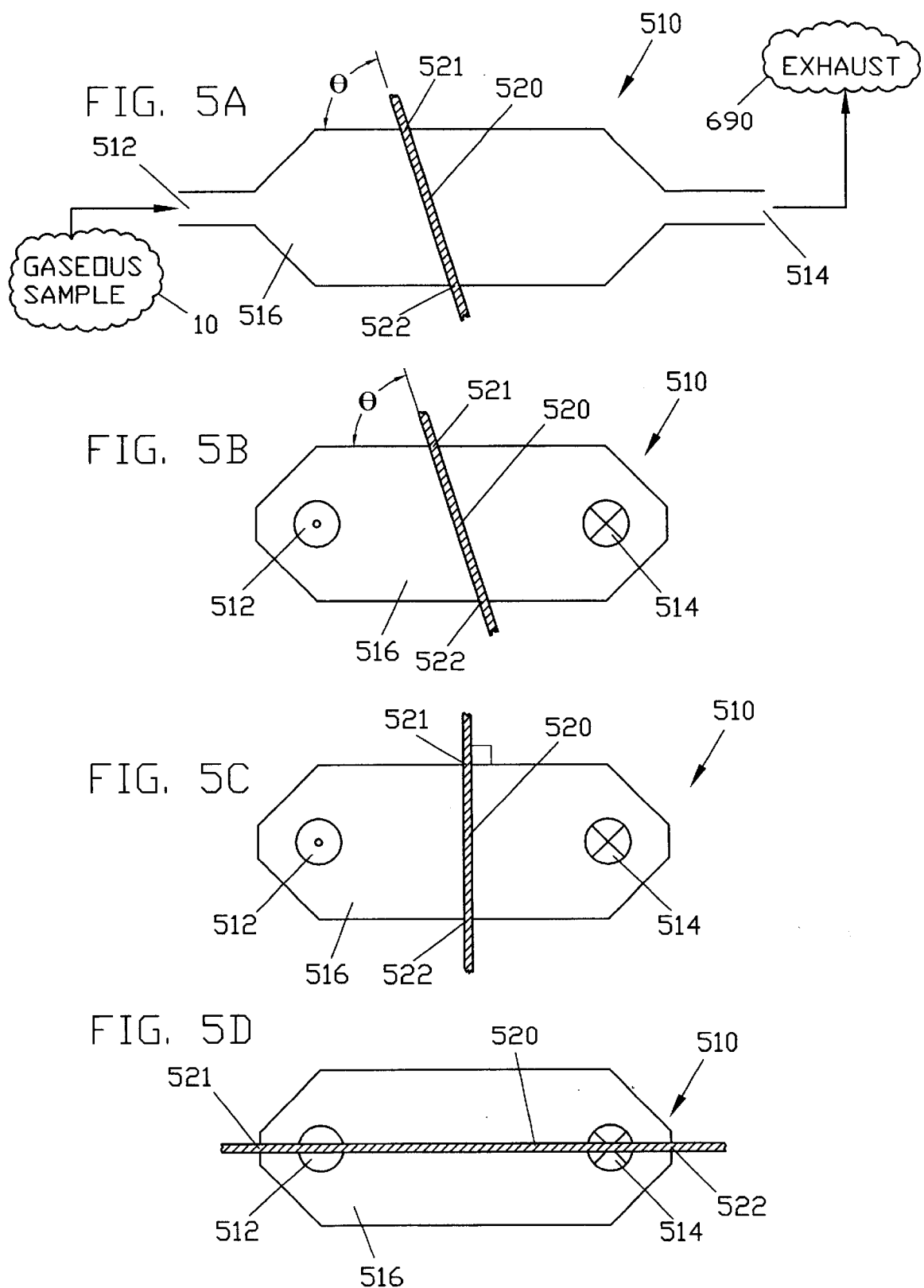

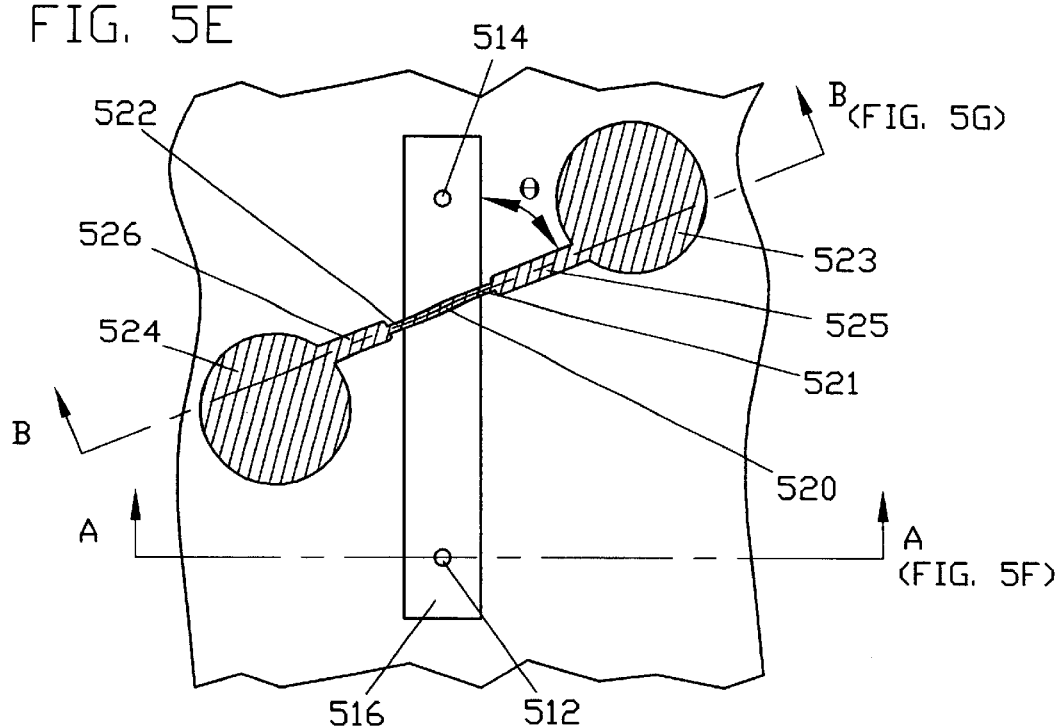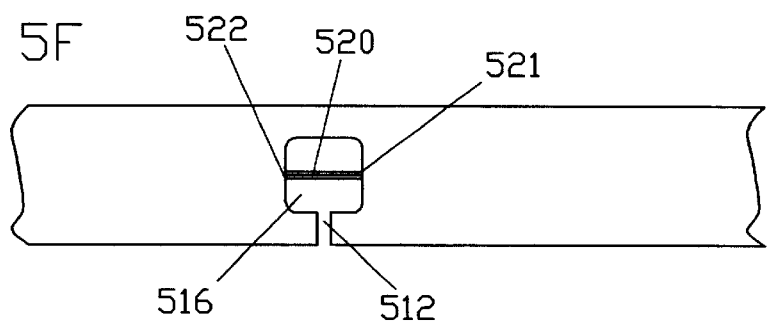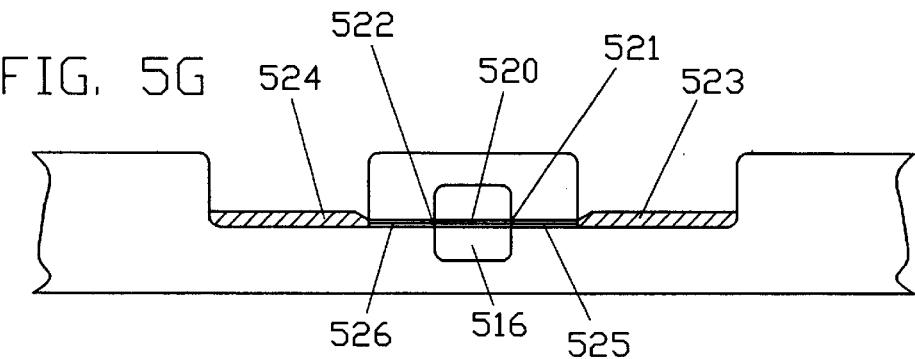

FIG 5H.
FIG. 5I
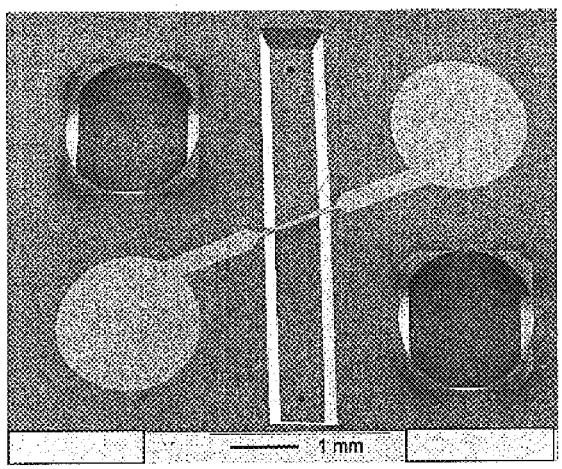
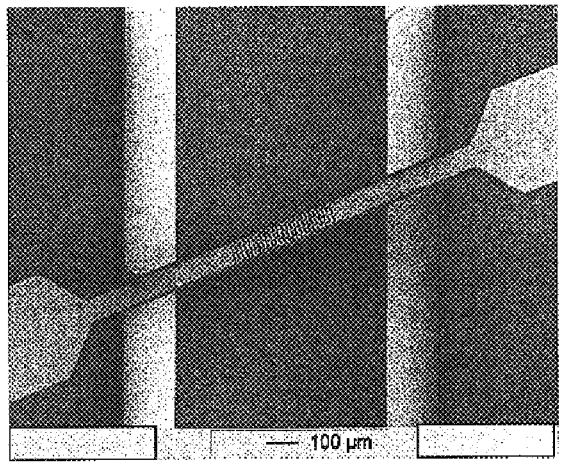

FIG. 5J    HEAT TRANSFER CALCULATIONS FOR TDC DESIGN
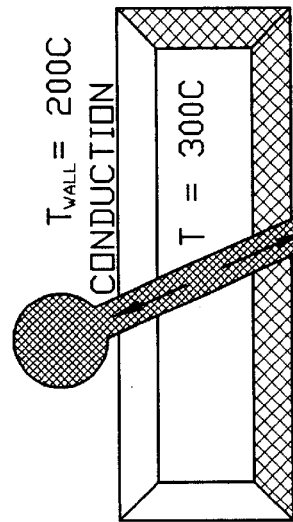
\*CONDUCTION VIA LEADS TO FRAME
$Q_{conduction} = \frac{k}{L} * A * \Delta T$
$Q_{conduction} \sim 0.2 mW$
\*RADIATION
$Q_{radiation} = \varepsilon * \sigma * A * (T_{hot}^4 - T_{ambient}^4)$
$Q_{radiation} = 1 * (5.67 * 10^{-8}) * (52 \mu m * 1.5 mm) * (573^4 - 473^4)$
$Q_{radiation} \approx 0.25 mW$
\*CONVECTION                                \*CONVECTION INTO GAS DOMINATES
$Q_{convection} = h * A * \Delta T$
$Q_{convection} = 1000 * (52 \mu m * 1.5 mm) * 100 = 8 mW$

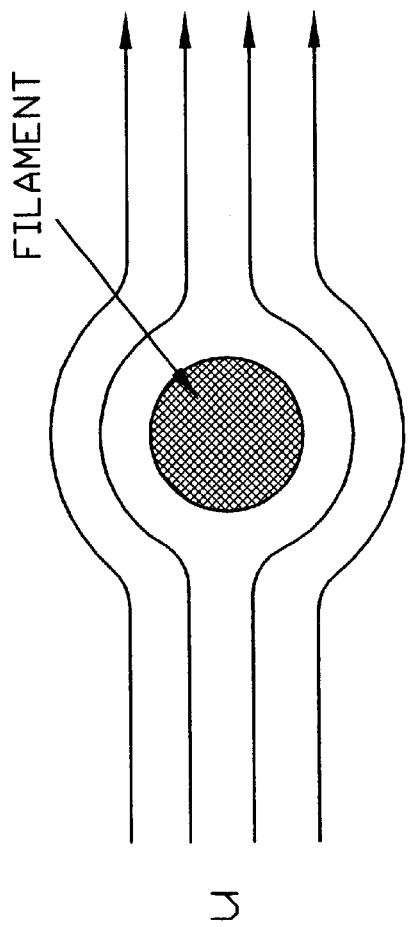
FIG. 5K    CONVECTION HEAT TRANSFER FOR TDC DESIGN
$Q_{convection} = h * A * \Delta T$
$h \approx 2 * \frac{K}{D} + \frac{1}{2} * u * \rho * C_p$
REQUIRE-
$2 * \frac{K}{D} \gg \frac{1}{2} * u * \rho * C_p$    TDC VS. ANEMOMETER BEHAVIOR

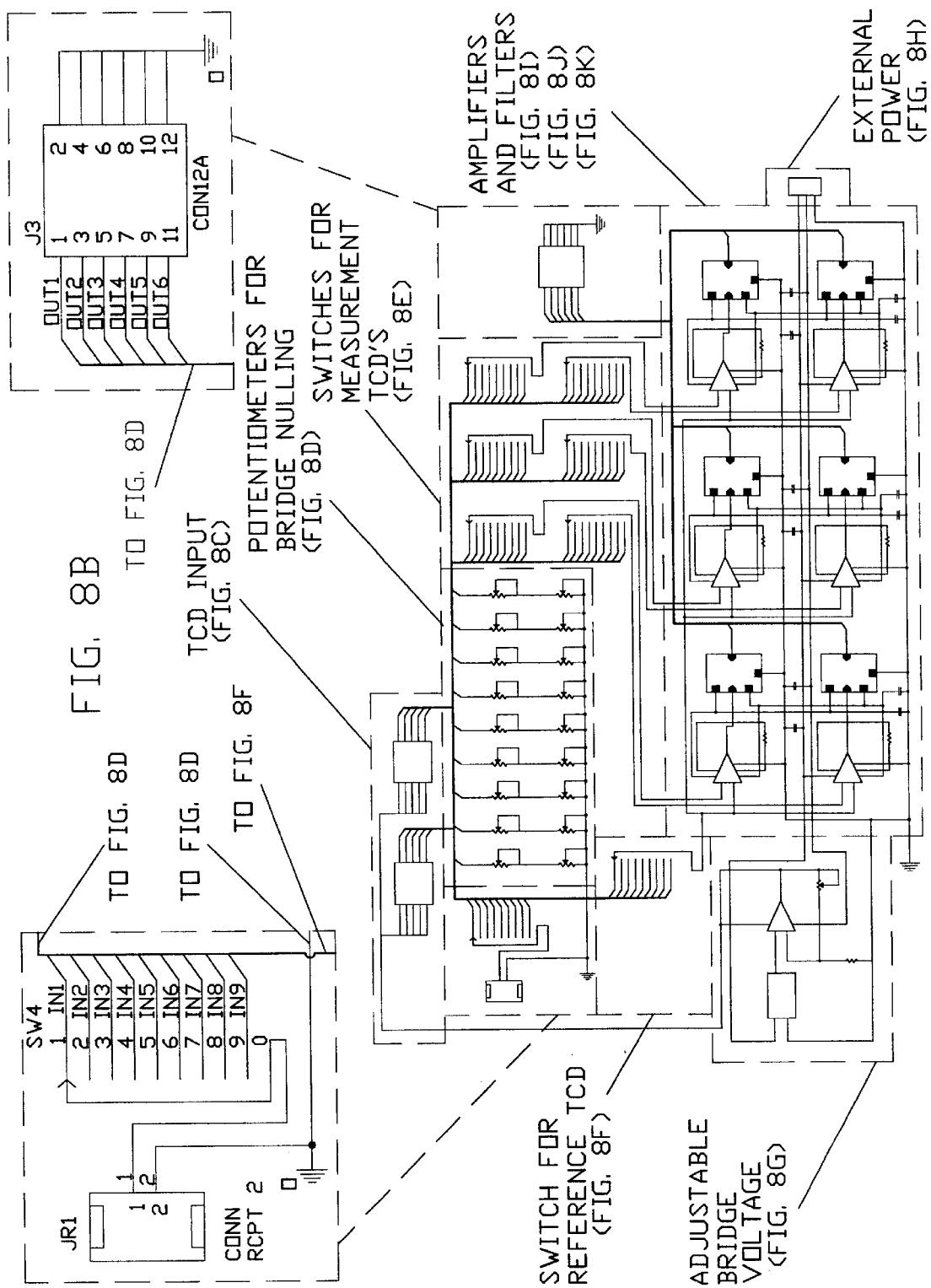

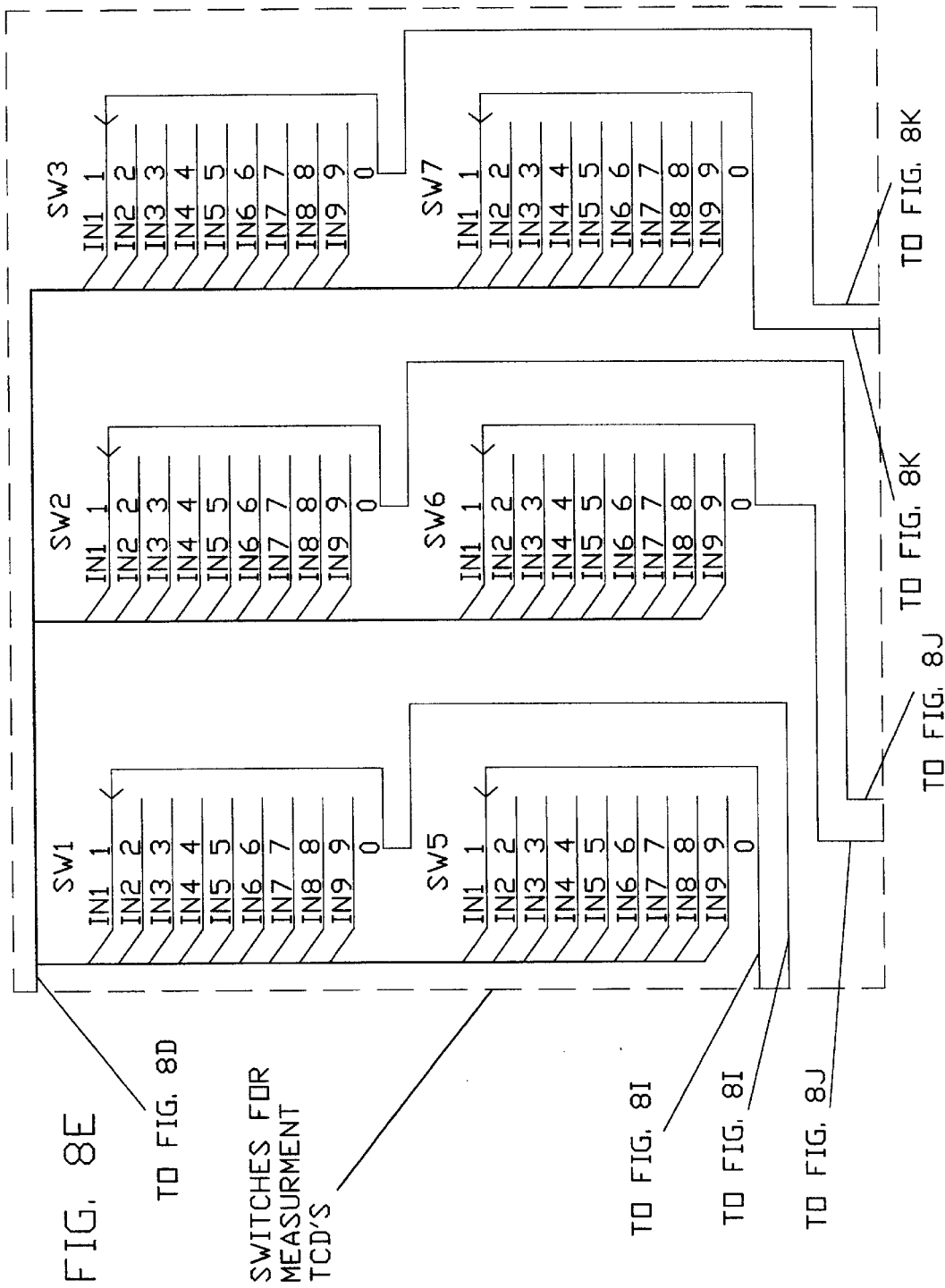

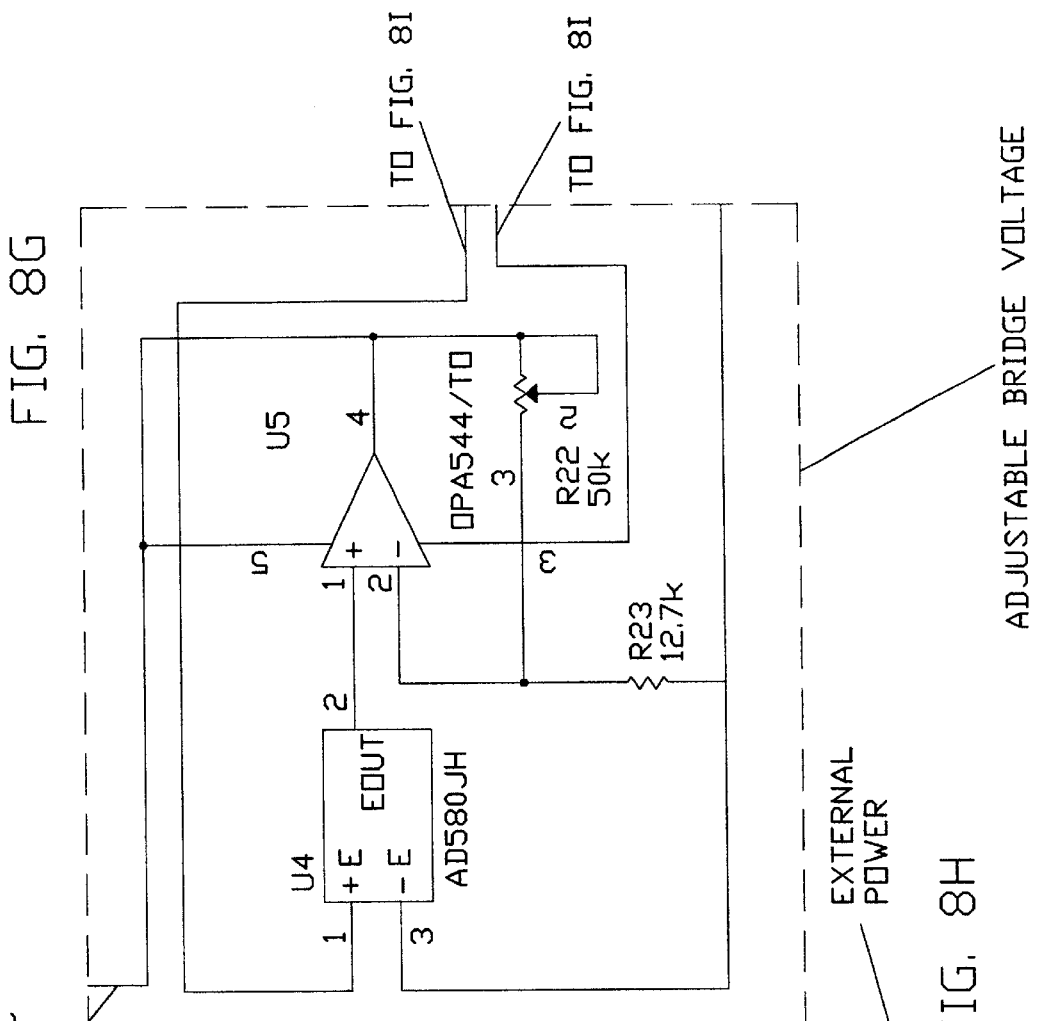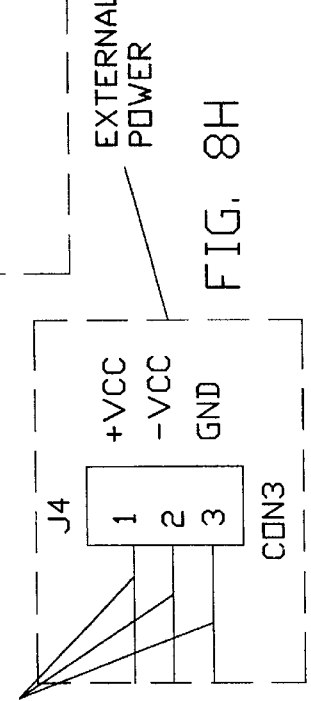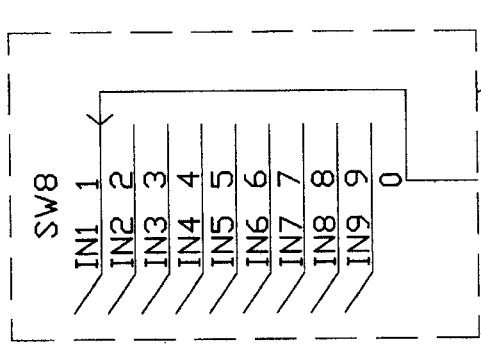

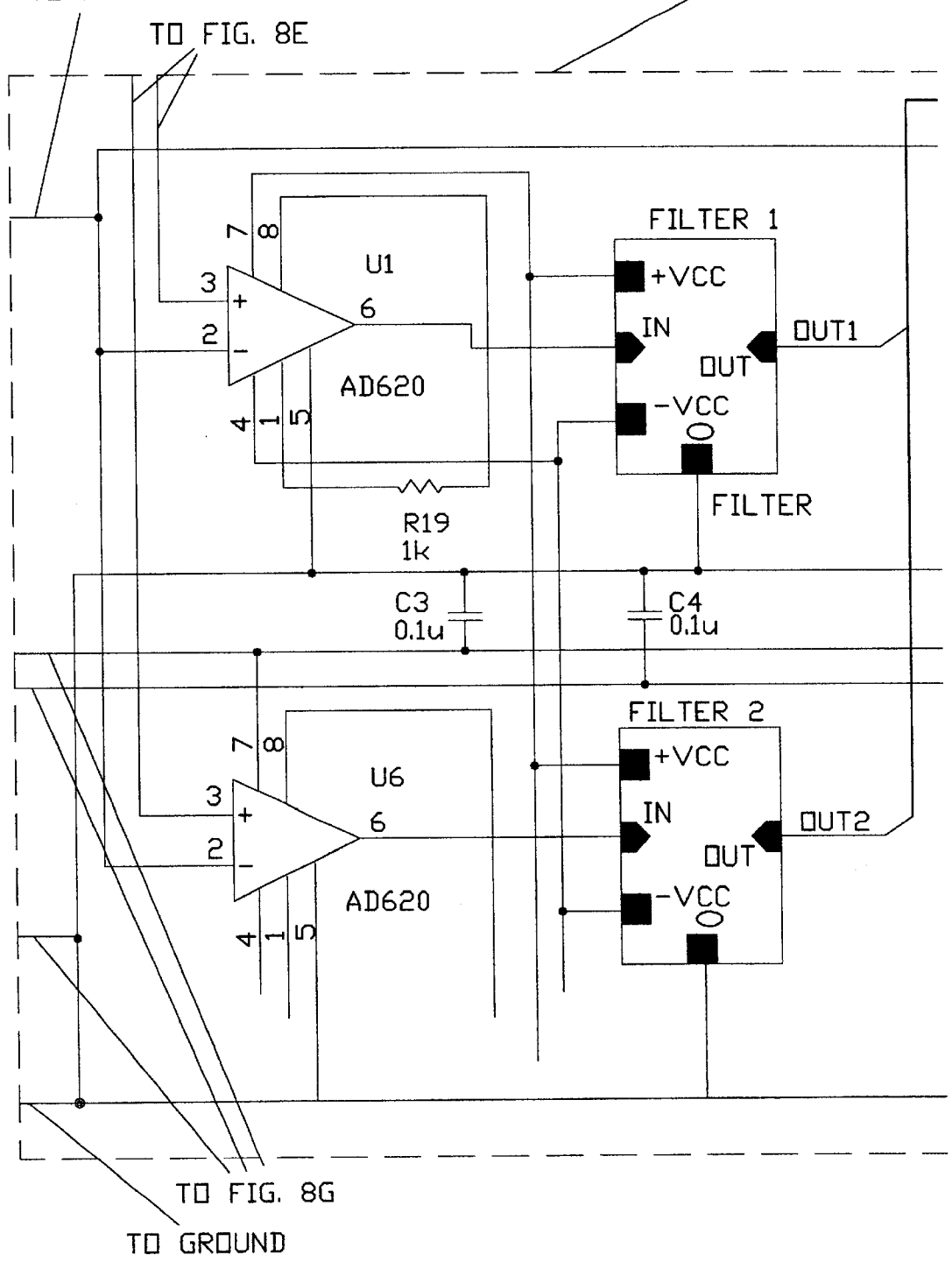

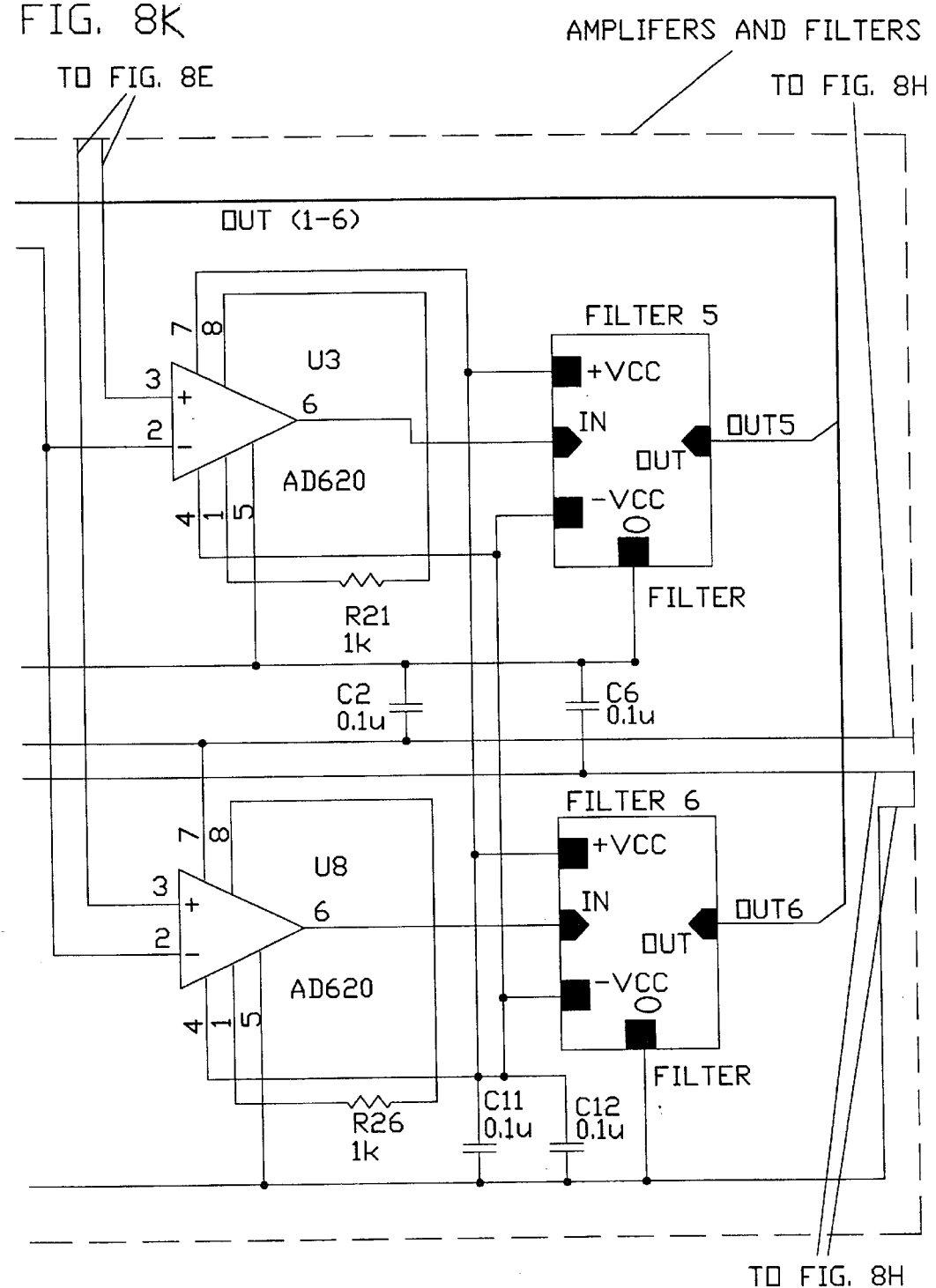

PARALLEL GAS CHROMATOGRAPH WITH MICRODETECTOR ARRAY

RELATED APPLICATIONS

The present application claims the benefit of, and priority to U.S. Ser. No. 60/222,540 entitled "Parallel Gas Chromatograph with Microdetector Array" filed Aug. 2, 2000 by Srinivasan et al., which is hereby incorporated by reference for all purposes.

BACKGROUND OF INVENTION

The present invention generally relates to gas chromatography, and specifically, to parallel gas chromatograph systems that can be integrated or used with parallel reactors for high-throughput (i.e., combinatorial) catalyst screening. The present invention also generally relates to microdetectors, and specifically, to microfabricated thermal conductivity detectors suitable for use in gas chromatography, flow detection, catalyst characterization, and other applications. The invention particularly relates, in a preferred embodiment, to parallel gas chromatograph systems with an array of microdetectors, such as microfabricated thermal conductivity detectors.

Gas chromatography, and in particular, multi-channel gas chromatography is known in the art. See, for example, PCT patent application WO 00/23734 (Daniel Industries, Inc.). Thermal conductivity detectors are also known in the art, and have been routinely used for detection in gas chromatographs—alone, or in combination with other detectors. See, for example, U.S. Pat. No. 4,594,879 to Maeda et al., and Great Britain Patent Specification GB 1,262,529.

Combinatorial (i.e., high-throughput) catalysis is likewise known in the art. See U.S. Pat. No. 5,985,356 to Schultz et al., U.S. Pat. No. 6,004,617 to Schultz et al., U.S. Pat. No. 6,030,917 to Weinberg et al., U.S. Pat. No. 5,959,297 to Weinberg et al., U.S. Pat. No. 6,063,633 to Wilson, U.S. Pat. No. 6,149,882 to Guan et al., and PCT applications WO 99/64160, WO 99/51980, WO 00/09255, WO 00/23921, WO 00/32308 and WO 00/51720 each of which patents and applications relates to various aspects of combinatorial materials science and combinatorial catalysis, and each of which (including corresponding US applications from which priority is claimed) is hereby incorporated by reference for all purposes.

Despite the considerable development in the art of gas chromatography to date, there remains a need for improved gas chromatographs to facilitate, among other applications, high-throughput screening of catalysts in parallel fashion—with simultaneous injection, separation and/or detection in multiple analysis channels. In particular, the current state of the art suffers from relatively bulky packaging, limited interchangeability of component parts, limited operational flexibilty and considerable manufacturing expense. Moreover, existing gas chromatographs are not readily integrated into reaction systems, and especially into smaller-scale reactors such as microreactors, for catalyst screening and/or process optimization.

SUMMARY OF INVENTION

It is therefore an object of the present invention to provide improved gas chromatographs and improved microdetectors for parallel gas chromatography that overcome the deficiencies of the prior art. Specifically, it is an object of the invention to provide a gas chromatograph that is more spatially efficient, provides more operational flexibility, and is more economical to manufacture. It is also an object of the invention to provide gas chromatograph that is suitable for applications with high-throughput screening (e.g. of catalysts), including screening of catalysts using parallel flow reactors or parallel flow microreactors.

Briefly, therefore, included among the several inventions disclosed herein, are arrays of microdetectors, especially thermal conductivity microdetectors, parallel gas chromatographs comprising such microdetector arrays, and parallel catalyst evaluation systems comprising parallel reactors integrated with such parallel gas chromatographs. The present invention also includes highly parallel gas chromatograph systems (e.g. having more than about 8 channels, and preferably more than about 16 channels) having improved thermal control. Additional inventions, including parallel injection blocks (for simultaneous injection and simultaneous vaporization of liquid samples), independently and collectively with parallel injection valves (for parallel injection of gaseous samples to gas chromatography columns) are also disclosed. Inventive methodologies are likewise disclosed herein, including for example, methods for parallel gas chromatography, methods for evaluating libraries of catalyst candidates using such gas chromatography methods, methods for parallel detection of thermal conductivity, and methods for detecting improper injections to gas chromatograph systems.

More specifically, the present invention is directed to a gas chromatograph having four or more analysis channels for simultaneous analysis of four or more fluid samples. The gas chromatograph comprises four or more gas chromatography columns (each comprising an inlet for receiving a gaseous mobile phase that includes a gaseous sample, a separation media effective for separating at least one separated component of the gaseous sample from other components thereof, and an outlet for discharging the separated gaseous sample) and a microdetector array comprising four or more thermal conductivity microdetectors for detecting the thermal conductivity of said at least one separated component of the gaseous sample, said thermal conductivity microdetectors being integral with a substrate or mounted on the substrate. The four or more thermal conductivity microdetectors generally have an inlet port in fluid communication with the outlet of one or more of the gas chromatography columns for receiving a separated gaseous sample, a detection cavity, a thin-film detection filament within the detection cavity for detecting at least one separated component of the separated gaseous sample, and an outlet port for discharging the separated gaseous sample.

The gas chromatographs of the present invention include several variously characterized embodiments. The microdetectors are, in one embodiment, preferably microfabricated microdetectors that are integral with the substrate or with one or more microchip bodies mounted on the substrate. In another embodiment, the microdetectors are thermal conductivity detectors comprising a thin-film detection filament in the detection cavity, where the detection filament has a temperature-dependent resistance. In additional embodiments described in greater detail hereinafter, the microdetectors are bonded to the substrate, or are alternatively detachably mounted on the substrate, preferably as microchip bodies comprising one or more microdetectors In a particularly preferred embodiment, the gas chromatograph is a six-channel gas chromatograph for simultaneous analysis of six or more fluid samples. The gas chromatograph can comprise six or more gas chromatography columns (each of the six or more gas chromatography columns comprising an inlet for receiving a gaseous mobile phase that includes a gaseous sample, a separation media effective for separating at least one component of the sample from other components thereof, and an outlet for discharging the mobile phase and the separated sample) and a microdetector array comprising six or more sample thermal conductivity detectors and at least one reference thermal conductivity detector. Each of the sample and reference thermal conductivity detectors are integral with or mounted on a substrate with a planar density of at least about 1 thermal conductivity detector per 1 cm$^2$, and the ratio of sample detectors to reference detector(s) is at least 2:1. Each of the six or more sample thermal conductivity detectors comprises an inlet port in fluid communication with the outlet of one of the gas chromatography columns for receiving a separated sample, a detection cavity having a volume ranging from about 1 $\mu$l to about 500 $\mu$l for detecting at least one component of the separated sample, a thin-film detection filament within the detection cavity, the detection filament having a temperature-dependent resistance, an outlet port for discharging the sample, a first conductive path between the a first end of the detection filament and a first electrical contact, and a second conductive path between a second end of the detection filament and a second electrical contact. The first and second electrical contacts are adapted for electrical communication with one or more integral or external signal-processing circuits. The at least one reference thermal conductivity detector has an inlet port in fluid communication with a reference gas source for receiving a reference gas, a detection cavity comprising a thin-film detection filament within the detection cavity for detecting the reference gas, and an outlet port for discharging the detected reference gas. The six or more sample thermal conductivity detectors each have a thermal coefficient of resistance that varies less than about 10% between the six or more thermal conductivity detectors.

The invention is likewise directed to an integrated apparatus comprising a gas chromatograph as set forth (including variations and specific attributes as described or claimed hereinafter), and a parallel flow reactor having four or more reaction vessels. Each of the four or more reaction vessels comprises an inlet for feeding reactants into the reaction vessel, a reaction zone for effecting a chemical reaction, and an outlet for discharging reaction products and unreacted reactants, if any. The outlets of the four or more reaction vessels can be in at least sampling fluid communication with the inlets of the four or more gas chromatography columns, respectively. The parallel flow reactors can be typical bench scale, or smaller scale, such as massively-parallel microreactors (e.g., as described in WO 00/51720) or intermediate scale parallel-flow reactors (e.g., such as the parallel fixed bed reactors as described in U.S. Pat. No. 6,149,882 to Guan et al., commercially available from Zeton Altamira (Pittsburgh, Pa.) and, with higher numbers of reaction channels, from Symyx Technolgies, Inc. (Santa Clara, Calif.).

The invention is further directed to a microdetector array comprising four or more thermal conductivity detectors. The four or more thermal conductivity detectors are integral with or mounted on a substrate with a planar density of at least about 1 thermal conductivity detector per 10 cm$^2$. Each of the thermal conductivity detectors comprise a detection cavity having a volume of not more than about 500 $\mu$l, an inlet port for admitting a fluid sample into the detection cavity, one or more thin-film detection filaments within the detection cavity, the detection filament having a temperature-dependent resistance, an outlet port for discharging a fluid sample from the detection cavity, first and second electrical contacts for electrical communication with a signal-processing circuit, a first conductive path between the first electrical contact and a first end of the detection filament, and a second conductive path between the second electrical contact and a second end of the detection filament. In preferred embodiments, the microdetectors are mounted on the substrate, individually or as modules, by being bonded to the substrate, or by being detachably mounted on the substrate, in either case, preferably as microchip bodies comprising one or more of the thermal conductivity microdetectors.

The invention is directed, moreover, to a method for parallel analysis of four or more fluid samples by gas chromatography. The method comprises injecting four or more gaseous samples into respective mobile phases of four or more gas chromatography columns, contacting the four or more gaseous samples with separation media in the respective gas chromatography columns to separate at least one component of the sample (i.e., one analyte) from other constituents of the gaseous samples, and detecting the four or more separated analytes with a microdetector array comprising four or more microdetectors. The array of microdetectors are preferably microfabricated microdetectors (e.g., TCD's). The array preferably comprises four or more thermal conductivity detectors having one or more thin-film detection filaments in the detection cavity. In preferred embodiments, the array comprises microdetectors integral with or mounted on the substrate. The microdetectors can be mounted, individually or as modules, by being bonded to the substrate, or by being detachably mounted on the substrate, in either case, preferably as microchip bodies comprising one or more of the thermal conductivity microdetectors.

The invention is also directed to a gas chromatograph, and methods of using the same, where the gas chromatograph has larger numbers of analysis channels—especially to systems having eight or more, and preferably sixteen or more, twenty-four or more, forty-eight or more or ninety-six or more gas chromatography columns adapted for simultaneous analysis of a like number of samples (e.g. such as are generated in a combinatorial catalysis experiment). Specifically, the gas chromatograph comprises eight or more gas chromatography columns residing in a heated environment, and a detector array comprising eight or more detectors (i.e. at least eight detection channels, whether in a single instrument, such as the preferred microdetector array described above, or in separate conventional detection instruments). Each of the of the eight or more gas chromatography columns have an inlet for receiving a gaseous mobile phase that includes a gaseous sample, a separation media effective for separating at least one component of the sample from other components thereof, and an outlet for discharging the separated sample. The heated environment is adapted to provide substantially the same temperature profile, temporally, for the eight or more gas chromatography columns—as measured at substantially the same spatial location on each column at a given time during a temperature excursion of at least about 10° C. In particular, the temperature of the eight or more columns is preferably substantially the same—as measured as such, and preferably does not vary by more than about 10° C., preferably not more than about 5° C., 2° C., 1° C., 0.5°, and 0.1° C., as measured as such. Additionally or alternatively, the heated environment provides a substantially uniform time-rate-of-change in temperature to each of the eight or more gas chromatography columns (e.g., during a temperature ramping excursion)—as measured at a given time during a temperature excursion at substantially the same spatial location of the compared columns. Preferably, the rate of change in temperature varies by not more than about 10%, and preferably not more than about 5%, 2%, 1%, or 0.5% as measured as such. In a particularly preferred embodiment, the heated environment comprises a convection zone for directed flow of a fluid in a substantially uniform direction past the eight or more gas chromatography columns. In any case, the eight or more detectors each have an inlet port in fluid communication with the outlet of one or more of the gas chromatography columns for receiving a separated sample, a detection cavity for detecting at least one component of the separated sample, and an outlet port for discharging the sample.

The invention is additionally directed to methods for evaluating the catalytic performance of candidate catalysts. Four or more candidate catalysts are simultaneously contacted with one or more reactants in a parallel reactor under reaction conditions to catalyze at least one reaction, and the resulting reaction products or unreacted reactants are detected in parallel with the gas chromatographs of the invention, as described or claimed herein, to determine the relative performance of the candidate catalysts. The candidate catalysts can be the same or different between reaction channels, and the reaction conditions (e.g., temperature, pressure, feed flowrate, residence time, feed composition) can likewise be the same or different between reaction channels.

The parallel detection systems of the present invention are of substantial importance for high-throughput combinatorial catalysis research programs. Parallel screening reactors, such as flow reactors as disclosed in U.S. Ser. No. 09/093, 870 filed Jun. 9, 1998 by Guan et al. (herein "98-13", and now issued as U.S. Pat. No. 6,149,882), U.S. Ser. No. 09/518,794 filed Mar. 3, 2000 by Bergh et al. (herein "99-1"), U.S. Ser. No. 60/185,566 filed Mar. 7, 2000 by Bergh et al. (herein "00-022"), U.S. Ser. No. 09/801,390, entitled "Parallel Flow Process Optimization Reactors" filed on the date even herewith (Mar. 7, 2001) by Bergh et al., U.S. Ser. No. 09/801,389, entitled "Parallel Flow Reactor Having Variable Composition" filed on the date even herewith (Mar. 8, 2001) by Bergh et al., and U.S. Serial No. 60/274,065, entitled "Parallel Flow Reactor Having Improved Thermal Control" filed on the date even herewith (Mar. 7, 2001) by Bergh et al. can effect reactions in tens, hundreds or even thousands of channels simultaneously or substantially concurrently. Parallel detection systems, such as two-channel gas chromatography systems, have been advantageously applied in connection with some such parallel reaction systems, but are inherently limited by their size (bulk) and, significantly, by their cost per channel.

The parallel detection systems disclosed herein, comprising a microdetector array, overcome the substantial cost and space constraints of conventional gas chromatographs. The gas chromatographs of the present invention also offer significant improvements with respect to modularity and interchangeability of components, and especially of the detectors. Significantly, the microfabricated microdetectors can be economically manufactured using conventional microfabrication techniques, allowing for improved manufacturing approaches. Microfabrication also provides reproducible, advantageous performance characteristics, especially when applied in connection with forming thin-film detection filaments. The detection systems disclosed herein also provide improvements in sample-handling efficiency and, as such, improve overall sample throughput for a catalysis research program.

The apparatus and methods are disclosed herein primarily in the context of gas chromatography, and particularly in connection with combinatorial catalysis research programs. The inventions are broadly useful in such programs, including for example, heterogeneous catalysis and homogeneous catalysis, as applied in commodity chemicals, fine chemicals, and/or specialty chemicals, with flow, semi-continuous, and/or batch reactor systems.

The apparatus are also useful, however, in other applications. For example, other applications for the parallel thermal conductivity array are contemplated, including parallel flow sensing (e.g. parallel flow anemometers), and parallel catalyst characterization (e.g., using parallel temperature-programmed desorption, parallel temperature-programmed reduction, and/or parallel temperature-programmed oxidation protocols). The parallel detection apparatus (i.e., gas chromatographs and/or microdetector arrays) and methods can also be employed in connection with environmental sensing, process monitoring, process control, defense, first-responder and other applications. In some applications, the parallel gas chromatograph and associated methods can be applied to evaluation of chromatography media for gas chromatography columns (e.g. having a different media in each column, injecting the same sample into each of the columns and comparing the detected separation effect). Additional applications will be apparent to those of skill in the art.

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIGS. 1A through 1D are schematic diagrams showing various multi-channel gas chromatograph systems.

FIGS. 2A through 2F are a cross-sectional end view (FIG. 2A) and a perspective view (FIG. 2B) of a parallel injection block for simultaneous vaporization of multiple liquid samples, as well as detail cross-sectional views (FIGS. 2C, 2D, 2E) and cut-away perspective view (FIG. 2F) of a mechanical septum for use with the injection block.

FIGS. 3A through 3C are a perspective view (FIG. 3A) and schematic views (FIGS. 3B, 3C) of a parallel injection valve for gas chromatography.

FIGS. 5A through 5M are schematic views (FIGS. 5A, 5B, 5C, 5D, 5J, 5K), a cross-sectional-top plan view (FIG. 5E), cross-sectional views (FIG. 5F—taken at A—A of FIG. 5E, FIG. 5G—taken at B—B of FIG. 5E), photographs (FIGS. 5H, 5I), and perspective views (FIGS. 5L, 5M) of a detection cavity comprising a thin-film detection filament.

FIGS. 8A through 8K are schematic diagrams for the electrical circuitry associated with the parallel thermal conductivity microdetectors of the invention.

Figure 1B:
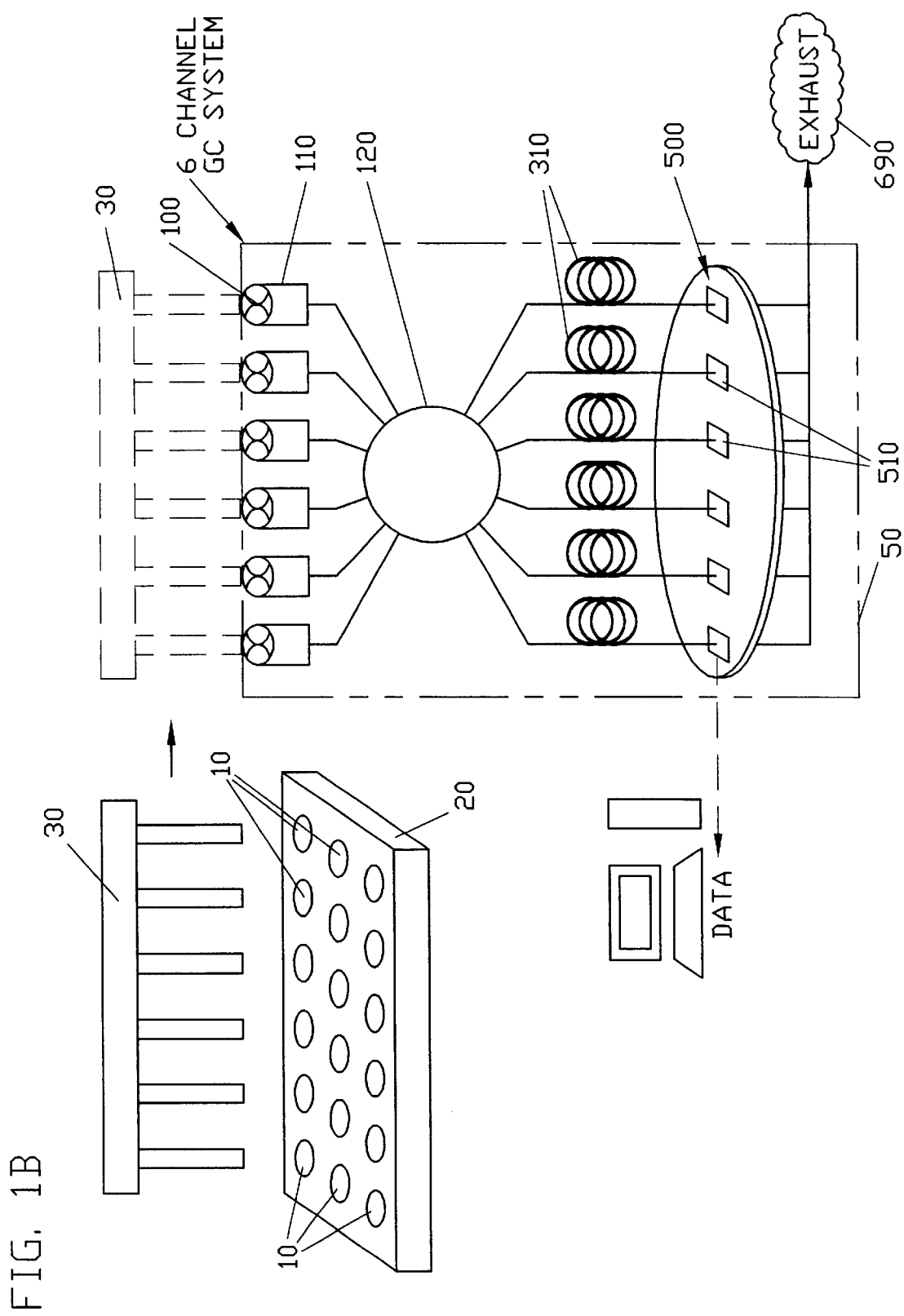

The invention is described in further detail below with reference to the figures, in which like items are numbered the same in the several figures.

DETAILED DESCRIPTION OF THE INVENTION

The present application is related to the following U.S. patent applications, each of which is hereby incorporated by reference for all purposes: U.S. Ser. No. 09/093,870 filed Jun. 9, 1998 by Guan et al. (herein "98-13"), now issued as U.S. Pat. No. 6,149,882; U.S. Ser. No. 09/518,794 filed Mar. 3, 2000 by Bergh et al. (herein "99-1"); U.S. Ser. No. 60/185,566 filed Mar. 7, 2000 by Bergh et al. (herein "00-022"); U.S. Ser. No. 09/801,390, entitled "Parallel Flow Process Optimization Reactors" filed on the date even herewith (Mar. 7, 2001) by Bergh et al.; U.S. Ser. No. 09/801,389, entitled "Parallel Flow Reactor Having Variable Composition" filed on the date even herewith (Mar. 8, 2001) by Bergh et al.; and U.S. Serial No. 60/274,065, entitled "Parallel Flow Reactor Having Improved Thermal Control" filed on the date even herewith (Mar. 7, 2001) by Bergh et al.; U.S. Serial No. 60/274,022 entitled "Microvalve Arrays for Gas Chromatograph Injection" filed on the date even herewith (Mar. 7, 2001) by Bergh et al.; U.S. Ser. No. 09/285,363 filed Apr. 2, 1999 by Petro et al. (herein "99-9"); U.S. Ser. No. 09/174,856 filed Oct. 19, 1998 by Lacy et al. (herein "98-11"); U.S. Ser. No. 09/156,827 filed Sep. 18, 1998 by Giaquinta et al. (herein "99-21"); and U.S. Ser. No. 09/516,669 filed Mar. 1, 2000 by Lugmair et al. (herein "99-66").

With reference to FIG. 1A, a gas chromatograph 1 can have four or more analysis channels for simultaneous analysis of four or more fluid samples—gaseous or liquid samples 10. The gas chromatograph 1 generally comprises a set 300 of four or more gas chromatography columns 310 and a microdetector array 500 comprising four or more microdetectors 510. An injection system 100 can inject the four or more fluid samples 10, directly (if gaseous samples) or after vaporization to form gaseous samples (if liquid samples), into a mobile phase flowing through each of the four or more gas chromatography columns 310. At least one components (i.e., analytes) of the gaseous samples are separated from other components thereof in the columns 310, and the at least one separated component is detected in the microdetectors 510. Following detection, the samples can be exhausted through one or more individual or common exhaust manifolds 690.

In operation, the parallel gas chromatograph can advantageously be used for simultaneous gas chromatography detection of analytes in four or more gas samples. Specifically, the method comprises simultaneously injecting four or more gas samples into four or more corresponding gas chromatography columns, each of the four or more gas chromatography columns comprising a separation media, simultaneously contacting the four or more gas samples with the separation media in the respective gas chromatography column to separate at least one analyte from other constituents of the gas samples, and simultaneously detecting the four or more separated analytes with a microdetector array comprising four or more microdetectors.

Gas Chromatograph

The gas chromatograph of the invention generally comprises four or more analysis channels. Specifically, four or more gas chromatography columns are configured for parallel analysis of four or more gaseous samples with detection being effected using a microdetector array comprising four or more microdetectors.

The gas chromatography columns 310 (FIG. 1A) are not critical. Generally, each of the four or more gas chromatography columns comprises an inlet for receiving a gaseous mobile phase that includes a gaseous sample, a separation media effective for separating at least one component of the sample from other components thereof, and an outlet for discharging the separated sample. Conventional columns as are known in the art can be readily applied. Alternatively, the gas-chromatography columns can be capillaries or microchannels having nano-sized, micron-sized or milli-sized dimensions. The separation media is not critical, and can include, for example, solid, gel or liquid—contained in the column in any manner, including for example, as a packing or as a surface coating. A column having a stationary phase separation media of [x% Phenyl-(100-x%)dimethyl] polysiloxane, polystyrene-divinylbenzene (PLOT Q), molecular sieves, and other separation media are suitable for many applications. The separation media can be the same or different (e.g., with respect to composition, shape, packing arrangement etc.) as compared between columns. The mobile phase flow rate is not critical, and can vary over conventionally-known ranges. A mobile phase (i.e. carrier gas) flow rate of about 1 sccm in each of the analysis channels is typical.

The gas chromatography columns 510 are preferably enclosed in a heated environment (e.g., oven), with temperature control capabilities ranging, without limitation from about −10° C. to about 400° C., more typically from about room temperature to about 400° C., and often from about 40° C. to about 400° C. Conventional ovens can be readily employed with most embodiments of the invention. Preferably, however, the heated environment is adapted as described herein to provide significantly improved thermal control, as compared to conventional ovens, for systems having larger numbers (e.g. eight or more as described below) of gas chromatography columns. More specifically, the heated environment is adapted to provide a substantially (temporally) uniform temperature profile as compared between the eight or more columns. For example, the temperature of each of the eight or more columns—taken at substantially the same spatial location on each column at a given time during a temperature excursion of at least about 10° C.—preferably varies by not more than about 5° C., more preferably by not more than about 2° C., even more preferably by not more than about 1° C., still more preferably by not more than about 0.5° C., and most preferably by not more than about 0.1° C. Additionally, in some embodiments, the time-rate-of-change in temperature of the eight or more gas chromatography columns—measured at substantially the same spatial location on each column at a given time during a temperature excursion of at least about 10° C.—preferably varies by not more than about 10%, preferably by not more than about 5%, more preferably by not more than about 2%, still more preferably by not more than about 1%, and most preferably by not more than about 0.5%. The thermal profiles are preferably substantially consistent between columns (as specifically and variously characterized above) during a temperature excursion of at least 20° C., and more preferably of at least about 50° C.

Figure 11A:
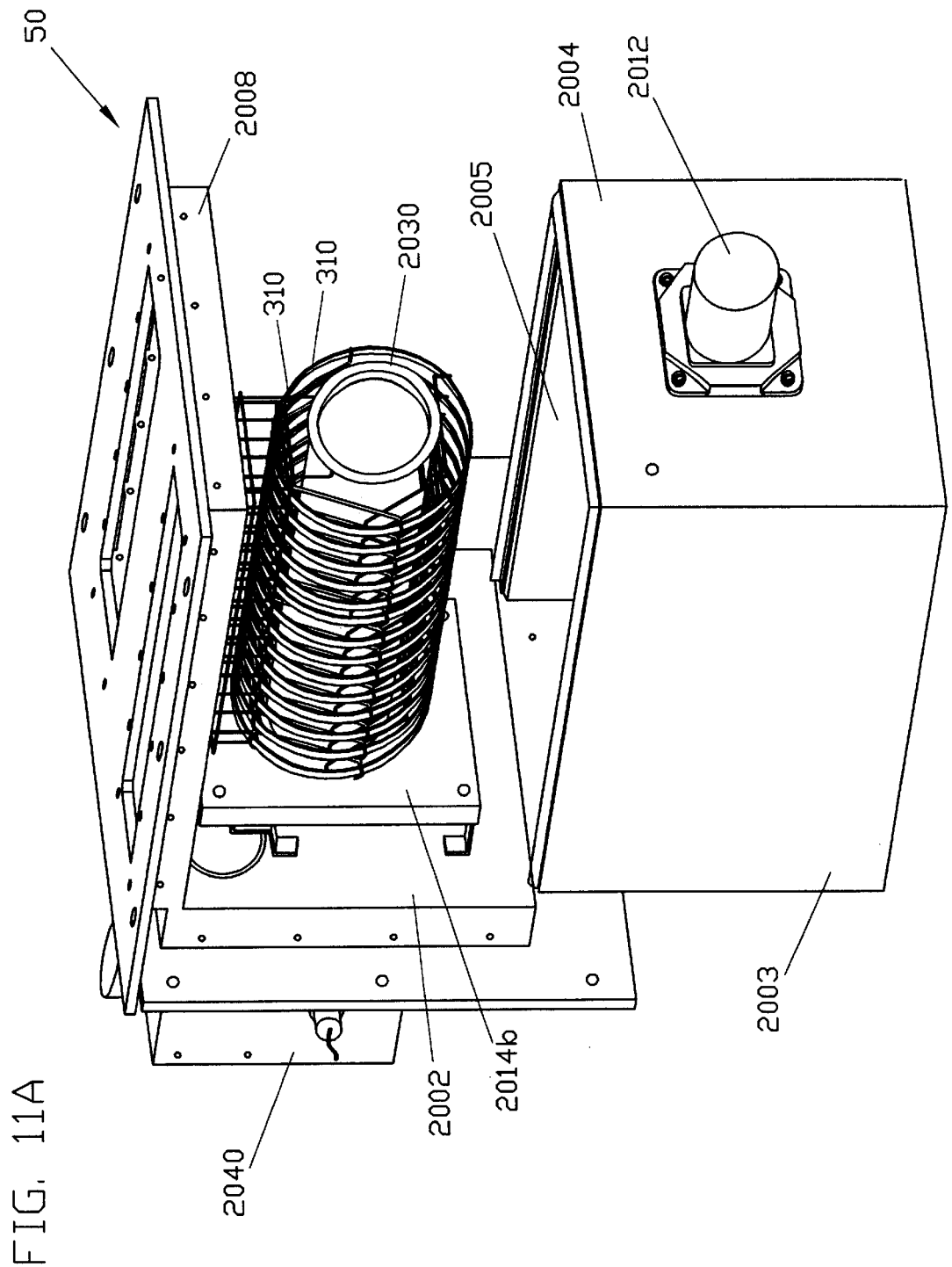
FIGS. 11A and 11B are perspective views of a heated environment (e.g., oven) adapted for directed forced convection flow in a substantially uniform direction across multiple gas chromatography columns.
Figure 11B:
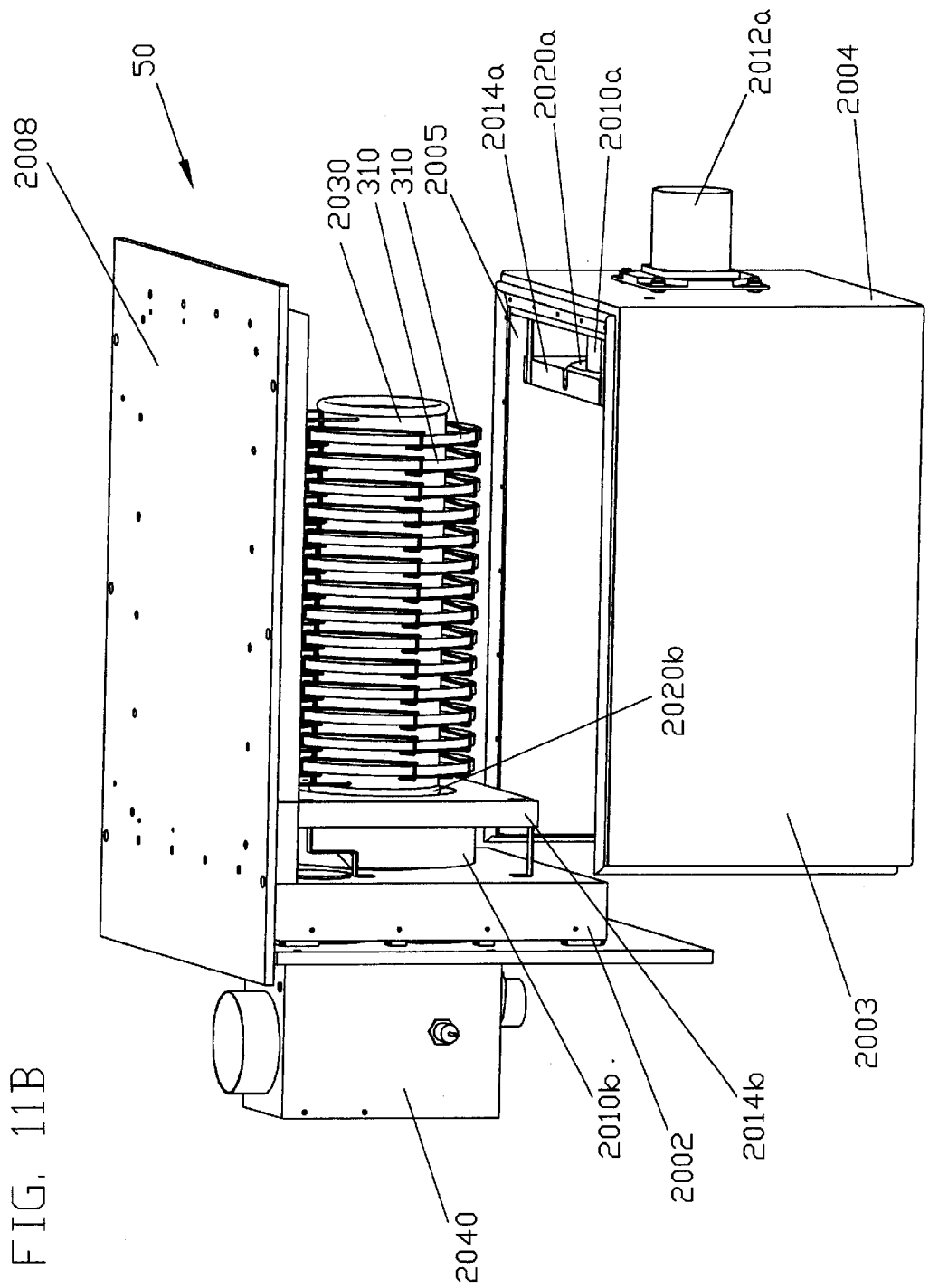

In a particularly preferred embodiment, the heated environment comprises a forced convection zone created by one or more convection fans, and preferably by two or more convection fans, with the eight or more columns residing at least partially, and preferably entirely within the forced convection zone. Additionally or alternatively, the heated environment preferably comprises a forced convection zone for directed flow of a fluid in a substantially uniform direction past (e.g., in contact, at and/or around) the eight or more gas chromatography columns. A directed flow of fluid is moving in substantially the same uniform direction, for example, if the bulk motion of the fluid (ignoring back-eddies, side eddies, and generally, turbulence) is toward a unitary, downstream point, curvilinear, or plane. As such, the flow can be laminar flow, but is preferably turbulent flow. With reference to FIGS. 11A and 11B, and without limitation to general concept, a heated environment 50 can be defined by the internal surfaces of first, second, third and fourth sides 2002, 2003, 2004, 2005, and bottom (not shown) and top 2008. A forced convection zone can be defined by a zone of substantially uniformly directed turbulent fluid flow, preferably generally between two or more convection fans 2010a, 2010b—at least one fan on each of two opposing sides of the eight or more gas chromatography columns 310. The fans 2010a, 2010b can each be supported by a support shroud 2014a, 2014b, respectively, and can be driven by a motor 2012a (shown only for fan 2010a) for rotational driving force. In a preferred embodiment, the heated environment includes a chimney 2030 adapted to direct the fluid flow within the chimney from one or more convection fans on first side of the eight or more gas chromatography columns to one or more opposing convection fans on an opposing second side of the eight or more gas chromatography columns, optionally with return flow from the second side back along the outside of the chimney to the first side. The gas chromatography columns can be either within the chimney (e.g. in the direct flow) or external to the chimney (e.g., in a return flow-path). Likewise, the fans can be provided in the proximity of the interior wall of the heated environment, or can be integral with such an interior wall. The particular orientation is not critical—such that the set of opposing fans can be placed across from each other at the top and bottom, at the left side and right side, at the front side and back side, or across diagonals, etc. As illustrated in FIGS. 11A and 11B, the flow is orientated from a first fan 2010a (e.g., an axial fan) which intakes a fluid radially, an blows the fluid axially through a chimney 2030 to a second fan 2010b (e.g. a circumferential fan). The second fan 2010b can intake the fluid from within the chimney 2030, and discharge the fluid radially outward, around the backside of the support shroud 2014b (i.e., through the gap between the support shroud 2014b and a first sidewall 2002 to create a return flowpath that runs along the exterior of the chimney 2030, past the columns 310, and back to the circumferential intake of the first radial fan 2010a. One or more circumferential heaters 2020a, 2020b can be also be supported by the shrouds 2014a, 2014b, to heat the fluid being forced through the chimney 2030 and returned externally thereto past the columns 310. A cold-flow duct 2040 adapted for selective admission of unheated air (typically from the atmoshpere external to the heated environment) can also be used, substantially in the conventional manner.

The number of gas chromatography columns 310 can be the same or different as the number of microdetectors 510. For example, there can be more than one column per detector (as contemplated, for example, in PCT application WO 00/23734). Alternatively, there could be more than one microdetector 510 associated with each column 310 (e.g. two detectors of the same of different types). Accordingly, although the invention is described herein, and preferably applied in some applications, with a one-to-one correspondence between gas chromatography columns 310 and detectors 510, the invention is not limited to such a configuration, and persons of skill in the art can readily adapt the invention as disclosed to other such configurations. In general, the nature of the inventions described and claimed herein are particularly advantageous with respect to a gas chromatograph, and methods of using the same, where the gas chromatograph has larger numbers of analysis channels—especially to systems having eight or more, and preferably sixteen or more, twenty-four or more, forty-eight or more or ninety-six or more gas chromatography columns adapted for simultaneous analysis of a like number of samples (e.g. such as are generated in a combinatorial catalysis experiment).

The microdetector array 500 generally comprises four or more detectors 510 integral with, or alternatively, mounted on a substrate 600. The four or more microdetectors 510 are generally flow detectors, and comprise an inlet port in fluid communication with the outlet of one or more of the gas chromatography columns for receiving a separated sample, a detection cavity for detecting at least one component of the separated sample, and an outlet port for discharging the sample. The microdetectors can be any type of detector suitable for gas chromatography detection. Preferred detectors include those selected from the group consisting of thermal conductivity detectors, photoionization detectors, optical emission detectors, flame ionization detectors, surface acoustic wave detectors and pulse discharge detectors. Thermal conductivity detectors are particularly preferred in connection with the present invention (including in particular, with this embodiment of the invention), for many applications, in view of their universality (with respect to capabilities for analyzing various types of samples) and sensitivity (with respect to capabilities to detect low concentrations of analyte). Thermal conductivity detectors are advantageous, for example, with respect to relative simplicity of the electronics, a lack of hysteresis concerns, etc. Other types of detectors may, however, be advantageously applied for particular applications of interest. For each types of detectors, the detectors may further comprise other components, as appropriate, including for example, a detection filament having a temperature-dependent resistance for thermal conductivity detectors, or as another example, windows transparent to electromagnetic energy of particular wavelengths of interest (e.g. an optically-transparent window) for detector types requiring application of such electromagnetic energy. Although the invention is described in further detail herein primarily in connection with thermal conductivity detectors, the invention is not limited to such detectors unless specifically recited in the claims. A person of skill in the art can adapt the concepts disclosed herein for applications to other types of detectors.

In one embodiment, the four or more microdetectors 510 are microfabricated detectors, and are integrally formed with (or equivalently, integrally situated on in) a substrate or with one or more microchip bodies (i.e., microchip sub-substrates), typically mounted on or in the substrate. The microchip bodies can comprise one or more microfabricated microdetectors and can be mounted—fixedly mounted (e.g. bonded) or detachably mounted (e.g. with a releasable seal)—on the substrate (e.g. on a surface of the substrate). The substrate or microchip bodies can be of any material suitable for microfabrication processes. Silicon, and preferably single-crystal silicon is a preferred material for the substrate or microchip bodies in this embodiment. Other materials can also be employed, including for example, as generally discussed below. The microdetectors can be microfabricated (in the substrate or in the one or more microchip bodies) using a variety of known, or later-developed microfabrication techniques, including for example one or more of the techniques selected from the group consisting of oxidation, masking, etching, thin-film deposition, planarization and bonding. Other microfabrication techniques, although not specifically recited herein, can also be used to form the microdetectors 510 in the substrate or in the microchip bodies. Preferably, the detector is a thermal conductivity detector that comprises a detection filament having a temperature-dependent resistance. The detection filament in this embodiment can be (but is not necessarily) a thin-film detection filament.

In another embodiment, the microdetector array comprises four or more thermal conductivity detectors integral with or mounted on a substrate, each comprising one or more thin-film detection filaments. Specifically, with reference to FIG. 5A, each of the four or more thermal conductivity microdetectors 510 in this embodiment comprises an inlet port 512 in fluid communication with the outlet of one or more of the gas chromatography columns for receiving a separated sample, a detection cavity 516 comprising at least one thin-film detection filament 520 within the detection cavity 516 for detecting at least one component of the separated sample, and an outlet port 514 for discharging the sample from the detection cavity 516. As discussed below, the particular design of the thermal conductivity detector is not narrowly critical, and can include known or later-developed designs.

The thin-film detection filament in this embodiment comprises a film of material having a temperature-dependent resistance formed on or in a support (e.g. on a support bridge). Platinum or mixed-metal oxides are exemplary, non-limiting materials that are suitable for the thin-film detection filament. Platinum is preferable for higher temperature applications (e.g., up to about 400° C.). A mixed-metal oxide, similar to what is typically used in conventional thermistor-type detectors, can be preferably for some applications requiring higher sensitivities, but at lower temperature operations (e.g., up to about 100° C.). The thickness of the film of material is not critical. Typically, the film thickness can range from about 10 angstroms to about 1 mm, preferably from about 10 angstroms to about 100 $\mu$m, preferably still from about 100 angstroms to about 10 $\mu$m, and more preferably from about 500 angstroms to about 1 $\mu$m. The film thickness can be most preferably about 0.1 $\mu$m (i.e., about 1000 angstroms). The nature of the support (e.g. with respect to material and/or design) is likewise not critical. The support material and design should be selected to be robust in connection with the application for which it is being designed. Silicon nitride is an exemplary and preferred support material. Other materials, such as polysilicon, silicon, silicon dioxide, and silicon carbide, among others, can also be employed as the support material. The support material is generally suspended in the detection cavity such that the thin-film detection filament can be contacted with the gaseous sample being detected. Further design considerations for the detection filament are discussed below, together with other general features of the invention. The thin-film detection filament is preferably (but is not necessarily) a microfabricated detection filament.

Advantageously, thin-film detection filaments can be designed with a variety of surface geometries and a corresponding variety of associated surface areas for contact with the gaseous sample. As non-limiting examples, the thin-film detection filament can include a serpentine design, a zig-zag design, or a square-point meandering design, among others, on a support of the same design or on substantially planar support. Thin-film detection filaments can also be made with a substantial variety of materials elements and compounds or alloys, to provide various detection attributes, depending on the application of interest. As such, the substantial design flexibility offered in connection with thin-film detection filaments provides a fundamental advantage over conventional, thermistor-based (e.g., bulk wire type) detection filaments. Significantly, higher sensitivities can be achieved as compared to most conventional TCD's by optimizing the heat-transfer characteristics associated with the bridge support structure.

Except as otherwise expressly noted, each of the various features of the invention (including especially those described in greater detail below) are general to each of the aforementioned embodiments, and as such, should be considered part of the invention in any and all of the various permutations in which they can be combined and remain with in the scope and context of the embodiments as generally describe above.

The particular design of the thermal conductivity detector is not narrowly critical. In particular, any thermal conductivity detector design suitable for detection of a gaseous component can be used in connection with the present invention, and the particular design features discussed herein are to be considered exemplary unless expressly recited in the claims. With reference to FIGS. 5A through 5D, for example, the orientation of the inlet port 512 and the outlet port 514 to the detection cavity 516 can vary. The inlet port 512 and outlet port 514 can each be directionally aligned with the axial dimension and flowpath of the detection cavity 516 (FIG. 5A), or can be directionally normal thereto (FIGS. 5B through 5D). Likewise, the particular orientation of the detection filament 520 relative to the detection cavity is not critical to the invention. As shown, for example, the detection filament (and corresponding support for a thin-film detection filament) can be suspended across the axial dimension and flowpath of the detection cavity at an angle (e.g. at a non-normal angle, $\theta$ (FIGS. 5A and 5B), or at a normal angle (FIG. 5C)). The detection filament 520 can also be suspended in the detection cavity 516 directionally aligned with the axial dimension and flowpath of the detection cavity (FIG. 5D). Moreover, a thermal conductivity detector can include more than one detection filament 520 in the detection cavity 516. In some cases, multiple detection filaments can be used to improve the design characteristics of the thermal conductivity detector. In some applications, multiple detection filaments can be used to effect combined, multifunctional detectors, such as a combined thermal conductivity detector and anemometer. The detection filament can comprise or consist essentially of any material (e.g., element, compound (including polymeric materials) or alloy) that has a temperature-dependent resistance. Platinum and mixed-metal oxides, typically transition metal oxides such as tin oxide, gallium oxide, etc. are preferred detection filament materials.

The particular design (e.g., shape, materials, volume etc.) of the detection cavity 516 is likewise not critical. The detection cavity 516 can be of any suitable shape or size or volume. Preferably, the detection cavity 516 is a substantially elongated cavity, and can be defined by interior surfaces machined, microfabricated or otherwise formed in a plurality of laminae or in a monolithic substrate—in any case for example, as a particularly designed three-dimensional shape, as an aperture, as a capillary, as a microchannel, or otherwise. The volume of the detection cavity of each of the four or more thermal conductivity detectors can range from about 1 nl to about 1 ml, preferably from about 1 $\mu$l to about 1 ml, more preferably from about 10 $\mu$l to about 500 $\mu$l, still more preferably from about 25 $\mu$l to about 250 $\mu$l, and most preferably from about 50 $\mu$l to about 150 $\mu$l. A detection cavity volume can be about 100 $\mu$l. The material in which the detection cavity is formed can be any suitable material for a thermal conductivity detection cavity, and is preferably inert at the operating conditions thereof. Silicon is a suitable material. Other materials, such as glass, quartz, fused silica are also suitable for many applications.

Other variations in orientation and/or number of filaments, as well as detection cavity design, are known in the art, and can be selected, together with filament design geometries and other factors, by a person of skill in the art to achieve the required sensitivity, universality and robustness required by the application of interest. Although preferred embodiments are described herein with a particularly preferred design, the invention is not limited as such, unless such design features are particularly recited in the claims.

In a particularly preferred embodiment, the four or more microdetectors are microfabricated thermal conductivity detectors, each having single thin-film detection filament. More specifically, regardless of whether the microdetectors are integral with the substrate or, alternatively, are mounted on the substrate (e.g. integral with a microchip body that is mounted on the substrate), and with reference to FIGS. 5E through 5G, each of the thermal conductivity microdetectors can comprise an inlet port 512 for receiving a gaseous sample, a detection cavity 516 comprising a thin-film detection filament 520 within the detection cavity 516. The thin-film detection filament 520 has a first end 521 and a second end 522. The thin-film detection filament comprises a thin-film resistive platinum or other material having a temperature-dependent resistance on a silicon nitride support bridge or other suitable support bridge, and is suspended across the detection cavity 516 at an acute angle, θ, of about 70 degrees, relative to the direction of gas flow. The angle can be optimized to reduce the sensitivity of the detector to flow noise, including down to about 0 degress (e.g. substantially orientated in the direction of flow. The detection cavity 516 can be sized to be about 6 mm long, about 1 mm wide and about 500 $\mu$m (about 0.5 mm) deep. The thermal conductivity microdetector further comprises a first electrical contact 523 and a second electrical contact 524 for electrical communication between the thermal conductivity detector and one or more integral or external signal-processing circuits. If the microdetector is integral with the substrate, the contacts 523, 524 can be situated at (or equivalently, accessible from) an exposed surface of the substrate. If the microdetector is integral with microchip body mounted on the substrate, the contacts 523, 524 can be situated at (or equivalently, accessible from) an exposed surface of the microchip body. In either case, a first conductive path 525 provides electrical communication between the first electrical contact 523 and a first end 521 of the detection filament 520, and a second conductive path 526 provides electrical communication between the second electrical contact 524 and a second end 522 of the detection filament 520. An outlet port 514 provides for discharging the sample from the detection cavity 516. A photograph of the aforedescribed preferred embodiment is shown as FIG. 5H, with an up-close detail photograph shown as FIG. 5I.

In operation, with reference to the embodiment described in the immediately preceding paragraph, the detection filament 520 is also a heating filament, and is heated by applying electrical power via the first and second circular contact pads 523, 524 outside the detection cavity 516 (also referred to herein as a gas channel). The detection cavity 516 (i.e., gas channel) dimensions and the filament dimensions are chosen such that heat conduction to the gas is the dominant mode of heat transfer. See FIG. 5J (analyzing heat transfer based on conduction, radiation and convection), and also FIG. 5K (analyzing convective heat transfer for the TCD design). In a constant power mode of operation, the changing thermal conductivity of the gas changes the temperature of the filament, which is measured using a Wheatstone bridge. Alternatively, in a constant temperature mode of operation, the changing thermal conductivity changes the power input to the filament.

The substrate can generally be any body in which a thermal conductivity microdetector can be integrally formed or any body having a surface on which a thermal conductivity detector can be mounted, directly (e.g. by itself) or within another distinct body such as a microchip body. The substrate is preferably a substantially planar body having at least two substantially parallel opposing surfaces. In some embodiments (e.g., where the microdetectors are integral with the substrate), the substrate can be a plate-type substrate such as a wafer. In the embodiments in which the array of four or more thermal conductivity detectors are integral with the substrate, the substrate is preferably a machinable material, and most preferably a micromachinable material (i.e., a material suitable for microfabrication techniques)—such as single crystal silicon. Although other suitable materials are known in the art for integral microfabrication of thermal conductivity microdetectors (e.g. gallium arsenide, quartz, glass) silicon offers advantages of scale, availability, well-established fabrication foundries, expense and acceptable thermal conductivity and density, to provide for adequate heat transfer and thermal mass. The substrate can advantageously comprise a plurality of laminae into which various components of the thermal conductivity microdetectors can be fabricated before assembly of the laminae to form the unified substrate. In other embodiments, in which the array of four or more thermal conductivity detectors are mounted on the substrate—either fixedly mounted (e.g. bonded) or detachably mounted (e.g. with a releasable seal)—the substrate can be of any material consistent with the required mechanical strength, operational conditions (e.g. temperature) and mounting approach. Materials having a relatively high thermal conductivity and density are preferred, to provide for efficient heat transfer and a large thermal mass. Copper, stainless steel or other metals are exemplary suitable materials for this embodiment, and may be coated with one or more other materials (e.g. nickel-coated copper) to provide additionally desired properties (e.g., chemical inertness) in combination. Materials that are at least machinable (on a macro-scale) are likewise preferred, to provide for assembly and other features (e.g. thermocouples, etc., as described below. In this embodiment, the substrate can have a mounting surface, and preferably an exposed mounting surface adapted to receive a corresponding mounting surface of the thermal conductivity detectors or of the microchip body comprising the thermal conductivity detectors.

In either of such embodiments (i.e., whether the thermal conductivity detectors are integral with the substrate or mounted thereon), the substrate can further comprise other features. For example, the substrate can comprise multiple passageways for providing fluid communication between the thermal conductivity microdetectors and components (or additional components) of the gas chromatograph that are external to the substrate (e.g. to the gas chromatography columns, whether the columns are integral with or external to the substrate, for receiving gaseous samples; to exhaust ports or exhaust manifolds for discharging samples). In one preferred embodiment, for example, the substrate can further comprise four or more pairs of passages formed in the substrate for fluid communication with the four or more microdetectors, respectively. Each pair of passages can comprise a first inlet passage for fluid communication with the inlet port of one of the microdetectors, and a second outlet passage for fluid communication with the outlet port of the one of the microdetectors. The substrate can also comprise one or more of the electrical components of the thermal conductivity detector for detector operation and data collection. In one embodiment, preferred for example where the thermal conductivity detectors are integrally formed in the substrate (but not limited to such cases), the substrate can further comprise one or more of the following: first and second electrical contacts for electrical communication between the thermal conductivity detector and an integral or an external signal-processing circuit(s); a first conductive path between the first electrical contact and a first end of the detection filament; and a second conductive path between the second electrical contact and a second end of the detection filament. Moreover, the substrate can generally comprise additional components for system operational control, including for example: temperature-measuring devices (e.g., thermocouples, RTD's); heating blocks in thermal communication with a heat source (e.g., a fluid heat exchanger and/or resistive heating elements such as cartridge heaters)—especially if the thermal conductivity array will be located external to the heated environment in which the gas chromatography columns are situated); and/or exhaust ports, exhaust sensors (e.g. flow sensors for leak-testing) or one or more exhaust manifolds.

Figure 5L:
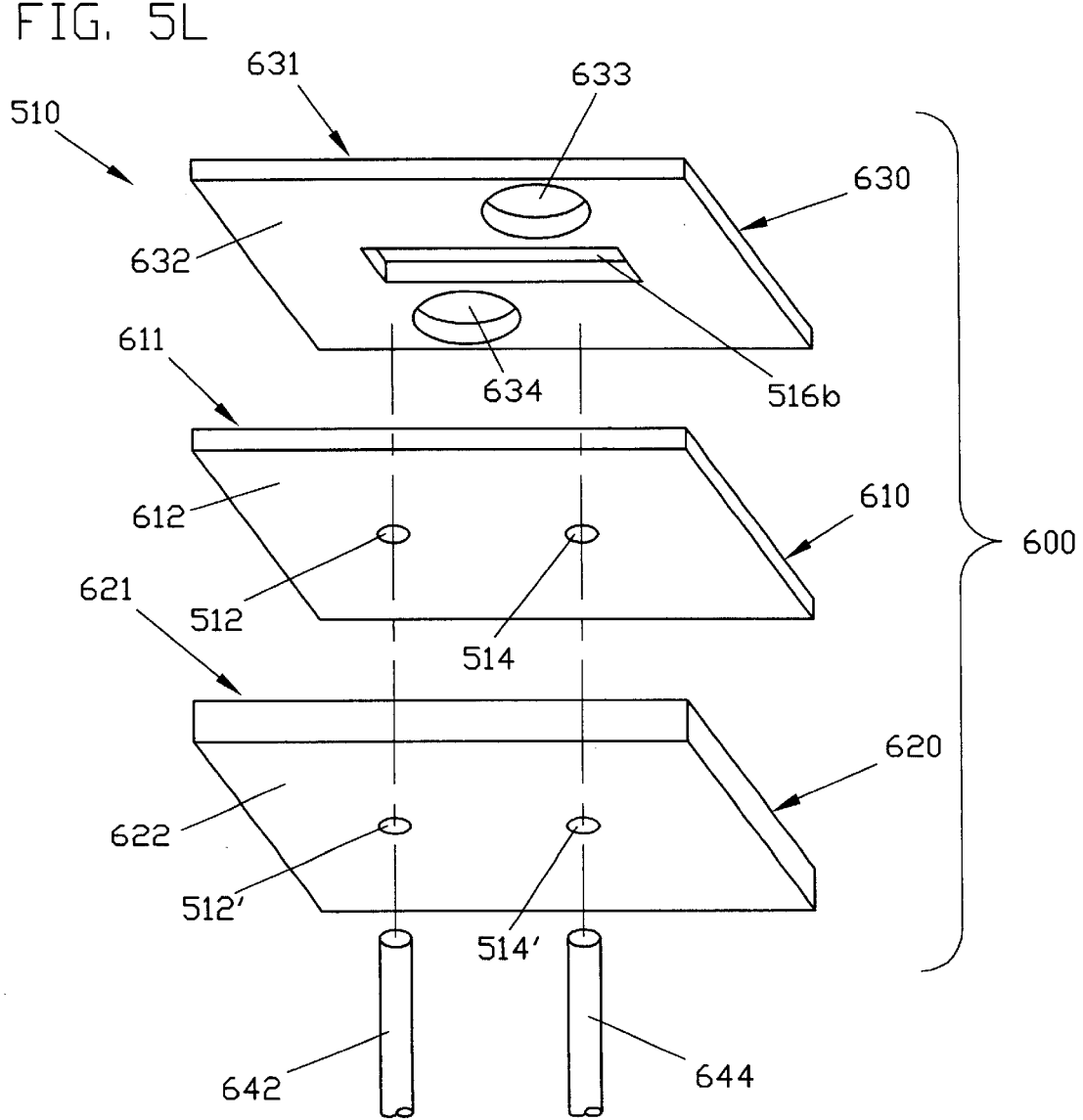
Figure 5M:
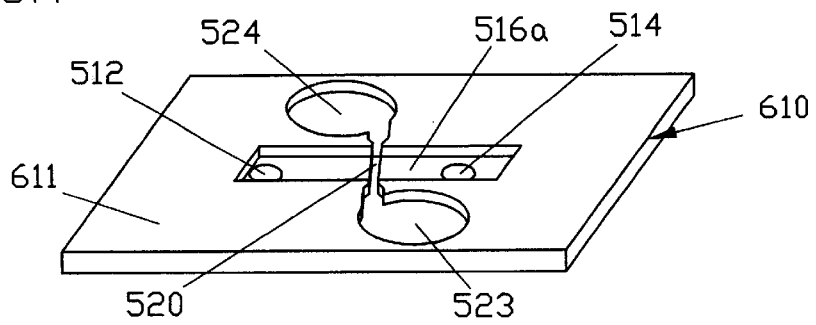

In an embodiment in which the four or more thermal conductivity microdetectors are integral with the substrate, the substrate preferably comprises a plurality of laminae into which into which various components of the thermal conductivity microdetectors can be microfabricated before assembly of the laminae to form the unified substrate. With reference to FIGS. 5L and 5M, for example (showing a single thermal conductivity microdetector, for simplicity of illustration), a thermal conductivity microdetector 510 can be integrally microfabricated with a substrate 600 comprising a first central laminate 610 (also referred to herein as a "filament wafer"), a second bottom wafer 620 (also referred to herein as a "capillary wafer"), and a third top wafer 630 (also referred to herein as a "capping wafer"). Although relative orientations are described as drawn (i.e., top, central and bottom), these orientations are intended for illustration purposes only, and should not be read as limiting on the scope of the invention. In fact, the orientation between top and bottom could be reversed, without change in the principle thereof. The first central laminate 610 comprises a first surface 611, a substantially parallel, opposing second surface 612, and a trench-shaped cavity formed in the first surface 611 and defining a bottom portion 516a of the detection cavity 516 (i.e., gas channel). Inlet port 512 and outlet port 514 are situated at opposing ends of the bottom portion 516a of the detection cavity 516, and extend from the detection cavity portion 516a through the central laminate 610 to the second surface 612 thereof. In preferred embodiments, and as shown, the inlet and outlet ports 512, 514 are defined by interior cylindrical walls that extend substantially normal to the second surface 612 of the central laminate 610. The first central laminate also includes the thin-film detection filament 520 and associated contacts 523, 524. The second bottom laminate 620 comprises a first surface 621, a substantially parallel, opposing second surface 622, and a pair of apertures—specifically first and second apertures 512', 514' in substantially alignment with the inlet and outlet ports 512, 514, respectively of the central laminate 610. When assembled, the first and second apertures 512', 514' are essentially an extension of the inlet port and outlet port 512, 514, respectively, and define interior cylindrical walls that extend substantially normal to the exposed, exterior second surface 622 of the bottom capillary laminate 620. For microfabricated microdetectors, the inlet and outlet ports 512, 514 of the microdetectors are preferably fabricated into the exterior surface of the substrate using a deep reactive ion etch process. The third top laminate 630 comprises a first surface 631, a substantially parallel, opposing second surface 632, and a trench-shaped cavity formed in the second surface 632 and defining a top portion 516b of the detection cavity 516 (i.e., gas channel). The top laminate 630 also includes a pair of contact apertures—specifically, first and second contact apertures 633, 634, such that the contact pads 523, 524 of the first surface 611 of the central laminate 610 are exposed and accessible for electrical connection (e.g. with pogo pins or other appropriate electrical contacting devices). The first, second and third laminates 610, 620, 630 can be bonded—with a high-temperature glue (e.g. epoxy or polyimide), via anodic bonding or via fusion bonding to form a unitary substrate 600 comprising the microdetector 510. The top and bottom portions 516b, 516a can be sized to form a detection cavity 516 having dimensions of about 6 mm long, about 1 mm wide and about 500 $\mu$m (about 0.5 mm) deep. Although illustrated for a single microdetector 510, a skilled artisan would readily appreciate that an array of microdetectors comprising four or more microdetectors could be integrally fabricated with a substrate substantially as described for the single microdetector case.

Advantageously, in one embodiment for providing flow to and from the microdetector, the first and second apertures 512', 514' of the bottom laminate 620 are sized to correspond to the outside diameter of a pair of capillaries—specifically a first inlet capillary 642 (e.g. in fluid communication with a gas chromatography column) and a second outlet capillary 644. The inlet capillary 642 and outlet capillary 644 can each be bonded (e.g. with a high-temperature glue such as an epoxy or polyimide, or anodically bonded or fusion bonded) to the first and second apertures 512', 514' of the bottom laminate 620, to create a macro-scale to micro-scale flow transition having substantially minimal, if any, dead volume. The bottom laminate 620 serves to support, as well as align the external capillaries 642, 644 to the inlet and outlet ports 612, 614, respectively, of the filament laminate 610.

Figure 6A:
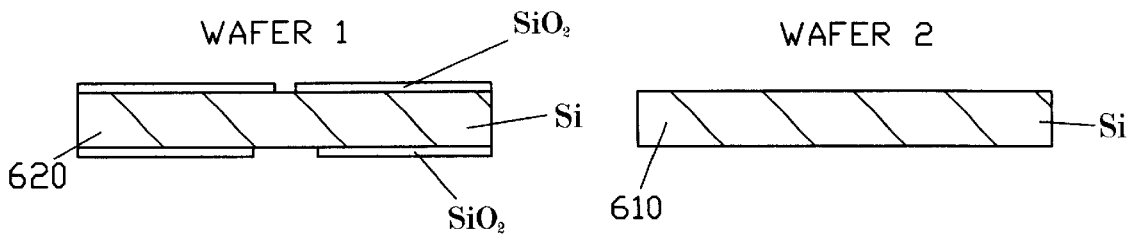
FIGS. 6A through 6P are schematic, cross-sectional views showing various stages of one microfabrication approach for forming a microfabricated detection cavity having a thin-film detection filament.
Figure 6B:
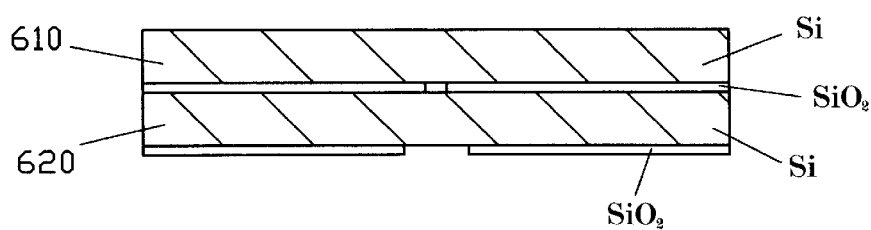
Figure 6C:
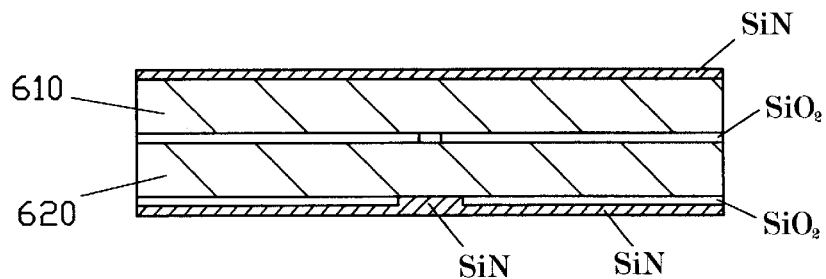
Figure 6D:
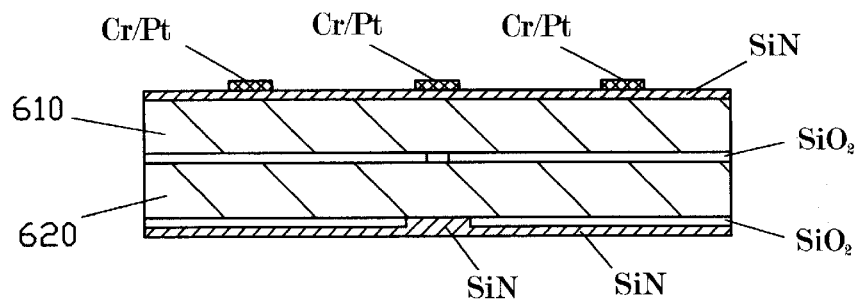
Figure 6E:
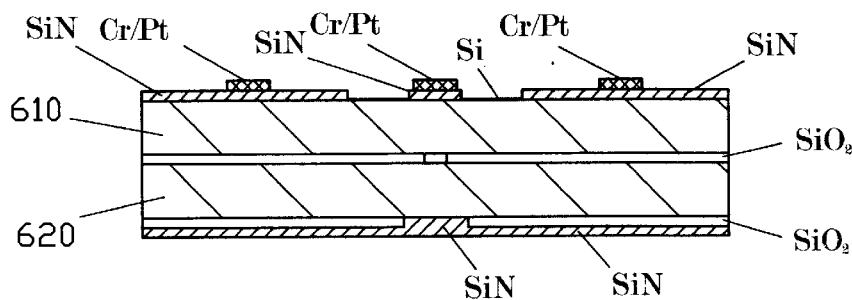
Figure 6F:
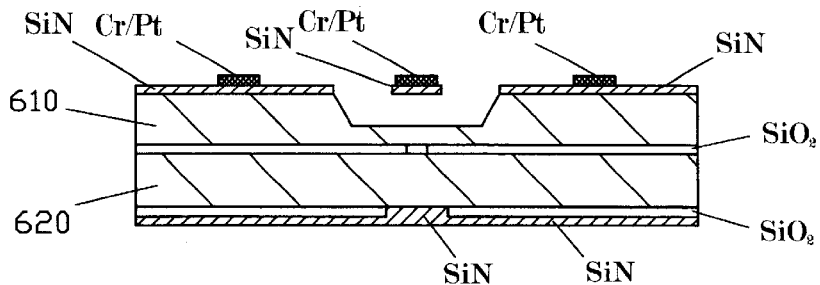
Figure 6G:
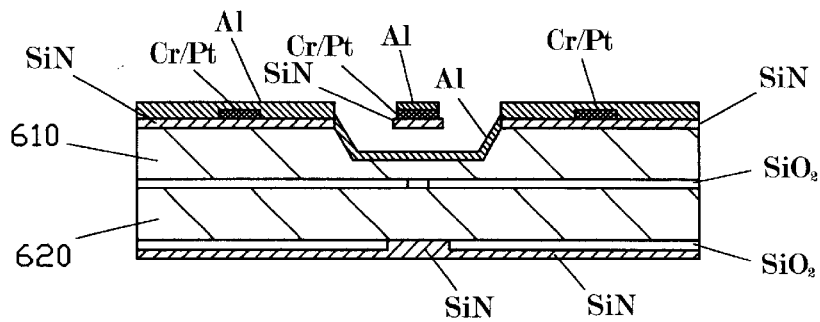
Figure 6H:
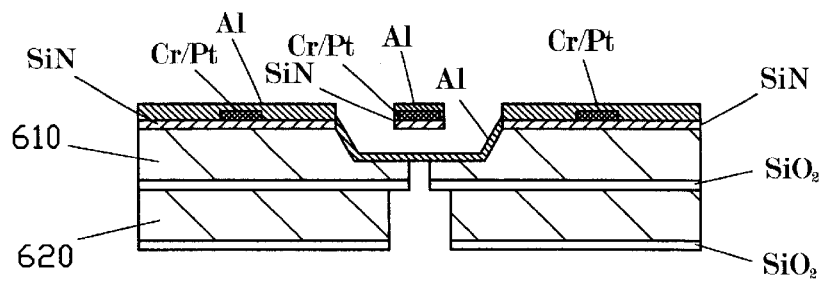
Figure 6I:
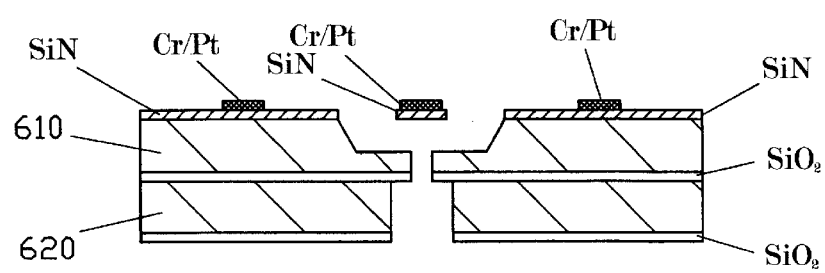
Figure 6J:
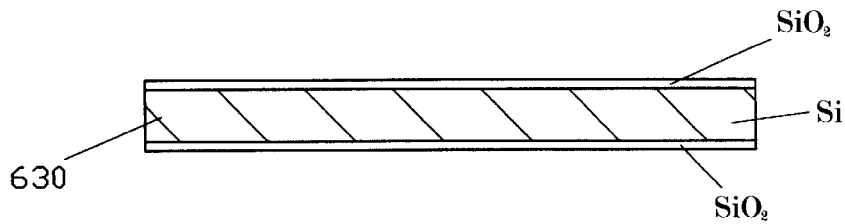
Figure 6K:
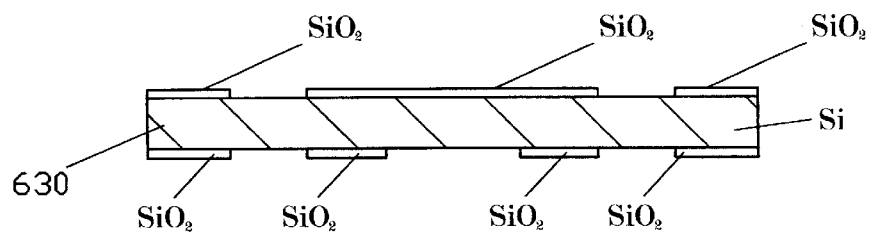
Figure 6L:
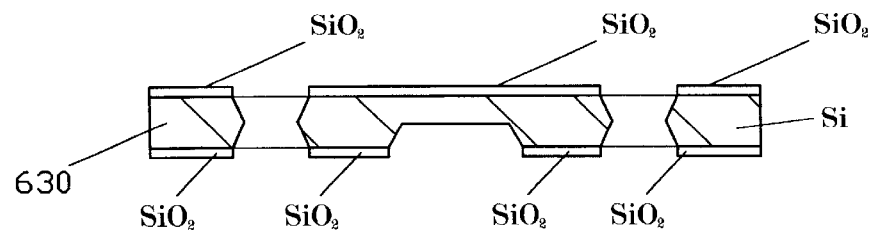
Figure 6M:
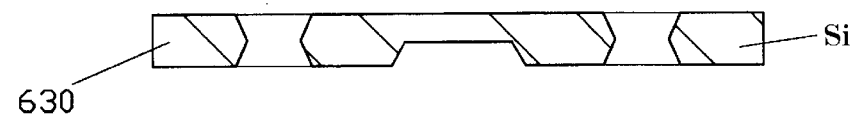
Figure 6N:
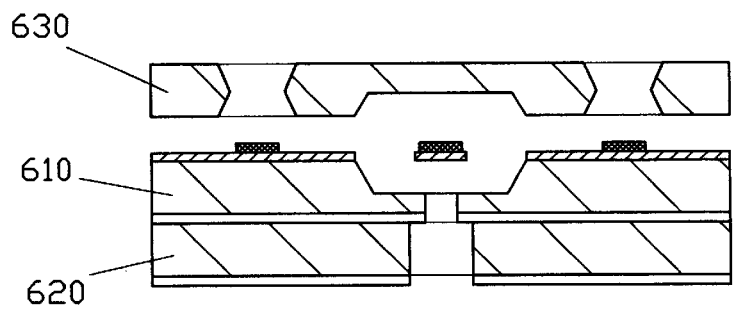
Figure 6O:
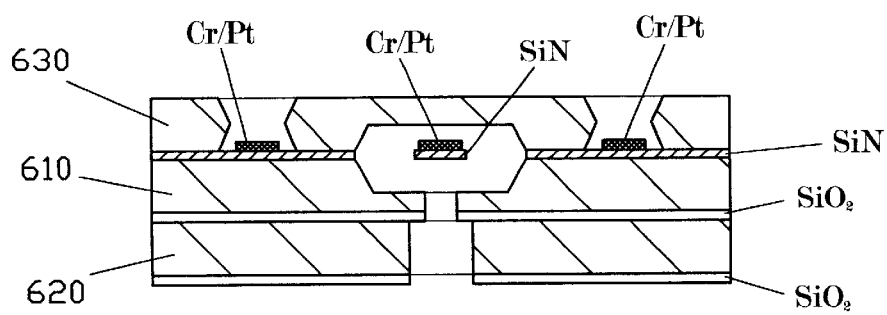
Figure 6P:
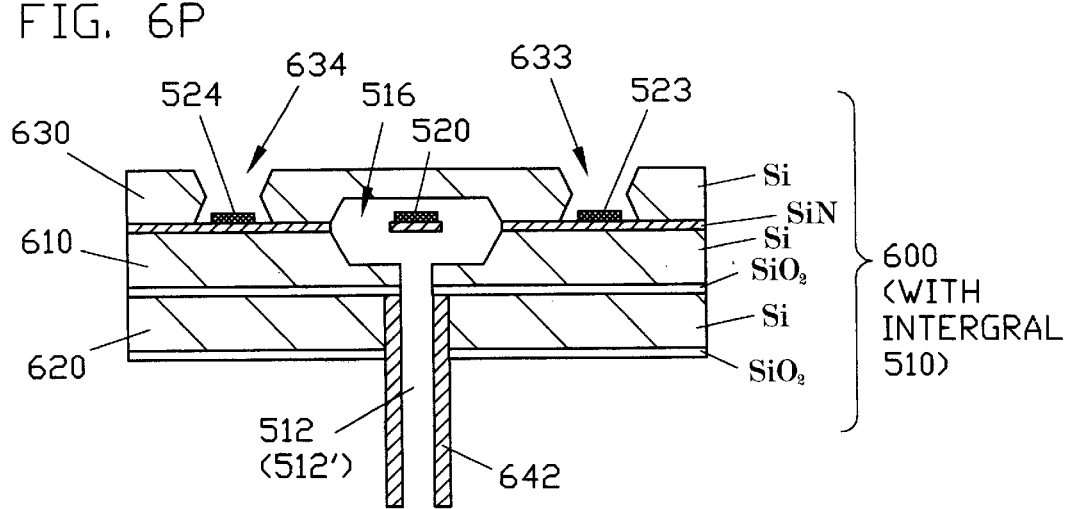

Example 1, together with FIGS. 6A through 6P, provides a more detailed description of exemplary microfabrication steps that can be used to form the microdetectors described in connection with FIGS. 5L and 5M in the immediately preceding two paragraphs.

In embodiments in which the four or more thermal conductivity microdetectors of the array are mounted on a substrate, the microdetectors are preferably integrally formed in a microchip body, and the microchip body is mounted on the substrate. The microchip body can comprise a single microdetector. Advantageously, individually-packaged microdetectors provides greater flexibility with respect to selecting appropriate microdetectors for inclusion into an array of microdetectors. For example, the performance characteristics (e.g., thermal coefficient of resistance, electrical resistance, leak testing) can be evaluated for each microdetector, and selection for inclusion into the array based on the results of the evaluation (e.g., including only microdetectors that satisfy performance specifications). Alternatively, a module of detectors comprising two or more detectors can be integral with a common microchip body.

The microchip body can generally be any body in which a thermal conductivity microdetector can be integrally formed, that is mountable on a substrate—either fixedly mounted or detachably mounted. Preferably, the microchip body has at least one mounting surface for mounting on a substrate, the mounting surface being adapted for reception with a corresponding mounting surface of the substrate. The microchip body is preferably a substantially planar body having at least two substantially parallel opposing surfaces. In some embodiments, the microchip body can be a plate-type substrate such as a wafer. The microchip body is preferably a micromachinable material (i.e., a material suitable for microfabrication techniques)—such as single crystal silicon. The microchip body material should generally be suitable for use under the conditions required in operation (e.g., with respect to temperature, etc.). Other suitable materials known in the art for integral microfabrication of thermal conductivity microdetectors (e.g. gallium arsenide, quartz, glass) can also be employed. The microchip body can advantageously comprise a plurality of laminae into which various components of the thermal conductivity microdetectors can be fabricated before assembly of the laminae to form the unified microchip body. The particular size of the microchip body is not narrowly critical, and will depend on design considerations and applications. including for example, the number of microdetectors (e.g. thermal conductivity detectors) integrally formed in the microchip body, required spacing between microdetectors (where the microchip body is a module comprising two or more microdetectors), etc. Typically, a microchip body of a plate-type (e.g., wafer) configuration and comprising a single microdetector integral therewith can range in size from about 10 cm$^2$ to about 1 mm$^2$ surface area, and from about 1 cm to about 100 µm (thickness). Preferred surface areas for a such a microchip body can range from about 5 cm$^2$ to about 2 mm$^2$, and from about 2 cm$^2$ to about 5 mm$^2$, with a most preferably surface area being about 1 cm$^2$. Preferably, the thickness can range from about 7 mm to about 200 µm, and from about 5 mm to about 500 µm, with a most preferred thickness of about 1 mm or about 2 mm. Typical and preferred sizes of a microchip body of a plate-type configuration that is mounted on the substrate as a module comprising two or more microdetectors can be the above-recited sizes multiplied by the number of microdetectors, with accounting for the required spacing between microdetectors. Preferred spatial densities of microdetectors on the microchip body is discussed below, in connection with the general case (i.e., whether integral with a substrate or with a microchip body).

The microchip body can also include one or more other structural features in addition to the structural features of the microdetector. For example, a thermal conductivity microdetector integral with microchip body can include (in addition to an inlet port, an outlet port, a detection cavity, a detection filament and optionally, contact pads and associated conductive paths) one or more integral temperature-measuring devices (e.g. thermocouples), active temperature-control devices (e.g. fluid-type heat exhangers), passive temperature-control devices (e.g. thermal insulating regions—such as between microdetctors), microfabricated valves, microfabricated pumps, microfabricated flow detectors, etc.

In some applications, however, the preferred microchip bodies of the invention consist essentially of one or more microdetectors—and have an essential substantial absence of other active microcomponents (but can include passive microcomponents such as flow channels, capillaries, thermal insulating regions, etc). Such microchip bodies with integral microdetectors advantageously allow for simplicity in design and fabrication, reduced manufacturing costs, greater modularity and associated operational flexibility. The substrate on which such microchip bodies can advantageously provide, in addition to a mechanical support for the microchip body, other integrated functionality such as flow distribution, temperature control, process monitoring, etc. Specifically preferred features are discussed in connection with the general substrate discription (above) and in connection with preferred embodiments with microchip bodies (below).

The microchip body can be mounted on the substrate—individually, or as one or more modules (with each module comprising two or more microdetectors)—by any suitable method. In some embodiments, the microchip body can be fixedly mounted by bonding an exposed mounting surface of the microchip body to an exposed mounting surface of the. The bonding can be chemical bonding using adhesives or glues, preferably high-temperature adhesives or glues such as epoxies or polyimides. Alternatively, the bonding can be anodic bonding, diffusion bonding, or other bonding methods known in the art or later developed. In other embodiments, the microchip body can be detachably mounted on the substrate. Preferably, in such embodiments, the microdetector array can further comprise one or more releasable films situated between the mounting surface of the substrate and the mounting surface of the microchip body. The releaseable film can advantageously be a releaseable seal, with dual functionality of providing releasability between the substrate and the microchip body, as well as providing a seal around component features providing fluid communication between the substrate and the microchip body (e.g., inlet and outlet flow paths in fluid communication therebetween). The releasable seal could include o-rings around flow conduits or one or more gaskets (substantially flat, typically flexible, sheets of sealing material). The releasable film can also provide other features, including for example, features affecting thermal conduction paths or electrical conduction paths, and as such, can be a releasable thermal insulator or a releasable electrical insulator.

Generally, the microchip body can comprise one or more microdetectors, preferably microfabricated microdetectors (e.g., thermal conductivity detectors). Microchip bodies comprising a single microdetector allows that microdetector to be individually mounted on the substrate. Advantageously, an array comprising individually mounted microdetectors affords significant flexibility with respect to tuning the array (e.g., in achieving a narrowly-confined range of sensitivities, as discussed below) for the application of interest. When the individually-mounted microdetectors are detachably mounted (rather than fixedly mounted), the array offers the further advantage of flexibility with respect to replacement of single microdectors. The microchip body can, however, also be a module comprising two or more microdetectors, preferably microfabricated microdetectors (e.g., thermal conductivity detectors). Modules can be advantageous applied, for example, to include dedicated reference microdetectors for each of the sample microdetectors.

Figure 7A:
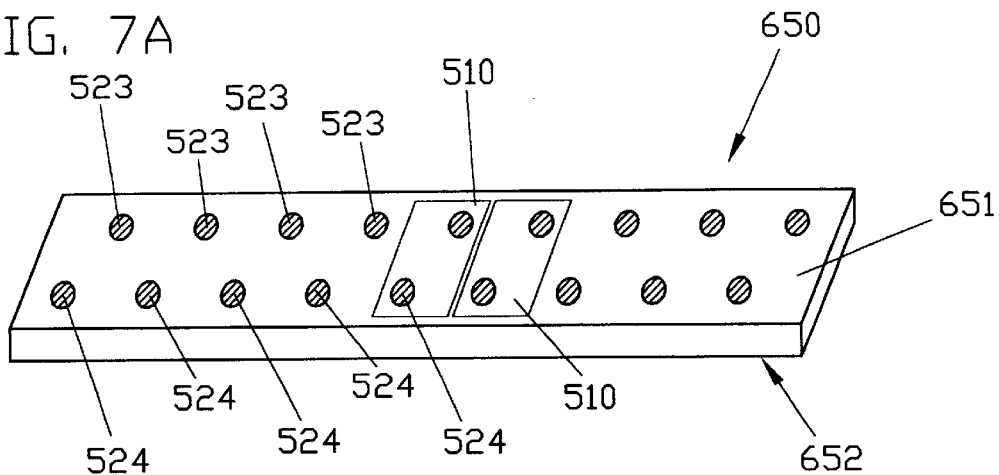
FIGS. 7A through 7K are perspective views (FIGS. 7A, 7B, 7C, 7D, 7G), exploded perspective views (FIGS. 7E, 7F, 7H, 7I) and cross-sectional views (FIGS. 7J, 7K) of a microchip body having one or more integral thermal conductivity microdetectors (FIGS. 7A, 7B, 7C, 7F, 7O), of a substrate on which the microchip body can be mounted (FIG. 7D), and of the substrate and mounted microchip body situated on a suppport frame for providing interfluidic connections, together with a printed circuit board assembly for associated electrical connections (FIGS. 7E, 7H, 7I, 7J, 7K).
Figure 7B:
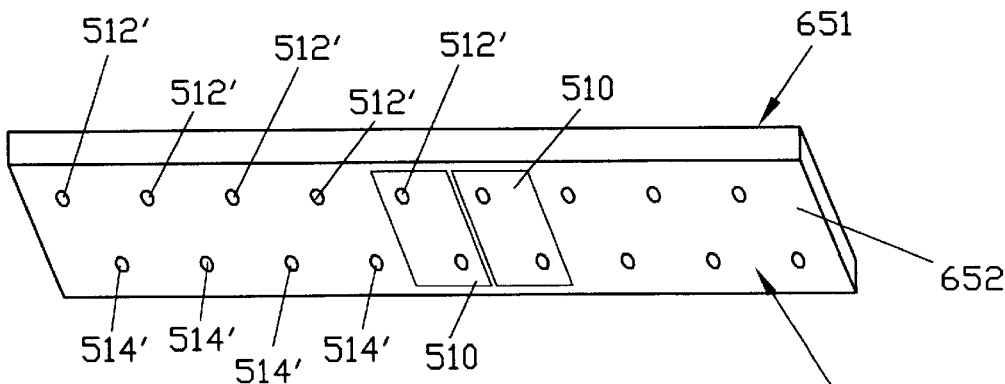
Figure 7C:
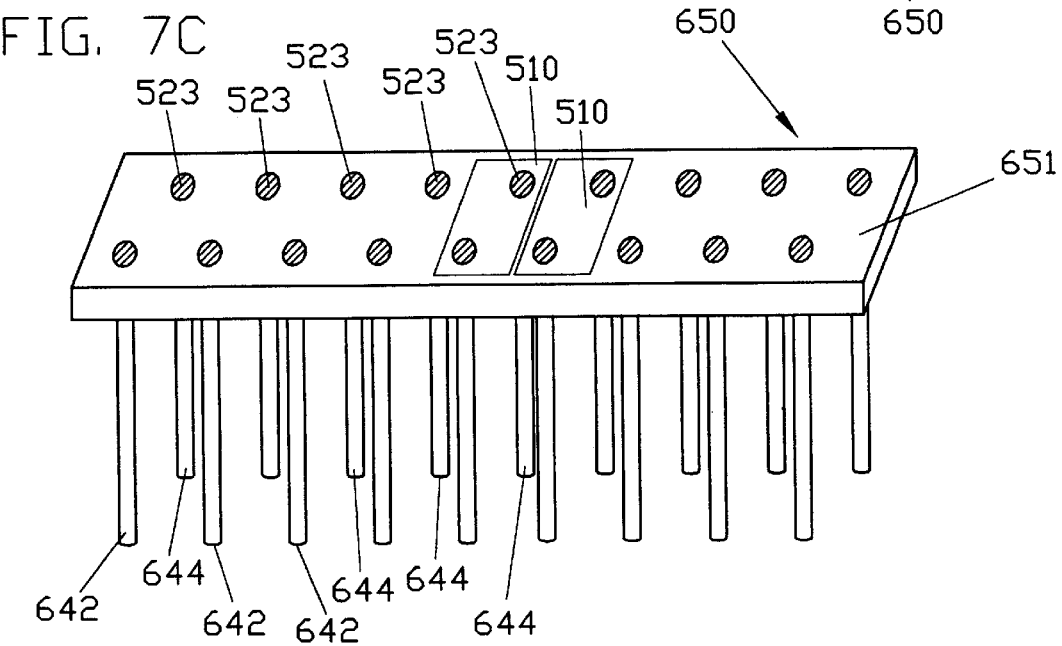

More specifically, with reference to FIGS. 7A through 7C, a microchip body 650 is illustrated as a module comprising nine thermal conductivity detectors 510 (dotted lines shown, for illustration purposes, to demarc regions containing individual thermal conductivity detectors). The microchip body 650 is a plate-type body having a substantially planar first surface 651 and a substantially parallel, opposing substantially planar second surface 652. Each thermal conductivity microdetector 510 comprises an inlet port 512', and outlet port 514', shown in FIG. 7B as pairs of apertures, each having an interior wall that is substantially normal to the second exterior surface 652 of the microchip body 650. Each TCD also comprises a detection cavity (interior to the microchip body, not shown), a detection filament (interior to the microchip body, not shown), a pair of first and second contact pads 523, 524 and a conductive path (interior to the microchip body, not shown) between the detection filament and the contacts 523, 524. In one embodiment, the microchip body 650 with integral thermal conductivity detectors 510 can be microfabricated from a plurality of laminae substantially as described in connection with FIGS. 5M and 5L and Example 1 (for the substrate with integral thermal conductivity microdetectors)—except that the laminae, once assembled, are used to form the unitary microchip body 650 rather than a unitary substrate 600. If desired, as shown in FIG. 7C, a first inlet capillary 642 and a second outlet capillary 644 can be bonded to the microchip body as described, to provide fluid communication with gas chromatography columns and exhaust manifolds, respectively.

Figure 7D:
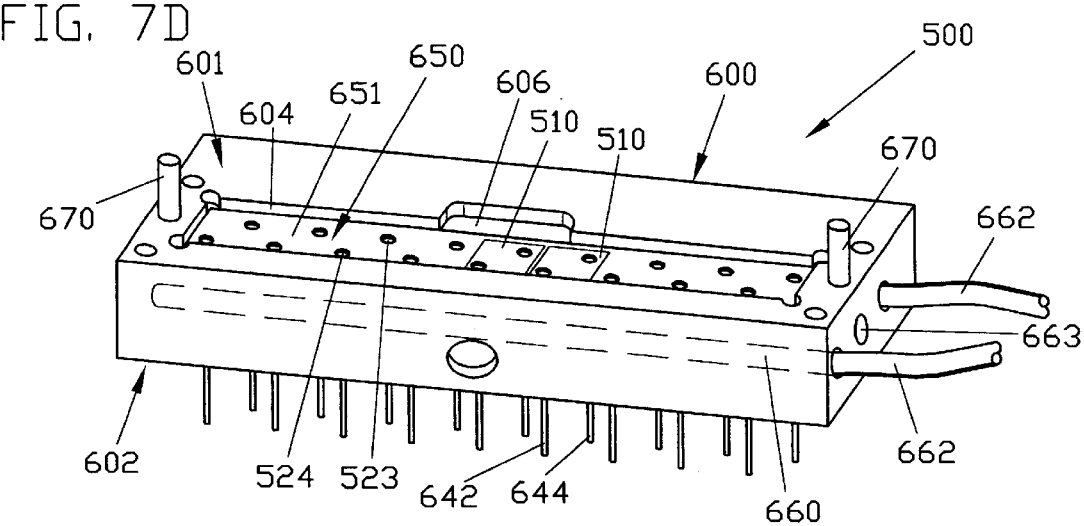

With reference to FIG. 7D, the microdetector array 500 comprises the microchip body 650 (as shown in FIG. 7C) mounted (either fixedly or detachably) onto a substrate 600, also referred to as a TCD array block. A second mounting surface 652 of the microchip body 650 is in contact with a mounting surface (not shown, under the microchip body 650, as illustrated) formed as a recessed region 604 in the exposed first surface 601 of the substrate 600. The recessed region 604, which can also be referred to as a TCD array slot, includes an access portion 606 to facilitate mounting and detaching of the microchip body 650 into the recessed region 604. The microchip body 650 comprises nine integral thermal conductivity microdetectors 510 (dotted lines shown, for illustration purposes, to demarc regions containing individual thermal conductivity detectors), with contacts 523, 524 at an exposed top surface 651 of the microchip body 650. As illustrated, nine pairs of capillaries, each pair including a first inlet capillary 642 and a second outlet capillary 644 extend downward from the microchip body 650 through nine pairs of passages (not shown) formed in the substrate 600. Because each of the capillaries 642, 644 are bonded directly to the microchip body 650 and thereby form a hydraulic seal (with little, if any dead volume), the microchip body 650 can be mounted on the substrate 600 without a releasable seal between the second mounting surface 652 of the microchip body 650 and the mounting surface of the recessed region 604 of the substrate 600. If desired however, a releasable film may be situated therebetween to facilitate detachment. Alternatively, if a variation on this embodiment (not illustrated in FIG. 7D), the microchip body 650 could be fabricated without the capillaries 642, 644, and the pairs of flow passages in the substrate 600 could be sealed in fluid communication with the inlet and outlet ports 512', 514' of the microchip body using a releasable seal such as individual o-rings at each connection, or one or more gaskets. As shown, the substrate 600 also comprises two resistive cartridge heaters 660 (one shown, with dotted lines to indicate position internal to the substrate) integral therewith, with heater wires 662 extending from the substrate 600. A thermocouple can be included in the substrate, for example, via thermocouple aperture 663. Alignment pins 670 can be used to align the microdetctor array 500 into a gas chromatograph system, as described below.

Figure 7E:
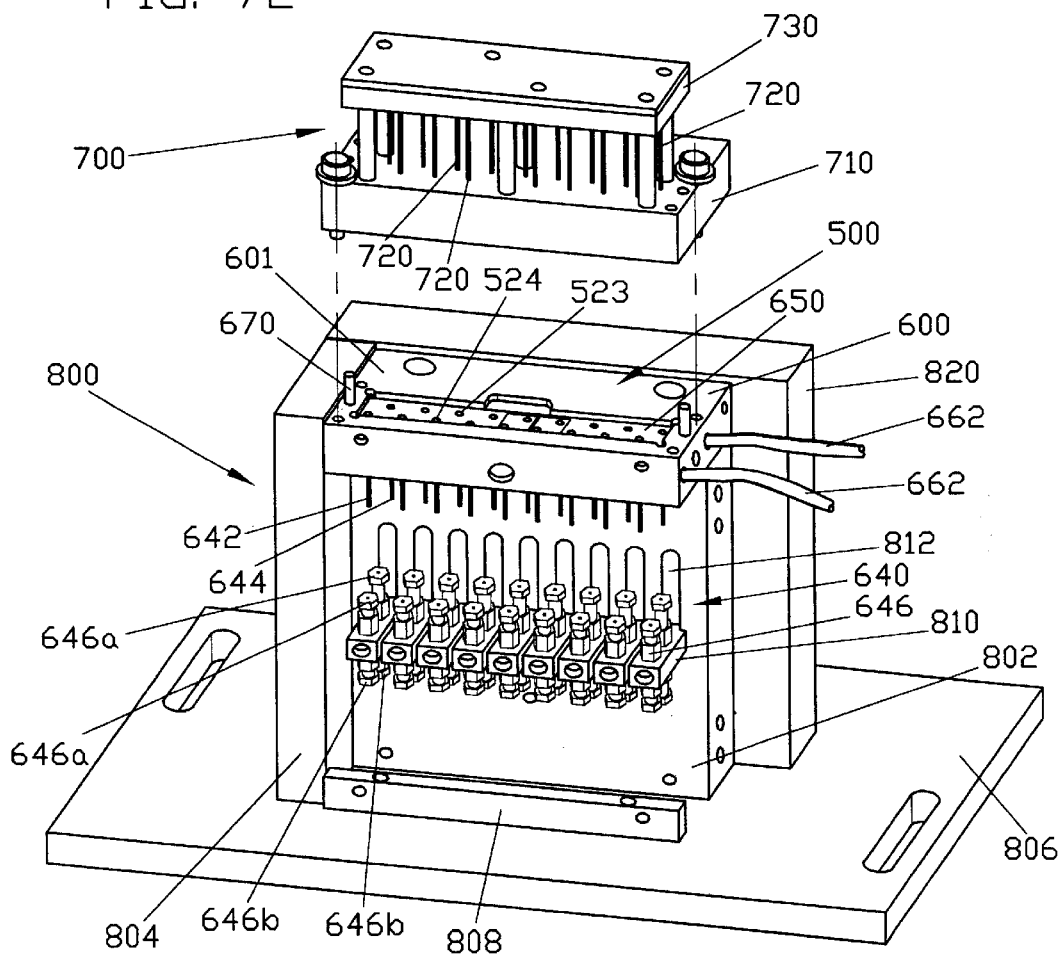

FIG. 7E shows the microdetector array 500 in a support frame 800 that provides structural support for fluidic interconnection components (indicated generally at 640)—for connecting the microdetector array 500 to conventional, macroscale gas chromatography columns (not shown), as well as for electrical connection components (indicated generally at 700) for coupling the thermal conductivity detectors 510 to one or more detection circuits. Briefly, the support frame 800 comprises a side wall 802, and an end wall 804 substantially perpendicular to the side wall 802, each being secured to a platform 806. A relatively short front wall 808 provides further support to the end wall 804. The side wall 802 and end wall 804 can be of any suitable material, including an insulating material. Additionally or alternatively, insulation 820 can be provided adjacent to the side wall 802 and/or the end wall 804. The microdetector array 500 and fluidic interconnection components 640 can each be fastened to the side wall 802. The microdetector array 500 comprises a module of nine thermal conductivity detectors 510 integral with a microchip body 650 mounted on substrate 600. (Further details are described above in connection with FIG. 7D). Fluidic connections to the gas chromatography (GC) columns can be provided by nine commercial, zero-dead-volume unions 646 (Valveco), each union having an upper portion 646a and a lower portion 646b. Stainless steel capillaries (not shown) coming from the GC columns can be connected into the lower portion 646b of the unions 646 (front row, as illustrated) and the nine fused silica inlet capillaries 642 can be connected to the upper portion 646a of the unions 646. Likewise, the nine outlet capillaries 644 can be connected to the upper portion 646 of nine unions 646 (back row, as illustrated), with exhaust capillaries (e.g., stainless steel) being connected to the lower portion 646b of the unions 646. The pairs of unions 646 can be independently positioned using the slider 810 that is movably fastened to slider slots 812 in the side-wall 802 of the support frame 800. The ability to position the unions independently is advantageous because the capillary interconnects 642, 644 can be of slightly different lengths. Each slider 810 has two hexagonal holes for the pair of zero-dead-volume unions 646, one each for the inlet capillary 642 and outlet capillaries 644 of each TCD 510. Each union 646 in a single slider 810 can also be separately positioned using set-screws (not shown). As discussed above, the TCD array 500 comprises the microchip body 650 seated on the heated block substrate 600, which is bolted to the sidewall 802. The electrical connection components 700 can be secured to the top exposed surface 601 of the substrate 600. Specifically, a printed circuit board (PCB) 730 comprising the required electronics (i.e., with one or more external signal-processing circuits) is electrically connected to the contact pads 523, 524 of the thermal conductivity detectors 510 of the TCD array 500 using pogo-pins 720 extending downward through a printed-circuit-board block 710 (PCB block) that provides structural support for the pogo-pins 720, as well as thermal isolation for the PCB 730. As such, the PCB block 710 is preferably constructed using a high-temperature thermally and electrically insulating material.

In an alternative embodiment, the microdetector array can comprise four or more microdetectors in separate microchip bodies that are individually mounted on a substrate. The separate microchip bodies, each comprising a single integral microdetector can be formed separately, but are preferably formed collectively on a common wafer using batch microfabrication, and subsequently divided into separate microchip bodies as is common in the microfabrication art for circuit board components and other microfabricated devices. Hence, although fabrication is described herein in connection with a single microdetector, a skilled artisan would appreciate that the methods described herein could be applied to manufacture a large number of microdectectors on a common wafer.

Figure 7F:
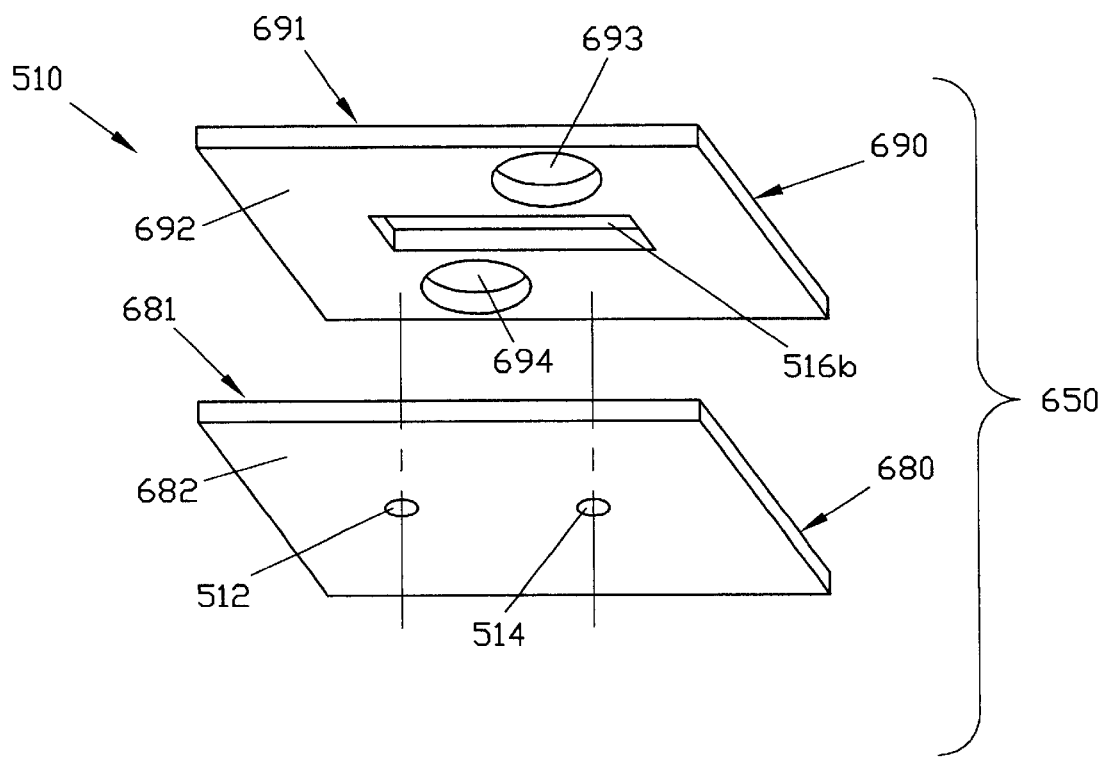
Figure 7G:
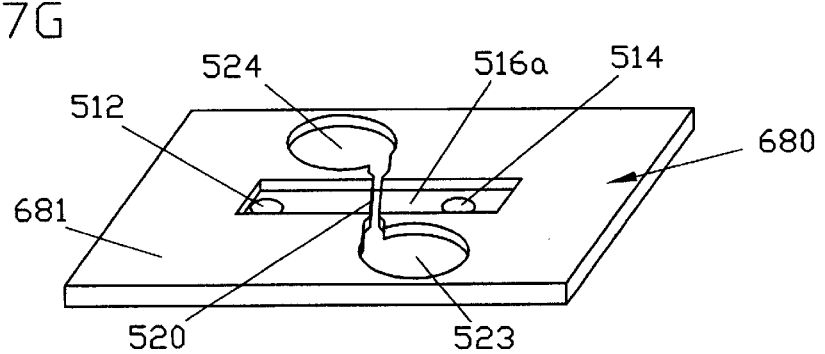
Figure 7H:
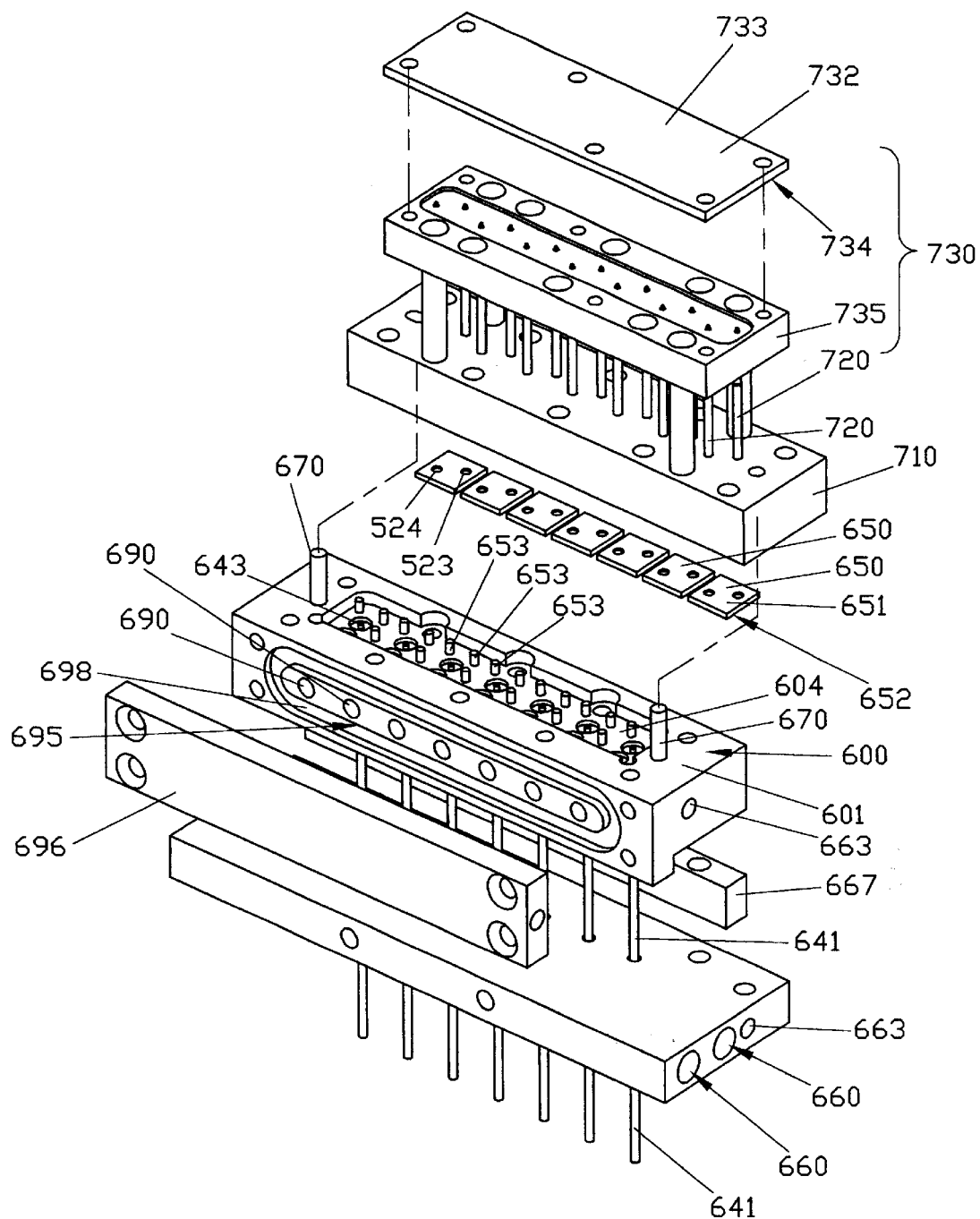
Figure 7I:
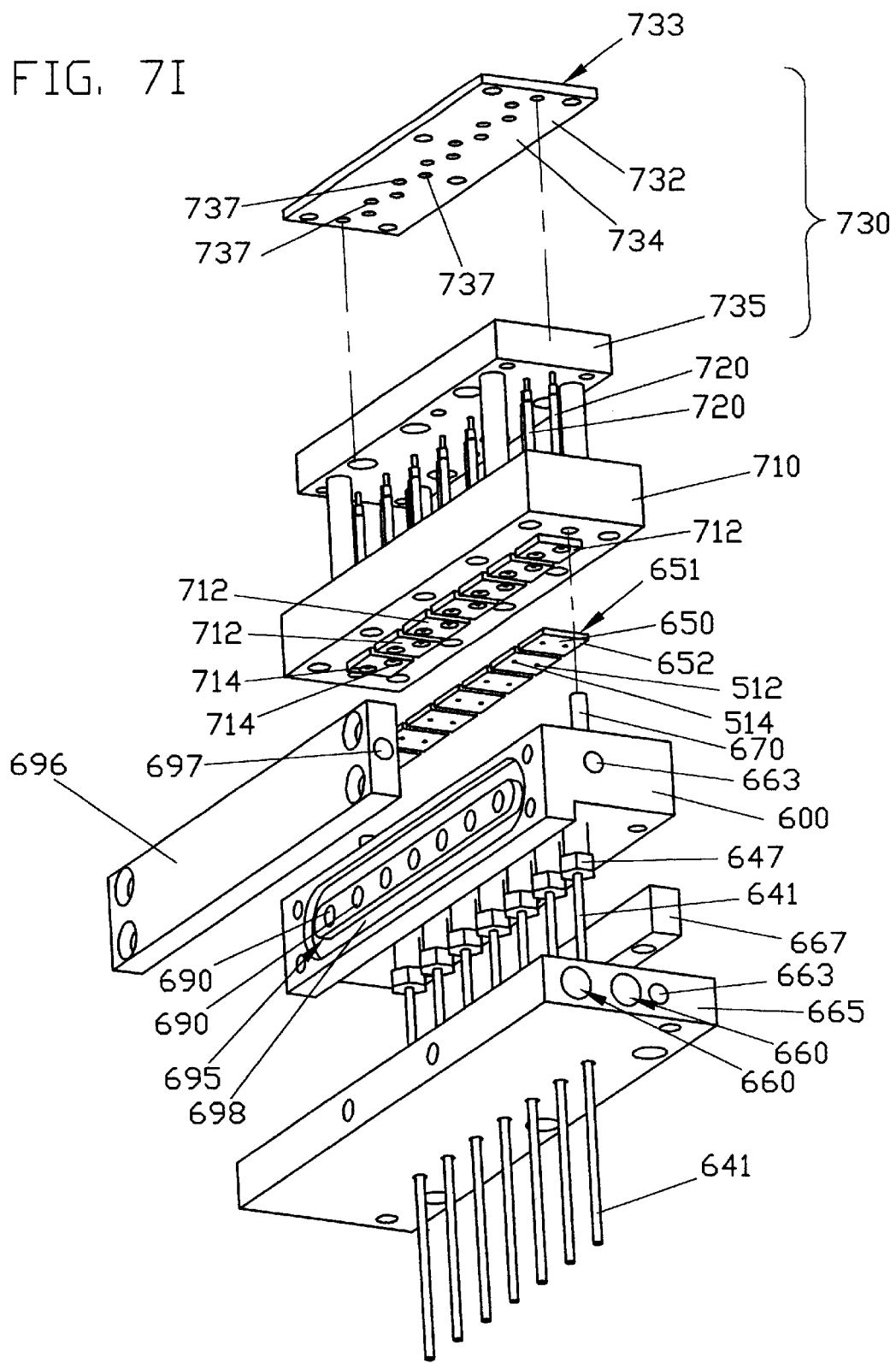
Figure 7J:
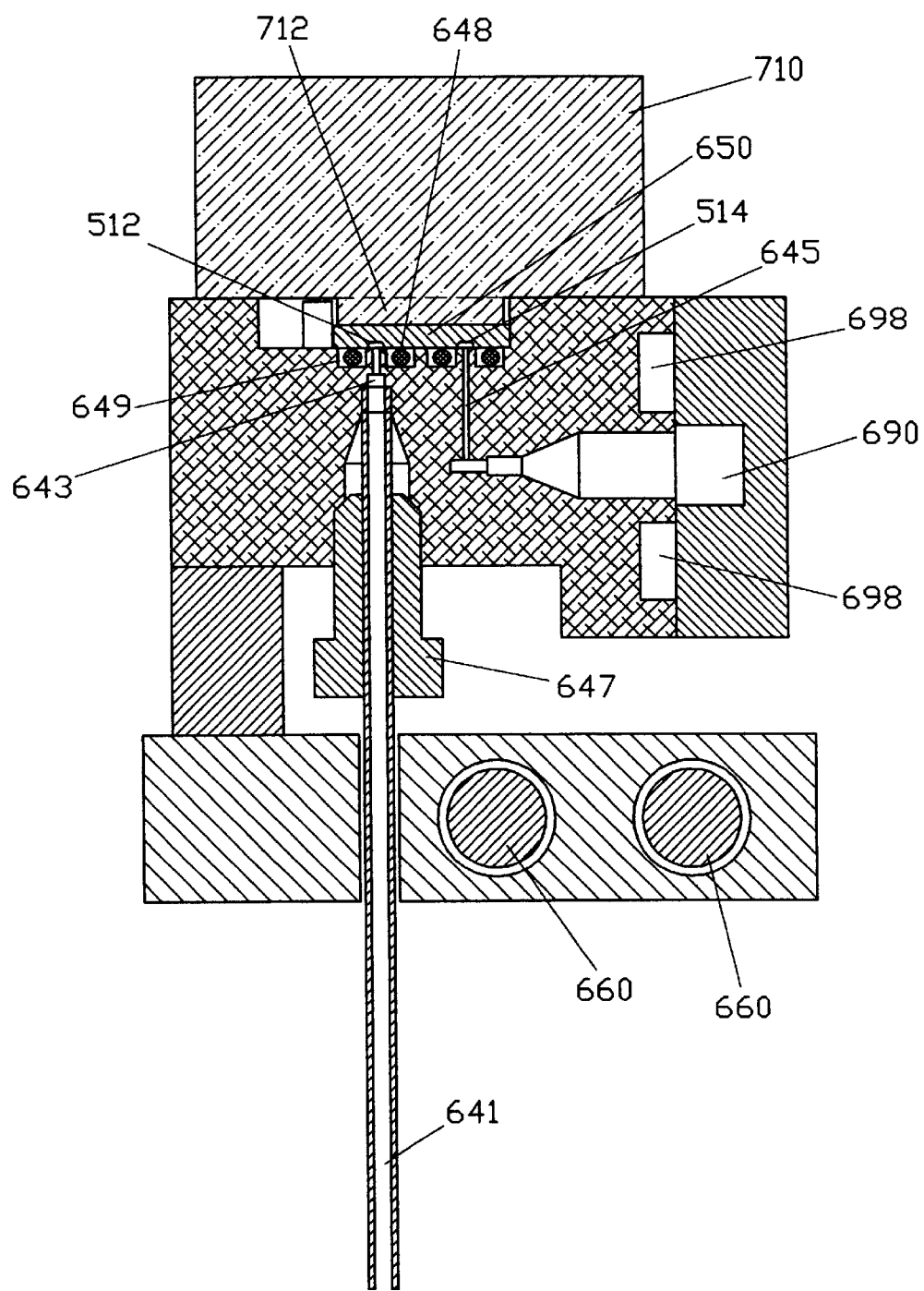
Figure 7K:
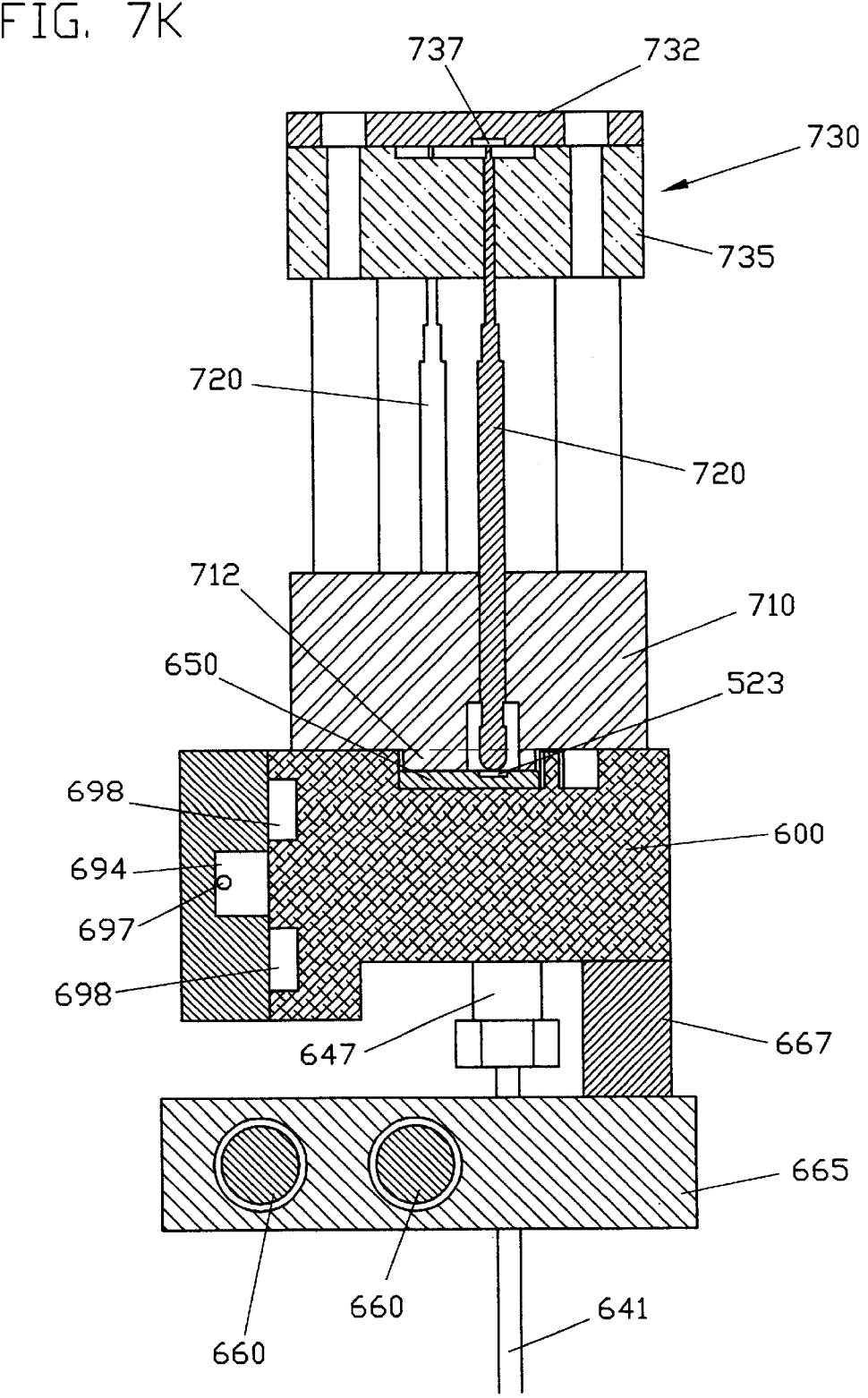

With reference to FIGS. 7F and 7G, for example (showing a single thermal conductivity microdetector, for simplicity of illustration), a thermal conductivity microdetector 510 can be integrally microfabricated with a microchip body 650 comprising a first bottom laminate 680 (also referred to herein as a "filament wafer") and a second top wafer 690 (also referred to herein as a "capping wafer"). Although relative orientations are described as drawn (i.e., top, central and bottom), these orientations are intended for illustration purposes only, and should not be read as limiting on the scope of the invention. In fact, the orientation between top and bottom could be reversed, without change in the principle thereof. The first bottom laminate 680 comprises a first surface 681, a substantially parallel, opposing second surface 682, and a trench-shaped cavity formed in the first surface 681 and defining a bottom portion 516*a* of the detection cavity 516 (i.e., gas channel). Inlet port 512 and outlet port 514 are situated at opposing ends of the bottom portion 516*a* of the detection cavity 516, and extend from the detection cavity portion 516*a* through the filament laminate 680 to the second surface 682 thereof. In preferred embodiments, and as shown, the inlet and outlet ports 512, 514 are defined by interior cylindrical walls that extend substantially normal to the second surface 682 of the bottom laminate 680. The first bottom laminate 680 also includes the thin-film detection filament 520 and associated contacts 523, 524. The second top laminate 690 comprises a first surface 691, a substantially parallel, opposing second surface 692, and a trench-shaped cavity formed in the second surface 692 and defining a top portion 516*b* of the detection cavity 516 (i.e., gas channel). The top laminate 690 also includes a pair of contact apertures—specifically, first and second contact apertures 693, 694, such that the contact pads 523, 524 of the first surface 681 of the bottom laminate 680 are exposed and accessible for electrical connection (e.g. with pogo pins or other appropriate electrical contacting devices). The first and second laminates 680, 690 can be bonded (as described above) to form to form a unitary microchip body 650 comprising the microdetector 510.

Example 2, together with FIGS. 10A through 10E, provides a more detailed description of exemplary microfabrication of microchip bodies with integral microdetectors as described in connection with FIGS. 7F and 7G in the immediately preceding paragraph.

Referring now to FIGS. 7H through 7K, a microdetector array comprises seven microchip bodies 650 individually, and detachably mounted on the substrate 600, with each of the seven microchip bodies comprising an integral thermal conductivity detector (e.g., as shown as microdetector 510 in FIGS. 7F and 7G, and as described in connection therewith). Each of the microchip bodies 650 are plate-type bodies having a substantially planar first surface 651 and a substantially parallel, opposing substantially planar second surface 652. A second mounting surface 652 of each of the microchip bodies 650 is in contact with a mounting surface formed as a recessed region 604 in the exposed first surface 601 of the substrate 600. Alignment pins 653 can help for positioning of the microchip bodies 650 during mounting. When assembled, the microchip bodies 650 are releasably held in the mounting position by islands 712 formed in the bottom surface of the PCB block 710. As shown, the microchip bodies 650 comprise contacts 523, 524 (FIG. 7H) at an exposed top surface 651 of the microchip bodies 650, and inlet and outlet ports 512, 514 (FIG. 7I) at the bottom mounting surface 652 of the microchip bodies.

Fluidic connections to the gas chromatography columns can be advantageously effected as follows. The inlet port 512 (FIG. 7I) of each of the microchip bodies 650 is in fluid communication with a first inlet passage 643 in the substrate 600. Similarly, the outlet port 514 (FIG. 7I) of each of the microchip bodies 650 is in fluid communication with a second outlet passage 645 in the substrate 600. The substrate comprises seven pairs of such passages 643, 645, one for each of the thermal conductivity microdetectors. As shown in greater detail in FIG. 7J, the pairs of flow passages 643, 645 in the substrate 600 are individually sealed in fluid communication with the inlet and outlet ports 512, 514 of the microchip bodies using individual o-rings 648 as a releasable seal. The o-rings are seated in recessed o-ring seats 649 that are formed in the mounting surface 604 of the substrate 600. One or more gaskets could be used alternatively, instead of the o-ring seals. In a preferred embodiment at least one of the inlet and outlet passages 643, 645, and preferably the inlet passage 643 extends downward from the first mounting surface 604 of the substrate 600 to a second surface 602 of the substrate. The second surface 602 may be an irregular surface, with some portion interior to the bulk of the substrate 600, to accommodate a fitting 647, such as a conventional fitting (e.g. Valveco fitting) that provides fluid communication between the first inlet passage 643 and a capillary 641 (e.g., stainless steel capillaries, ⅟₁₆") from the gas chromatography columns. The outlet passage 645 can extend downward, and then to the side of the substrate 600, as shown, to provide fluid communication with individual exhaust ports 690, optionally in fluid communication with a common exhaust manifold 695. As illustrated, the exhaust manifold 695 can be defined by a circumferential recess 698 formed in the side of the substrate 600, together with exhaust capping plate 696, having recessed groove 694 providing common fluid communication with and between each of the exhaust ports 690. The capping plate 696 can be sealed against the substrate using a gasket (not shown). The exhaust manifold 695 can have a common exhaust port 697 formed in the capping plate 696 (as shown) or in the substrate (not shown).

Temperature control of the microdetector array 500 can be acheived as described above in connection with FIGS. 7D and 7E. Alternatively, and preferably, however, temperature control is effected using a thermal damping configuration in which the heat source is isolated from the substrate (rather in direct contact therewith) such that heat flows to the substrate via conduction, with a larger thermal time constant for a given step change in temperature. As shown in FIGS. 7H through 7K, for example, a heating block 665 can comprise one or more resistive heaters, such as a pair of cartridge heaters 660, and a thermocouple 663. Heat is conducted from the heating block 665 to the substrate 600 via conduction block 667. Using such arrangements, the thermal excursion associated with a step change in heat source temperature is substantially dampened in the substrate 600, thereby improving the performance of the array of thermal conductivity microdetectors 510. Regardless of the particular temperature-control system, the temperature as measured across the array of microdetectors (e.g., thermal conductivity detectors) is preferably controlled to vary not more than about 10° C. Preferably, the variation in temperature across the array is not more than about 5° C., more preferably not more than about 2° C., still more preferably not more than about 1° C., and most preferably not more than about 0.5° C. As discussed above, rapid thermal excursions (temperature variations over time) are preferably minimized, or at least controlled across the array to be not less than about 0.5° C./minute. The rate of heating or cooling across the microdetector array is preferably controlled to be not less than about 1° C./minute, and more preferably not less than about 5° C./minute. Stated in another manner, the thermal excursions can be characterized by a time constant for the array, as determined by measuring the time required to achieve 90% of the steady state temperature following a step change in the temperature of the heating source. The characteristic time constant, as so measured, is preferably not less than about 30 seconds, preferably not less than about 1 minute, more preferably not less than about 2 minutes, and most preferably not less than about 5 minutes.

The electrical connection components 700 can be secured to the top exposed surface 601 of the substrate 600, substantially as described in connection with FIG. 7D. Specifically, with general reference to FIGS. 7H and 7I, and with particular reference to FIG. 7K, a printed circuit board (PCB) 730 can comprise the required electronics (i.e., can have one or more signal-processing circuits) or can provide connection paths to such external signal-processing circuits (e.g., via edge-connections). To improve sensitivity, the signal processing circuits preferably comprise low-noise components, and are preferably located in near proximity to the detectors. The printed circuit board 730 can include a circuit card 732 having a first upper surface 733 and a second lower surface 734, and being supported on a card support block 735. The second lower surface 734 of the circuit card can include a plurality of contacts 737 to provide electrical connection with the pogo-pins 720. Each of the contacts 737 of the printed circuit card 732 is electrically connected to the contact pads 523, 524 of the thermal conductivity detectors 510 of the TCD array 500, using pogo-pins 720 extending downward through a printed-circuit-board block 710 (PCB block) that provides structural support for the pogo-pins 720, as well as thermal isolation for the PCB 730. As such, the PCB block 710 is preferably constructed using a high-temperature thermally and electrically insulating material. As noted, the PCB block 710 preferably comprises islands 712 for detachably mounting the microchip bodies 650 onto the substrate 600. The islands are configured, in shape, to correspond to the configuration of the array of microchip bodies (shown in the figures as a linear array). Each of the islands 712 includes a pair of apertures to allow the pogo-pins 720 to pass through to access the contact pads 523, 524 of the thermal conductivity microdetectors.

The microdetector arrays of the invention, for each of the general and specific embodiments as variously characterized above, preferably comprises six or more microdetectors (e.g., thermal conductivity detectors), more preferably ten or more detectors, and most preferably twenty or more detectors. Higher numbers of microdetectors can be formed (in a common substrate or microchip bodies, or in separate microchip bodies), including for example forty or more, sixty or more, eighty or more, one-hundred or more, two-hundred or more, four hundred or more or one-thousand or more. In some embodiments, the number of microdetectors (e.g., thermal conductivity detectors) in the array can be 96×N, where N ranges from 1 to about 100, more preferably from 1 to about 10, and most preferably from 1 to about 5.

The particular arrangement of the four or more microdetectors in the array is not critical. Although described primarily herein as linearly-arranged arrays of microdetectors, other arrangements, such as rectilinear or radial two-dimensional arrays are contemplated. The array of microdetectors can also be configured as a three dimensional array, with various microdetectors at different x, y, z coordinates relative to each other. Regardless of the particular configuration, the microdetector array can be further characterized with respect spatial (e.g., planar) density of the microdetectors as configured in the array. The array can be configured, for example, to include the four or more microdetectors (e.g. thermal conductivity detectors) arranged to have a spatial (e.g., planar) density of at least about 1 thermal conductivity detector per 10 cm$^2$. The spatial (e.g., planar) density of the four or more microdetectors (e.g. thermal conductivity detectors) is preferably at least about 1 TCD/5 cm$^2$, more preferably at least about 1 TCD/2 cm$^2$, even more preferably at least about 1 TCD/1.5 cm$^2$, and still more preferably at least about 1 TCD/cm$^2$. In some applications, even higher spatial densities are advantageous, including for example, 2 TCD's/cm$^2$, 5 TCD's/cm$^2$ or 10 TCD's/cm$^2$.

The microdetector array can, in each of the embodiments (general and specific) further comprise at least one reference thermal conductivity detector. The at least one reference detector can be substantially the same as a sample detector, except that it has an inlet port in fluid communication with a reference gas source for receiving a reference gas. For a thermal conductivity reference detector, the microdetector also comprises a detection cavity comprising a thin-film detection filament within the detection cavity for detecting the reference gas, and an outlet port for discharging the detected reference gas. The ratio of the number of gaseous sample detectors to the number of reference detector(s) is preferably at least 2:1. Advantageously, the ratio of sample detectors to reference detectors can also be higher, including for example 3:1, 4:1, 5:1, 7:1, 10:1, about 20:1, about 40:1, about 70:1, about 100:1, or higher, depending on the particular application.

The array of microdetectors (e.g. thermal conductivity microdetectors) is further characterized (for all of its embodiments) with regard to uniformity in performance characteristics as compared between the different (four or more) channels of the array. In general, for example, the four or more microdetectors each have a sensitivity for detecting a component of interest, with the sensitivity varying less than about 10% between the four or more microdetectors. For thermal conductivity detectors, in particular, the four or more thermal conductivity detectors each preferably have a thermal coefficient of resistance that varies less than about 10% between the four or more thermal conductivity detectors. The variation in thermal coefficient of resistance between the four or more thermal conductivity detectors is preferably less than about 5%, more preferably less than about 3%, even more preferably less than about 2%, still more preferably less than about 1%, and most preferably less than about 0.5%. Additionally, or alternatively, the detection filament of each of the four or more thermal conductivity detectors preferably has a resistance that varies less than about 25% between the four or more thermal conductivity detectors. The variation in resistance between the detection filament of the four or more thermal conductivity detectors is preferably less than about 20%, more preferably less than about 15%, even more preferably less than about 10%, still more preferably less than about 7%, and most preferably less than about 5%.

Figure 8A:
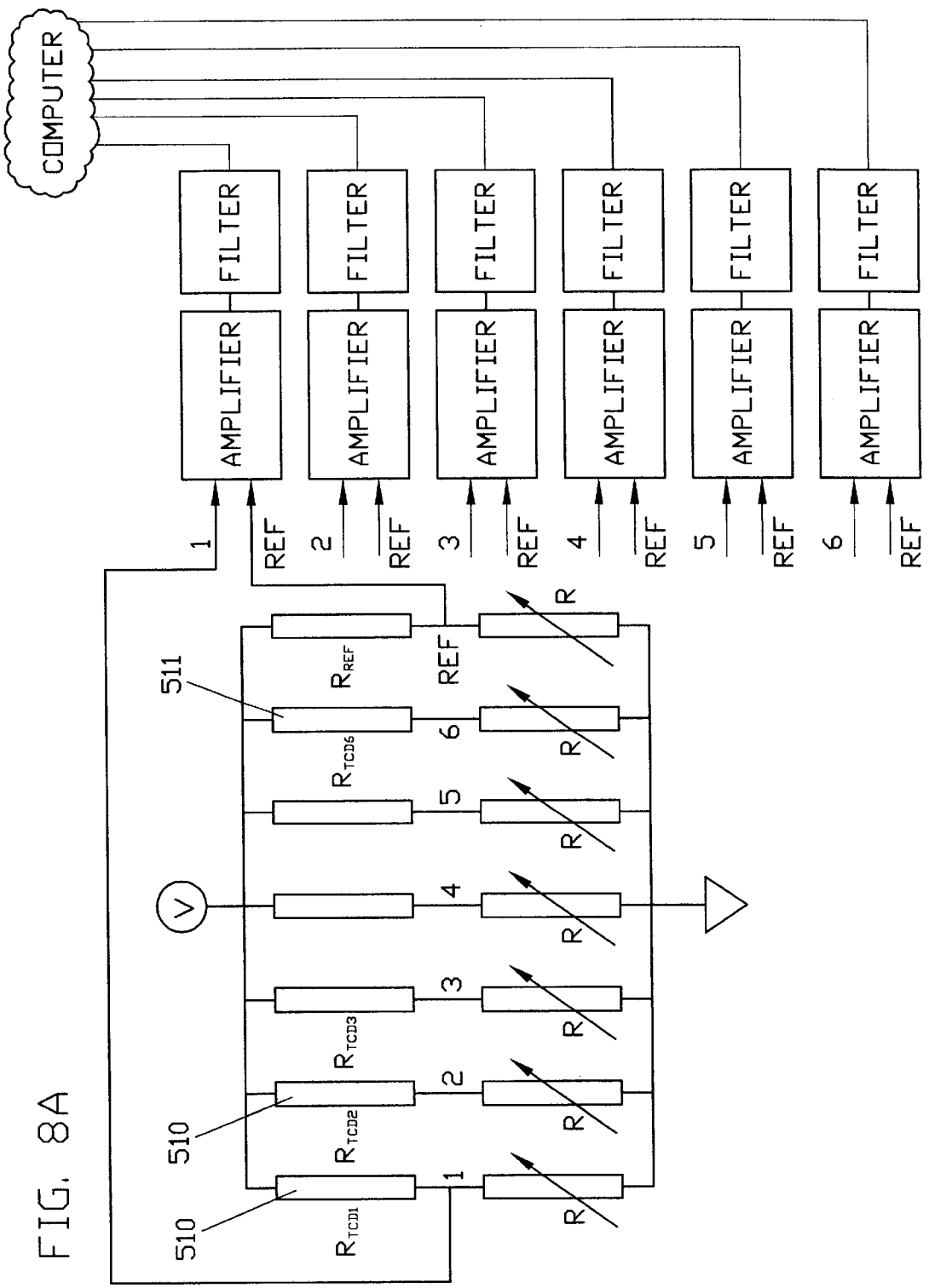
Figure 8C:
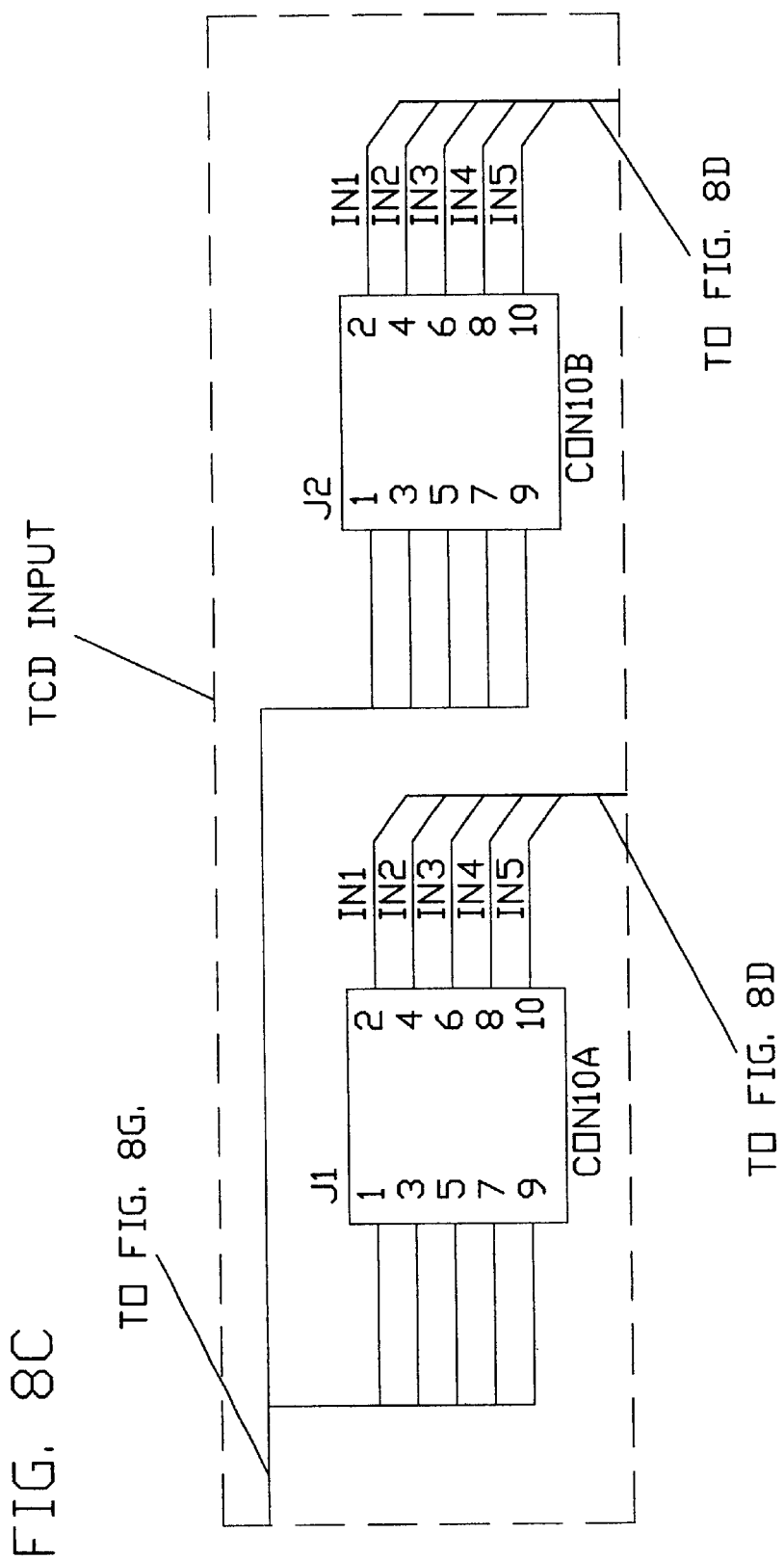
Figure 8D:
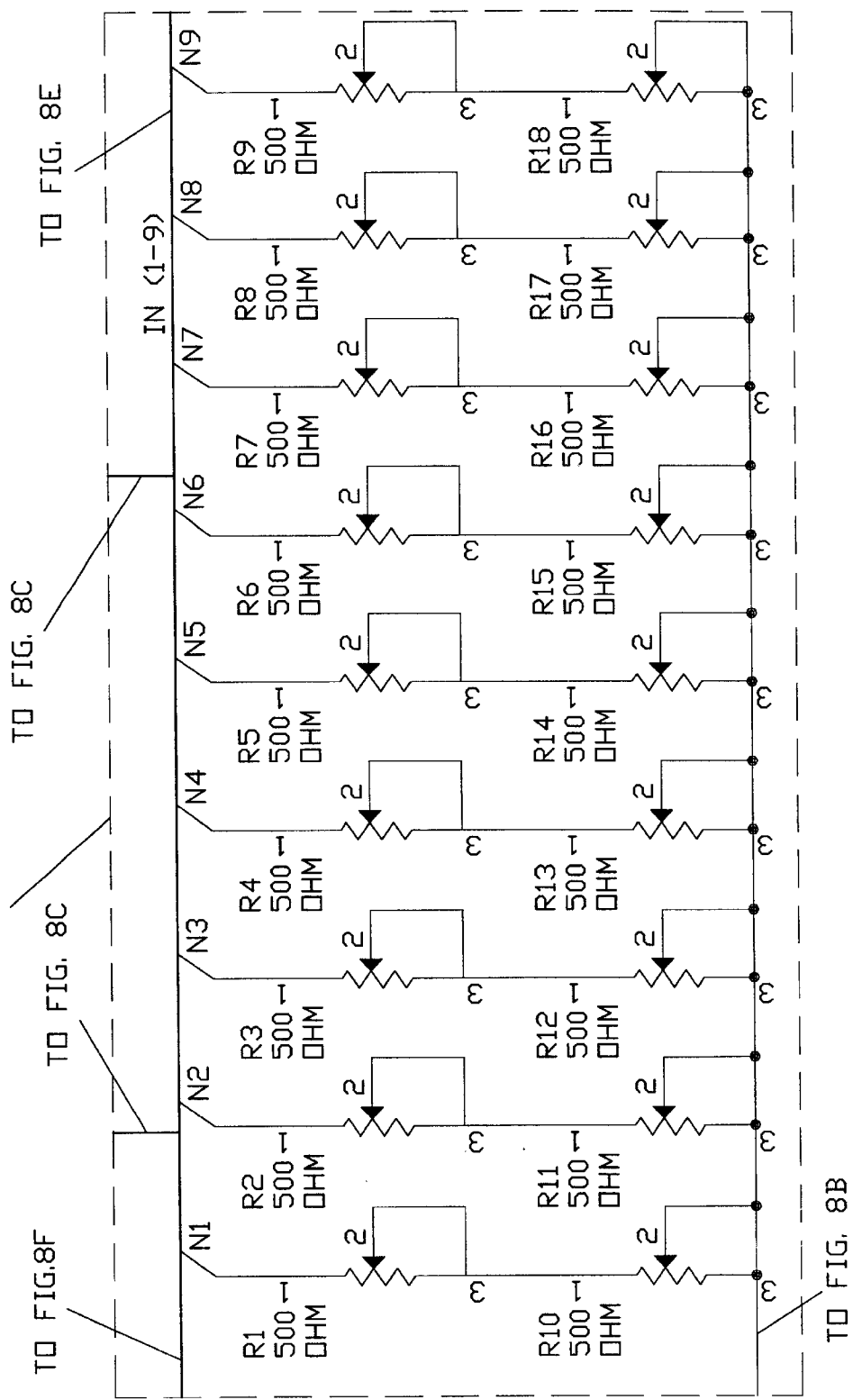
Figure 8J:
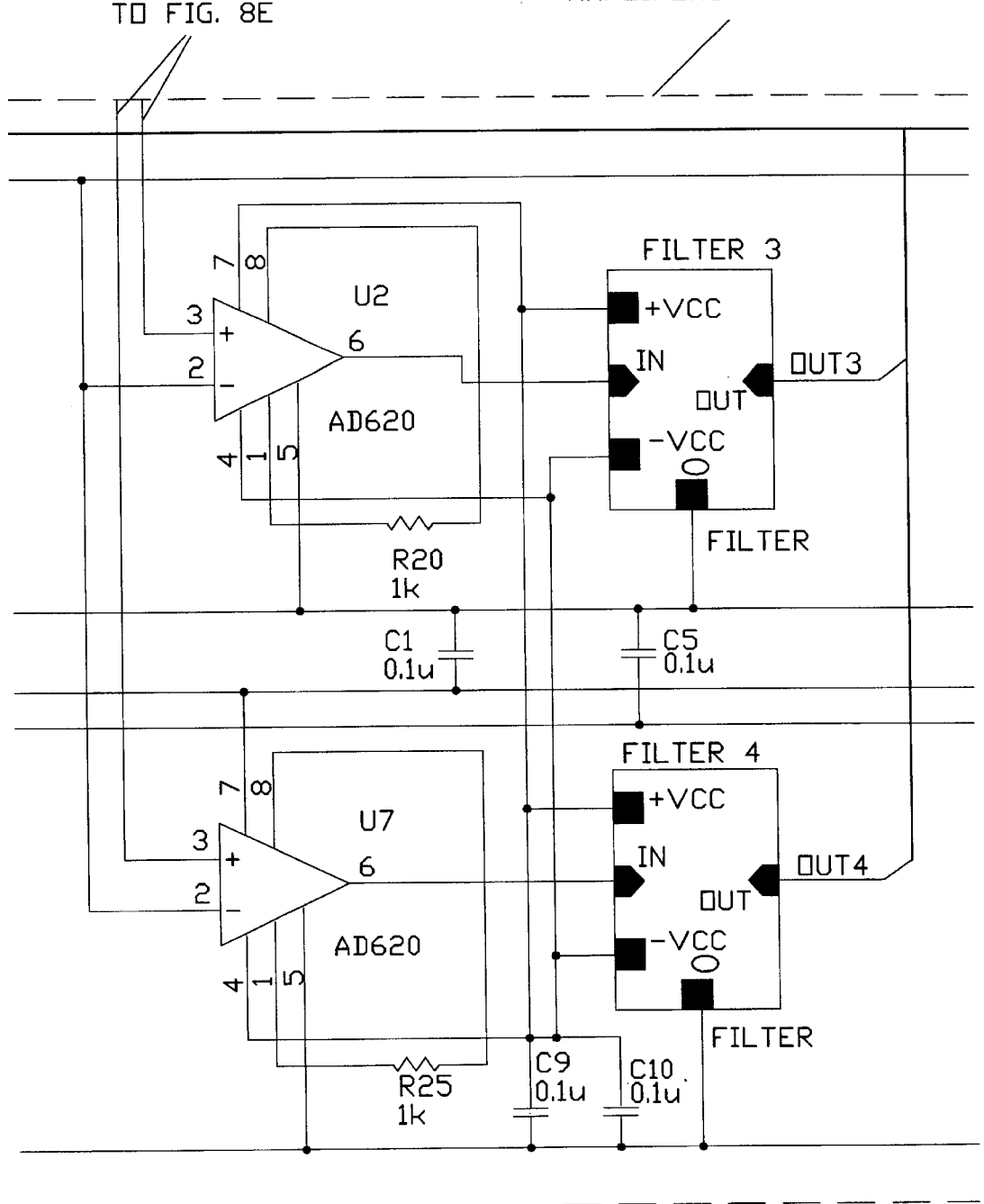

In operation, the TCD's are typically operated in a constant voltage mode, but may also be operated in a constant power mode or other modes that those of skill in the art will recognize based on this disclosure. For example, FIGS. 8A through 8K present detailed schematics of the electronics for the electrical measurement circuitry—that is, of the signal processing circuit(s)—for a six channel embodiment. As illustrated, the six TCD's 510 form the top half of a Wheatstone bridge with a common reference TCD 511 (FIG. 8A). Each leg of the bridge has external potentiometers for bridge balancing. The bridge output is amplified using an instrumentation amplifier and filtered before being sent to a data acquisition board. The electronics are mounted on a single printed circuit board, the schematic of which is shown in FIG. 8B. External DC power is applied to Connector 3 (CON3). The bridge voltage is adjusted using a potentiometer. Pogo pins may connect the nine TCD's to the electronics board (Connector 10, CON10), although other embodiments may be used. Each TCD typically has two potentiometers for coarse and fine nulling of the bridge. Switches are used to select six out of the nine TCD's for measurement and to pick the reference TCD. Alternate modes of operation include a constant temperature mode and a constant power mode, both of which require modifications to the electronics, but that those of skill in the art will be able to practice upon review of this specification.

The bridge configuration with the reference TCD reduces common-mode noise such as temperature drifts in the TCD heater module. The noise reduction is better when the measurement TCD and the reference TCD are substantially identical with respect to heat transfer characteristics, and the filament electrical properties including temperature coefficient of resistance and the electrical resistance. Variations across the wafer during the fabrication process should therefore be minimized. In the realized devices, the temperature coefficient of resistance varied by 10%, but preferably is less than 2%. The electrical resistance varied by 7.5%, but preferably varies less than 5%. Control of the deposition of the thin film onto the support structure to achieve a more uniform coating can improve the sensitivity.

Injection System

The particular injection system(s) employed for injecting the four or more gaseous samples into the mobile phase of the gas chromatography column is not of critical significance to the invention. Any suitable injection system or approach can be employed.

Liquid samples are preferably injected into the parallel gas chromatograph of the invention using a parallel injection block. The injection block comprises two or more, and preferably four or more channels. Described herein as a four-channel injection block, the parallel injection block comprises four or more inlet (e.g., injection) ports for receiving liquid samples, and four or more vaporization chambers, each of the four or more vaporization chambers being in fluid communication with one of the four or more inlet (injection) ports. The four or more vaporization chambers are preferably heated, such that the liquid samples are vaporized therein. The vapor chambers can optionally be maintained at a reduced, sub-atmospheric pressure, such that the liquids are vaporized at a lower temperature relative to the vaporization temperature at atmospheric pressure. The parallel injection block further comprises four or more outlet ports for discharging the vaporized samples, each of the four or more outlet ports being in fluid communication with one of the four or more vaporization chambers.

The parallel injection block can optionally, but preferably, further comprise four or more purge ports for admitting a purge gas into the vaporization chamber to purge the chamber between samples. The four or more purge ports are each in fluid communication with one of the vaporization chambers. In operation, one or more liquid samples are injected into a vaporization chamber, preferably in parallel, to vaporize the one or more liquid samples to form one or more gaseous samples. The one or more gaseous samples are injecting into a mobile phase (i.e., carrier gas stream) flowing through one or more gas chromatography columns, respectively. The vaporization chamber(s) are purged with a purge gas. Significantly, the purge gas can be different from the carrier gas. At least one analyte is separated from other constituents of the gas sample in the chromatography column(s), and the separated analyte(s) are detected with a detector, such as a detector of the microdector array. Subsequently, the purge gas is detected with the detector. This method can be effected in parallel, for example, with a four channel system as described. Advantageously, the use of a purge gas that is different from the carrier gas, and that is detectable, allows one to identify mis-injections. Such identification is particularly important in high-throughput screening systems, including high-throughput screening systems for catalysis.

Each of the inlet/injection ports of the parallel injection block is preferably adapted for releasably receiving a syringe for delivery of the sample to the vaporization chamber, and for resealing upon removal of the syringe. In a preferred embodiment, each of the four or more inlet/injection ports comprise a septum for releasably receiving a syringe. The septum can be a physical septum, such as polymeric sheet of material, or alternatively, a mechanical septum. Mechanical septums comprising a duck-bill valving arrangement, such as the Microseal™ (available from Merlin).

The four or more gaseous samples, vaporized from the liquid samples and discharged from the parallel injection block, are preferably simultaneously injected into the four or more gas chromatography columns using a parallel injector comprising one or more injection valves. The particular nature of the parallel injector or parallel injection valves is not critical. Several variations of parallel injection valves suitable for gas chromatography are described herein or in related applications. In a preferred gas chromatograph system, the parallel injection block comprises the parallel vaporizer (as described above) and a parallel injector—comprising one or more injection valves for simultaneous injection of four or more gaseous phase samples into the mobile phase of four or more chromatography columns, respectively. The parallel injector can be integral with, or separate from, the parallel vaporizer. The parallel vaporizer is preferably integral with a parallel injector comprising four or more injection ports.

A parallel injection valve can generally comprise four or more sample inlet ports for simultaneously receiving four or more gaseous samples. Each of the four or more sample inlet ports are in selective fluid communication with (i) the inlet of at least one sample loop, when the injection valve is in a first position, and with (ii) an exhaust port when the injection valve is in a second position. The parallel injection valve further comprises four or more carrier inlet ports for simultaneously receiving a carrier gas. Each of the four or more carrier inlet ports are in selective fluid communication with (i) a gas chromatography column when the injection valve is in the first position, and with (ii) the inlet of the at least one sample loop when the injection valve is in the second position. Each of the four or more sample loops further comprises an outlet, the outlet of each of the four or more sample loops being in selective fluid communication with (i) the exhaust port when the injection valve is in the first position, and with (ii) a gas chromatography column when the injection valve is in the second position. As such, the parallel injection valve comprises four or more channels and is adapted for simultaneous injection of four or more samples to the four or more chromatography columns. Specifically, the injection valve is adapted such when the valve is in the first position (the sample loading position), each of the four or more samples flow through their respective sample loops to the four or more exhaust ports, and carrier gas flows through four or more channels of the valve to the respective four or more gas chromatography columns. The injection valve is adapted further, such that when the valve is in the second position (the sample injection position), carrier gasses flow through each of the four or more sample loops, thereby forcing the four or samples through the loops and to the respective four or more gas chromatography columns. Any gasses coming through the four or more sample inlet ports (e.g., purge gas) flows through four or more channels of the valve to the exhaust.

Figure 1C:
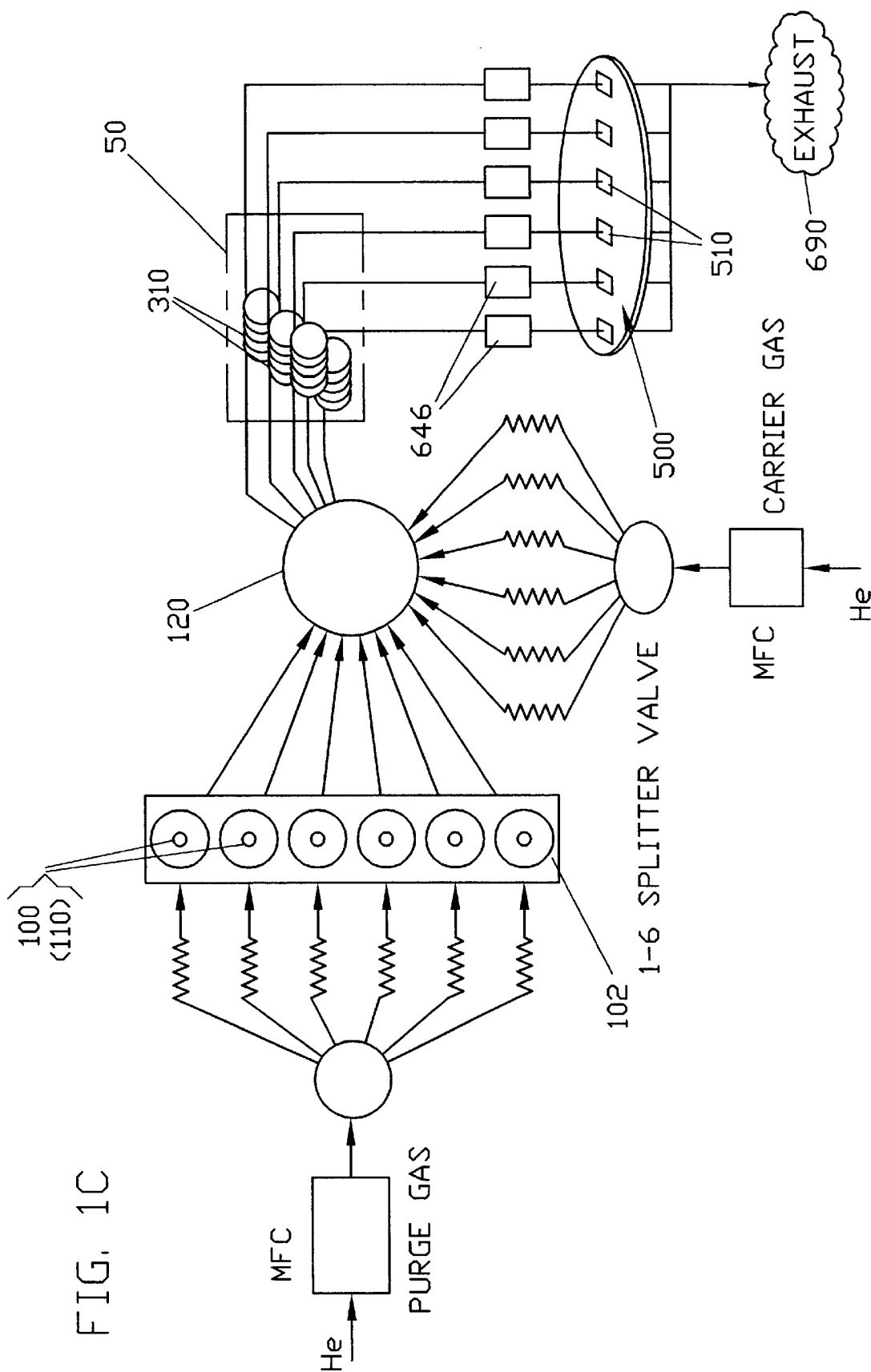
Figure 1D:
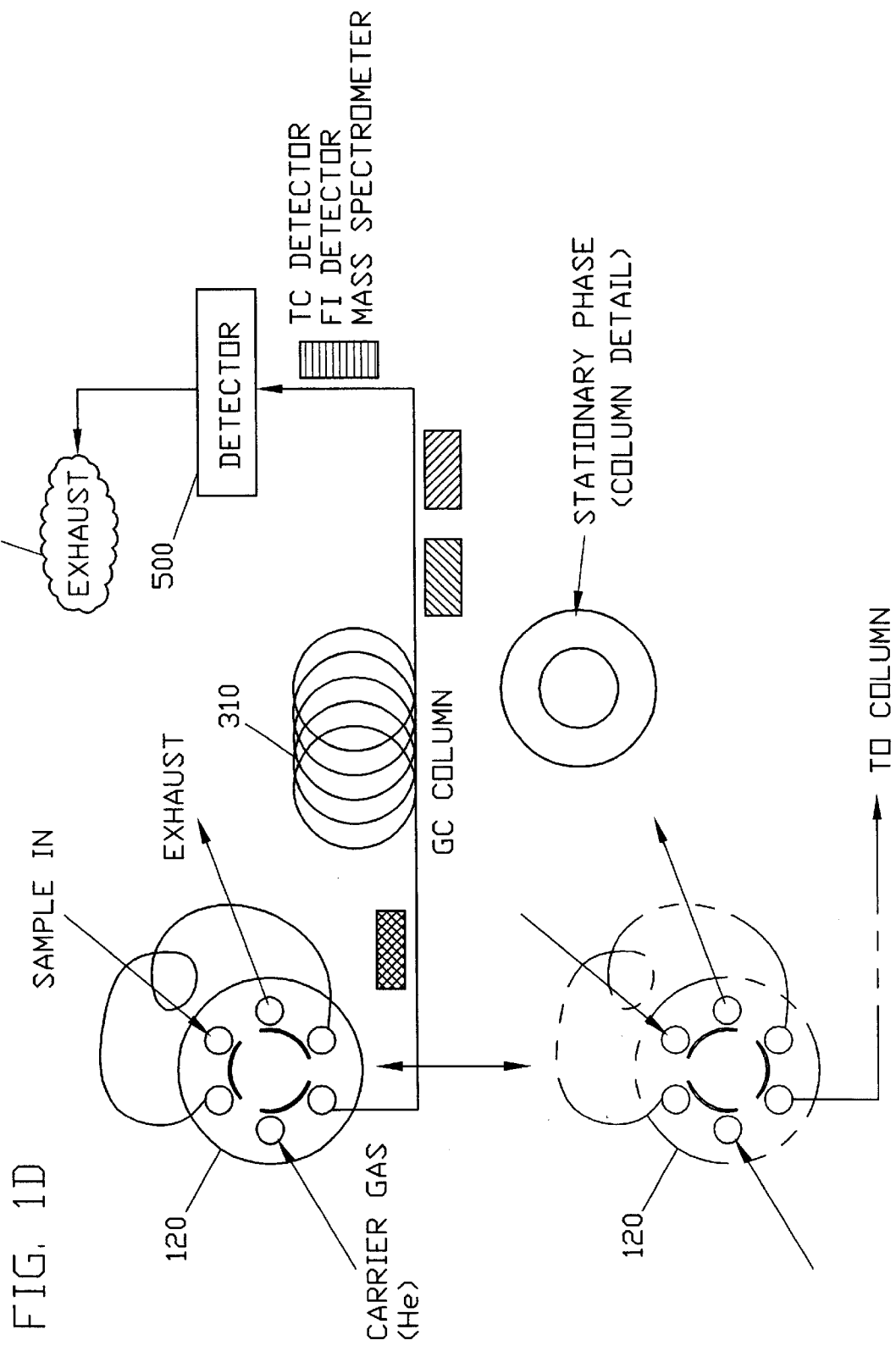

FIGS. 1B, 1C and 1D are schematic diagrams of 6-channel gas chromatography systems. Briefly, with reference first to FIG. 1B, six liquid samples 10 can be simultaneously provided from a sample plate 20 (e.g., microtiter plate), to a set of parallel injection ports 100 by means of an automated robotic handling instrument 30 (e.g., Cavro Scientific, Sunnyvale, Calif.) fitted with a set of 6 parallel syringes. The liquid-receiving injection ports can be parallel injection ports that include a mechanical septum, as described above. The liquid samples 10 are vaporized, and then injected in parallel through an injection valve 120, together with parallel streams of carrier gas, to a set of parallel gas chromatography columns 310. If the samples are gas samples (e.g., from a gas-phase parallel flow reactor), the multi-channel gas samples can be directly coupled to the injection port 100 or injection valve 120 (without vaporization). Analytes are separated in the gas chromatogrpahy columns 310, and then detected with a microfabricated array 500 of microdetectors 510, such as a thermal conductivity microdetectors (TCD). The injection ports 100, mechanical septum 110, injection valves 120, GC columns 310 and/or microdetector array 500 can all be enclosed within a common heated environment 50 (e.g. oven). Alternatively, as shown in FIG. 1C, the injection ports 100, mechanical septum 110, injection valves 120 and/or microdetector array 500 can be external to the heated environment 50, with their own, independent heat sources as necessary—such as the heated injection block 102 for the liquid injection ports 100 and associated septum 110. Significantly, decoupling of the injectors 120 and/or detectors 500 from the columns 310 (and associated heated environment 50) can allow for operation of the oven at different temperatures (including various ramping programs) than the other components. Operating temperatures are not critical, but are preferably not more than about 300° C. for the injector and for the detector.

Figure 2A:
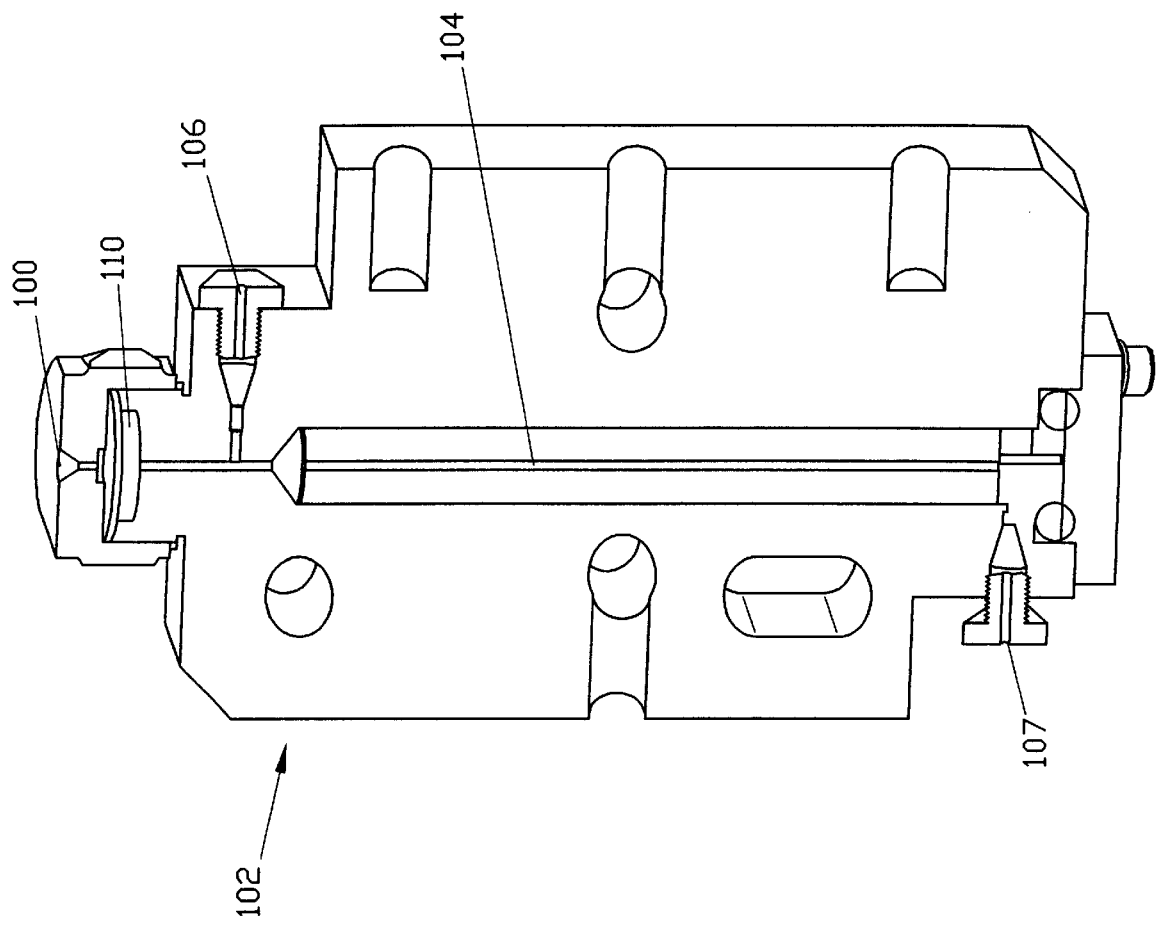

For liquid sample injection, a particularly preferred injection block 102 is shown schematically in FIGS. 2A (end-view cross section) and 2B (perspective). A schematic of a preferred mechanical septum is shown in FIGS. 2C through 2F. The injection block 102 has six modules, each of which has an injection port 100 with a mechanical septa 110, a vaporization chamber 104, and a purge inlet 106 and purge outlet 107 (FIG. 2A). The six modules are stacked and heated using a cartridge heaters having heater wires 108 (FIG. 2B). The spacing between the injection ports 100 is about 18 mm, which is the separation between alternate wells in a standard 96-well (8×12) microtiterplate. Six injection syringe needles with a pitch of 18 mm aspirate samples from alternate wells of a column, and inject in parallel into the vaporization chamber 104 of the injection module 102 via the mechanical septa 110. The expanding volume of the vaporized sample fills up the sample loop in the injection valve 120 that is connected to the outlet port 107 of the injection module 102 using inert tubing. The vaporization chamber 104 in the injection module 102 has an inert sleeve that can be replaced in case of fouling or clogging. The chamber 104 can also be filled with glass wool to increase surface area for evaporation. After injection, the vaporization chamber 104 is purged using $N_2$ or any other inert gas to clear the residual sample before the next injection. One embodiment of a mechanical septum (FIG. 2C) is available from Merlin Instruments, Half Moon Bay, Calif. Conventional septa may also be employed in the parallel GC instrument, however the advantage of the mechanical septa is the superior sealing and increased lifetime. Sealing in the septa is achieved by an inert polymeric duckbill that is closed using a spring. The syringe needle pierces the duckbill (FIGS. 2E and 2F), which seals around the needle. The carrier gas and purge gas to the six injection modules is metered using two mass flow controllers. Flow is split equally from the individual mass flow controller to the six modules using capillary flow restrictors. The capillary dimensions are chosen so that the pressure drop in the capillary is higher than that in the rest of the system by a factor of five, preferably ten.

Figure 3A:
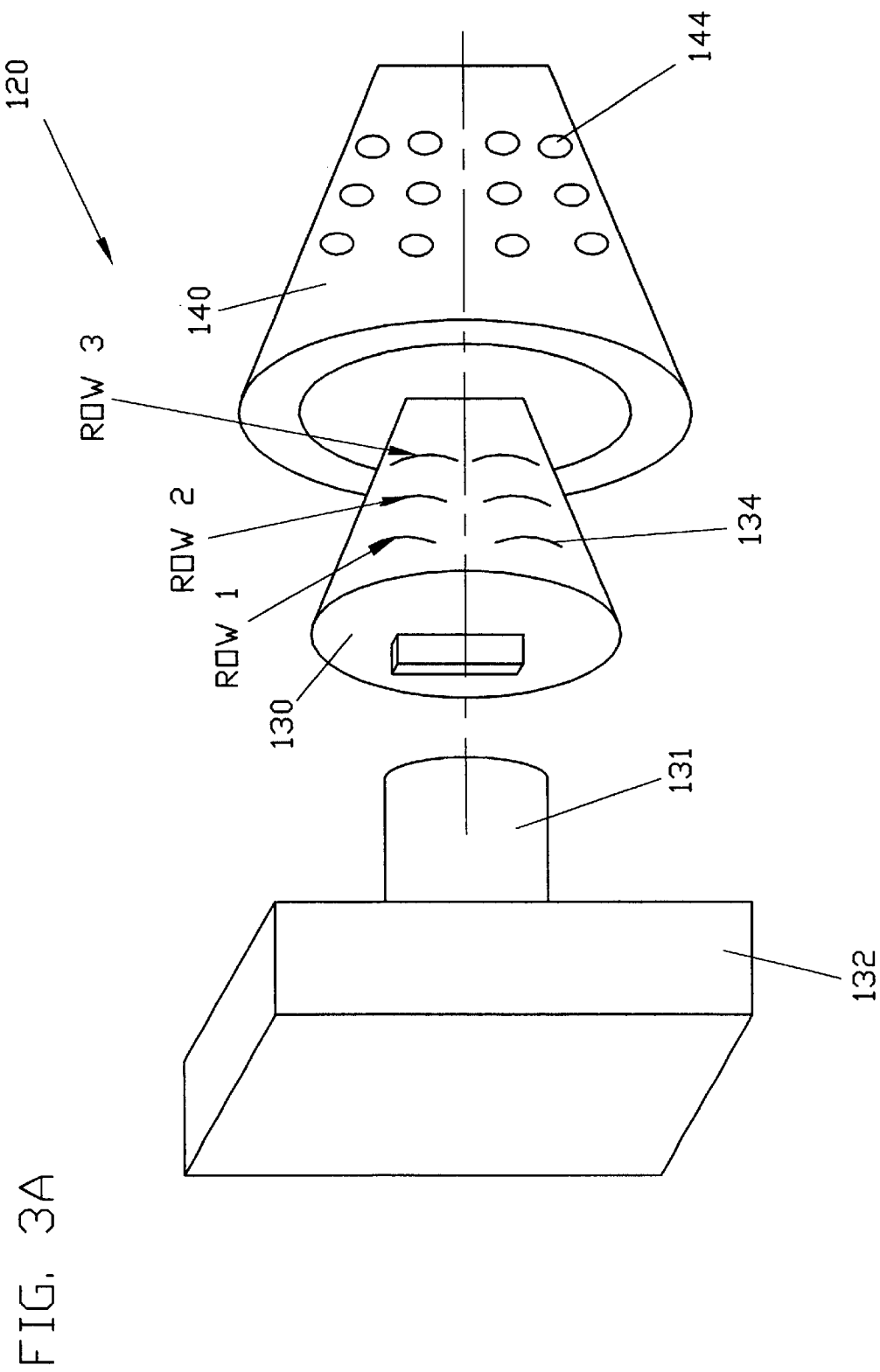
Figure 3C:
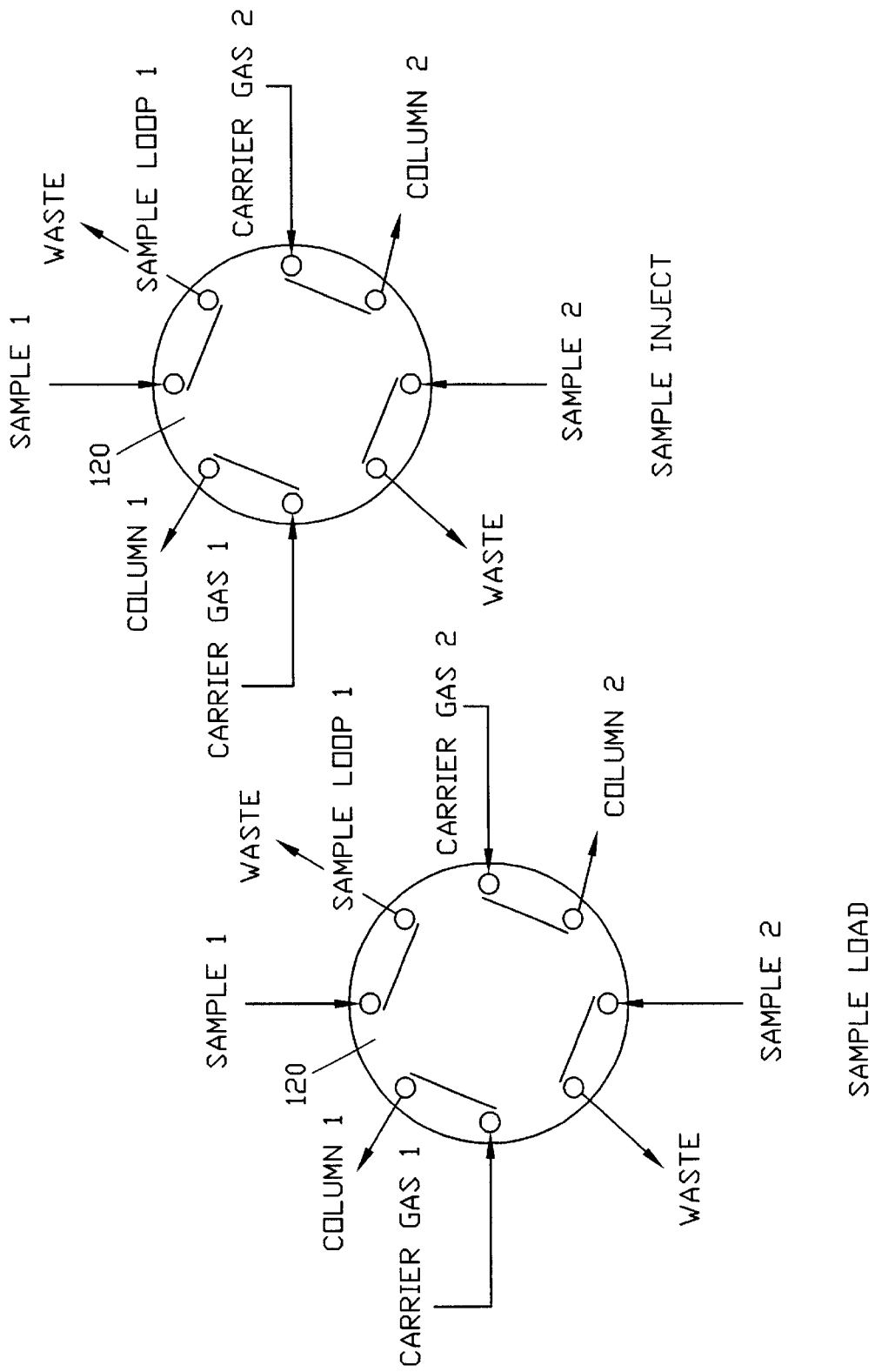

The injection valve, and variations thereon, is shown in FIGS. 3A, 3B and 3C. As shown in FIG. 3A, the injection valve 120 comprises a rotor 130 with grooves 134 that slides inside a fixed stator 140 (e.g., valve body) with inlet and outlet as well as sample loop ports 144 (e.g., with gas connection fittings). The grooves 134 on the rotor 130 and the corresponding ports 144 on the stator 140 (e.g., valve body) are arranged, preferably, in three rows, each row having twelve grooves 134/twelve ports 144 for two sample injection loops. In other embodiments, there may be more or less rows. Sealing between the grooves 134 is achieved by pressing together the smooth inert surfaces of the rotor 130 and the stator 140 with sufficient force. The rotor 130 has two positions, sample loop filling and sample inject, and is driven by a shaft 131 connected to a rotor actuator 132. In the sample loop filling mode, the outlet of the injection module is connected to the sample loop and exhaust via the grooves 134 on the rotor. The carrier gas is directly connected to the column. In the sample inject position, the carrier gas transports the sample plug from the sample loop and injects on to the column. An alternative embodiment is shown in FIG. 3B, showing a twelve-port injection valve 120 having two sample loops external to the injection valve body. By increasing the number of ports by six, another external sample loop can be added on the same rotor. Therefore, with 12 ports arranged on the circumference of the valve, 2 injection ports are accommodated, whereas with 18 ports, three injection ports are accommodated, and so on. Another alternative embodiment is shown in FIG. 3C, showing an eight-port injection valve 120 having two internal sample loops. By increasing the number of ports by four, another internal sample loop can be added on the same rotor. Therefore, with 8 ports arranged on the circumference of the valve, 2 injection ports are accommodated, whereas with 12 ports, three injection ports are accommodated, and so on.

Figure 4:
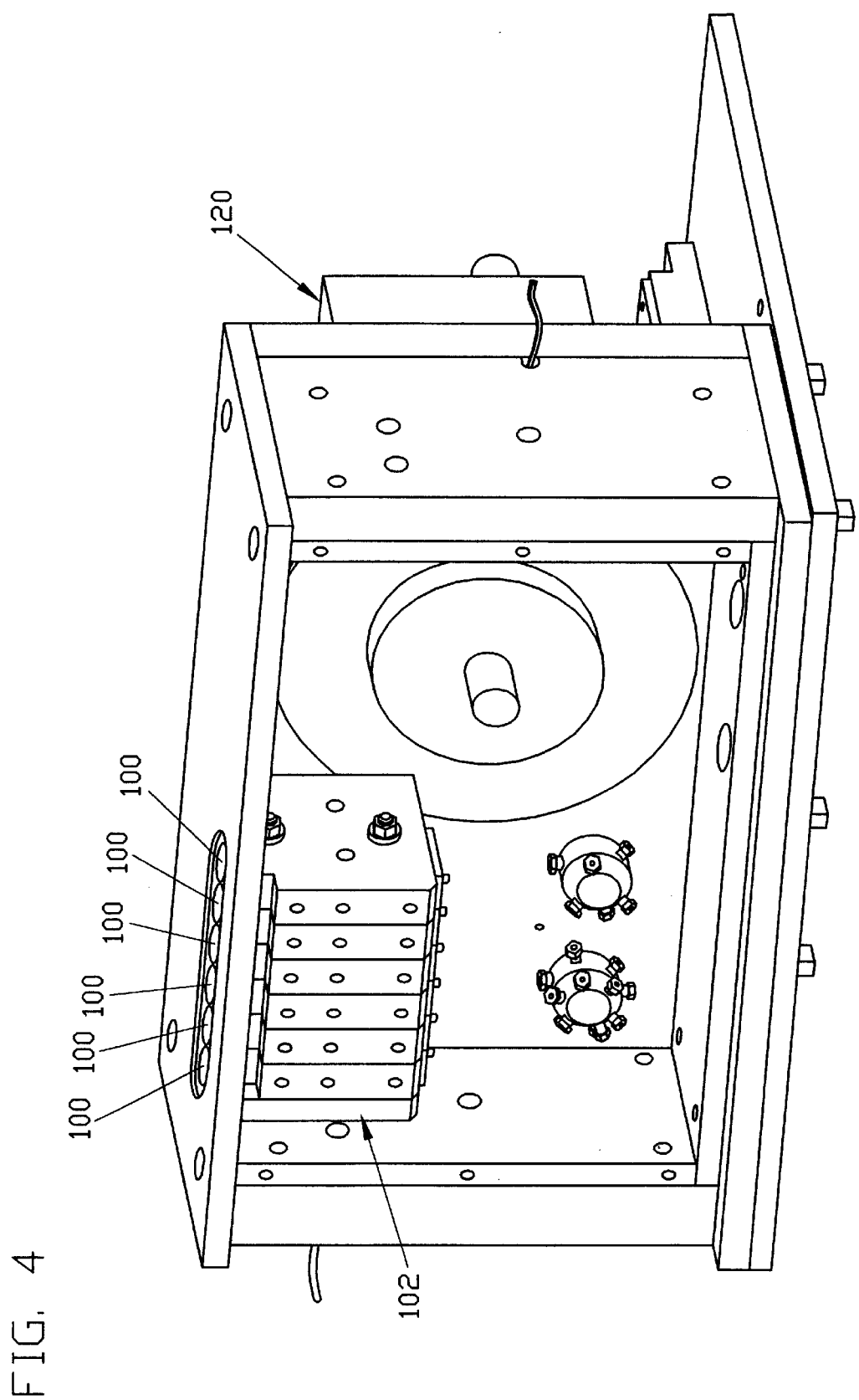
FIG. 4 is a perspective view of an integrated parallel vaporizer and parallel injection valve.

A perspective view of an integrated platform comprising the parallel injection block 102 with an integral parallel vaporizer, together with the rotary injection valve 120 is shown in FIG. 4. The rotary injection valve 120 is a 2-position, 6-channel, single-loop parallel injection valve.

As an alternative injection valve, a commercially available 6-port membrane 32 valve can be used (e.g., Valveco #DV22-21160). However, use of such a conventional valve will require a larger number of valves (one for each channel). Moreover, such valves have temperature limitations (e.g., ~200° C.) that limits their universality of application for high-temperature applications. Nonetheless, such a conventional valve provides improved space constraints (as compared to the rotary-type valves described above). As a further alternative, conventional rotary-type valves can be employed, especially for higher temperatures (e.g., ~350° C.).

For gaseous samples, and especially gaseous samples to be analyzed directly from a parallel flow reactor, such as a parallel flow process optimization reactor (discussed below), the parallel injection valve is preferably a multi-channel valve where each channel achieves injection into one of the channels gas chromatography column by an array of microvalves, preferably membrane-actuated microvalves. A particularly preferred injection valve for such applications is disclosed in co-pending U.S. Serial No. 60/274,022 entitled "Gas Chromatograph Injection Valve Having Microvalve Array" filed on the date even herewith (Mar. 7, 2001) by Bergh et al.

High-throughput Catalysis Screening

The gas chromatograph of the invention is advantageously applied for simultaneous gas chromatogrpahy analysis of four or more liquid or gaseous samples. In preferred embodiments, the gas chromatograph can be applied to screen catalysts in a high-throughput (i.e., combinatorial) research program directed to heterogeneous or homogeneous catalysts. Preferred aspects of combinatorial catalysts research programs are described, for example, in the aforementioned related applications, including especially U.S. Pat. No. 6,030,917 to Weinberg et al., U.S. Pat. No. 6,063,633 to Willson, U.S. Pat. No. 6,149,882 to Guan et al., and PCT application WO 00/51720 by Bergh et al.

Generally, candidate catalysts can be evaluated by simultaneously contacting four or more candidate catalysts with one or more reactants in a parallel reactor under reaction conditions to catalyze at least one reaction, and detecting the resulting reaction products or unreacted reactants in parallel with the gas chromatograph to determine the relative performance of the candidate catalysts. The four or more of candidate catalysts can have different compositions, for compositional investigation (including supports). Additionally, or alternatively, the four or more candidate catalysts can be contacted with the one or more reactants under different reaction conditions (e.g., temperature, pressure, flow rate, residence time, feed composition, etc.).

The parallel reactor can be of any type known in the art. Preferably, the reactor can be a parallel batch reactor, a parallel semicontinuous reactor, or a parallel flow reactor. A parallel flow reactor preferably comprises four or more reaction vessels, each of the four or more reaction vessels comprising an inlet for feeding reactants into the reaction vessel, a reaction zone for effecting a chemical reaction, and an outlet for discharging reaction products and unreacted reactants, if any, the outlets of the four or more reaction vessels being in at least sampling fluid communication with the inlets of the four or more gas chromatography columns, respectively. For investigating catalyst composition in a heterogeneous catalysis system, a parallel flow reactor such as described in U.S. Pat. No. 6,149,882 to Guan et al. (parallel fixed bed reactor), or as described in PCT application WO 00/51720 by Bergh et al. (massively parallel microreactor) are particularly preferred, and are hereby incorporated by reference. For investigating process conditions (including optimization of reaction conditions) in a heterogeneous catalysis system, a parallel flow reactor such as described in the following co-pending patent applications are particularly preferred, and are hereby incorporated by reference: U.S. Ser. No. 09/801,390, entitled "Parallel Flow Process Optimization Reactors" filed on the date even herewith (Mar. 7, 2001) by Bergh et al.; U.S. Ser. No. 09/801,389, entitled "Parallel Flow Reactor Having Variable Composition" filed on the date even herewith (Mar. 8, 2001) by Bergh et al.; and U.S. Serial No. 60/274,065, entitled "Parallel Flow Reactor Having Improved Thermal Control" filed on the date even herewith (Mar. 7, 2001) by Bergh et al.

The samples to be analyzed can be provided directly from the parallel reactor (batch, semicontinuous or continuous flow) or, alternatively, can be indirectly provided. For example, one or more components of a reaction mixture to be analyzed can be adsorbed onto a sorbent during or after a reaction of interest. (See WO 00/51720 by Bergh et al.; See also WO 00/14529). The analyte can subsequently be desorbed for analysis by the parallel gas chromatograph of the invention.

High-throughput screening can be achieved using the parallel systems described herein. In one preferred approach, the four or more samples are simultaneously injected into four or more injection ports at a first time $t_1$, the four or more samples are optionally simultaneously vaporized, and then simultaneously injected into the four or more corresponding gas chromatography columns. The four or more gas samples are simultaneously contacted with the separation media in the respective gas chromatography columns to separate at least one analyte from other constituents of the gas samples, and the four or more separated analytes are then simultaneously detected at a second time $t_2$. The difference in time, $t_2-t_1$, is not more than about 60 minutes, preferably not more than about 20 minutes, and more preferably not more than about 10 minutes. As such, the overall sample throughput can range from about 0.5 minutes per sample to about 60 minutes per sample, and preferably from about 1 minute per sample to about 10 minutes per sample.

The following example illustrates the principles and advantages of the invention.

EXAMPLE 1

Microfabrication of Integral Thermal Conductivity Detector

An array comprising microfabricated thermal conductivity detectors was made using substantially known prior art microfabrication techniques. Briefly, with reference to FIGS. 6A through 6P (and where indicated, also to FIGS. 5L and 5M), fabrication was effected as follows:

1. Wafer 1 (bottom capillary wafer 620 (FIG. 5L), 400 $\mu$m thick), and Wafer 2 (central filament wafer 610 (FIGS. 5L and 5M) 400 $\mu$m thick) were provided. Both Wafer 1 and Wafer 2 were single-crystal silicon wafers (Si-wafers): <100> oriented; 125 mm diameter; 400 $\mu$m thickness; and double-sided polished.
2. Wafer 1 was oxidized on both sides (oven at 1100° C., wet, about 3.3 $\mu$m thick).
3. Wafer 1: spinning of photo resist on front side/baking.
4. Wafer 1: spinning of photo resist on back side/baking.
5. Wafer 1: double-sided photolithography (1) on front side of wafer (fluidic holes for inlet port and outlet port, 150 $\mu$m diameter) and back side of wafer (holes for capillaries, 400 $\mu$m diameter) Hardbake at 120° C.
6. Wafer 1: etching of oxide on front- and back-side of wafer 1 (wet chemical etching, buffered HF (BHF)).
7. Wafer 1: stripping of photo resist on both sides, cleaning in Caro etch.

At this point, the capillary wafer (Wafer 1) and the filament wafer (Wafer 2) were as illustrated as shown in FIG. 6A. Further fabrication continued as follows:

8. The capillary wafer 620 (Wafer 1) and yet unprocessed filament wafer 610 (Wafer 2) were diffusion bonded, with the front side of wafer 1 with smaller holes (for the TCD inlet and outlet ports) towards wafer 2, and larger holes (for capillaries) on the outside. As illustrated, the larger capillary holes of wafer 1 are now the bottom of this two-wafer-pack. Fusion bonding was effected at ~1000° C., for four hours, under nitrogen.

At this point, the bonded wafers (comprising the filament wafer and the capillary wafer) were as illustrated as shown in FIG. 6B. Further fabrication continued as follows:

9. Bonded Wafer 1/Wafer 2: deposition of SiN (LPCVD, both sides, 1 $\mu$m thick, dichlorosilane process, stress-optimized for low stress (~100 MPa tensile)).

At this point, the bonded wafers were as illustrated as shown in FIG. 6C. Further fabrication continued as follows:

10. Spinning of photo resist on exposed front side of Wafer 2 (filament wafer 610) (image reversal resist).
11. Photolithography (2) on front side to pattern for Pt contacts and Pt filament with meandering geometry design of Pt filament on SiN suppport bridge (for following liftoff).
12. Deposition of Cr adhesion layer (sputtering, 10 nm thick) onto SiN on front side.
13. Deposition of Pt (sputtering, 100 nm thick) onto Pt adhesion layer on front side. The center-deposited Pt will become the Pt filament 520, and the peripheral-deposited Pt will become the detector contacts 523, 524.
14. Lift-off of Pt (photo resist is stripped).

At this point, the bonded wafers were as illustrated as shown in FIG. 6D (for simplicity, the deposited Cr adhesion layer and/Pt layer are shown as a single layer). Further fabrication continued as follows:

15. Spinning of photo resist on front side of Wafer 2 (filament wafer 610).
16. Photolithography (3) on front side to pattern SiN in preparation for formation of gas channel and detection filament membrane.
17. Etching of SiN (dry etching CHF$_3$, RIE in AME8100).
18. Stripping of photo resist.

At this point, the bonded wafers were as illustrated as shown in FIG. 6E. Further fabrication continued as follows:

19. Deposition of Pyrex (3 $\mu$m thick, by sputtering (only 100 nm/h) or evaporation) onto exposed front side of Wafer 2 (filament wafer 610). Pyrex is used to facilitate subsequent anodic bonding of the filament wafer 610 to a capping wafer 630.
20. Planarization of Pyrex (mechanical polishing, Hr. Dinges), cleaning.
21. Spinning of photo resist on front side of Wafer 2 (filament wafer 610) over Pyrex layer.
22. Photolithography (4) on front side of Wafer 2 (filament wafer 610) to pattern Pyrex for bond pads and detection channel, "over sizing".
23. Etching of patterned Pyrex (for bond pads and detection channel) (wet chemical etching using buffered HF).
24. Stripping of photo resist (from Pyrex)
25. Deposition of chromium adhesion layer and subsequent nickel layer (Cr/Ni, 0.5 $\mu$m total, for protection of Pyrex during subsequent etching step).
26. Spinning of photo resist onto front exposed surface of Wafer 2 (filament wafer 610).
27. Photolithography (5) on exposed front side of Wafer 2 to pattern for detection channel and detection filament support membrane.
28. Etching of Ni/Cr layer for gas detection channel (wet chemical etching).
29. Stripping of photo resist.
30. KOH-etching of Si to form gas detection channel (250 $\mu$m, time controlled).

At this point, the bonded wafers were as illustrated as shown in FIG. 6F (for simplicity, the Pyrex layer and Ni/Cr layers are not illustrated) Further fabrication continued as follows:

31. Deposition of Al layer (~1 $\mu$m) on exposed front side of Wafer 2 (filament wafer 610) to act as an etch stop for subsequent ASE etching of back side of Wafer 1 (capillary wafer 620).

At this point, the bonded wafers were as illustrated as shown in FIG. 6G (for simplicity, the Pyrex layer and Ni/Cr layers are not illustrated). Further fabrication continued as follows:

32. ASE-etching of backside of Wafer 1 (capillary wafer 620) to etch SiN and exposed Si to achieve "two level patterning"—simultaneous patterned formation of resulting larger holes for capillaries, and smaller fluidic holes for inlet and outlet ports to detection cavity.

At this point, the bonded wafers were as illustrated as shown in FIG. 6H (for simplicity, the Pyrex layer and Ni/Cr layers are not illustrated). Further fabrication continued as follows:

33. Etching of Al layer on front side of Wafer 2 (filament wafer 610) (wet chemical etching). Careful handling is important during this step.
34. Etching of Ni/Cr layer on front side of Wafer 2 (filament wafer 610) (wet chemical etching) to expose Pyrex.

At this point, the bonded wafers were as illustrated as shown in FIG. 6I (for simplicity, the Pyrex layer is not illustrated). As an optional step, Al can be deposited over the Pt contact pads using a shadow mask approach. At this point, fabrication of the bonded capillary wafer/filament wafer subassembly was completed. The capping wafer 630 (FIG. 5L) was fabricated as follows:

35. A single wafer (top capping wafer 630 (FIG. 5L), 400 $\mu$m thick) was provided. The wafer was single-crystal silicon:

<100> oriented; 125 mm diameter; 400 μm thickness; and double-sided polished.

36. The wafer was thermally oxidized to form SiO₂ layers on both sides of the wafer.

Alternatively, SiN can be deposited on both sides of the wafer (e.g., using LPCVD).

At this point, the capping wafer 630 was as illustrated in FIG. 6J. Further fabrication continued as follows:

37. Two sided aligned patterning of the oxide (or of the SiN layer if SiN is used instead of the oxide) for contact apertures 633, 634 (FIG. 5L) on both sides and for the top portion 516b (FIG. 5L) of the detection cavity 516 (FIG. 5L) on the back side (bottom) of the wafer was then effected.

At this point, the capping wafer 630 was as illustrated in FIG. 6K. Further fabrication continued as follows:

38. The exposed Si was then etched from both sides (~250 μm).

At this point, the capping wafer 630 was as illustrated in FIG. 6L. Further fabrication continued as follows:

39. The SiO₂ (or SiN, if used instead of oxide) was removed by etching both sides.

At this point, the capping wafer 630 was as illustrated in FIG. 6M, and fabrication of the capping wafer 630 subassembly was complete.

With reference to FIG. 6N, the capping wafer 630 was bonded to the subassembly comprising the capillary wafer 620 and the filament wafer 610 (for simplicity, the Pyrex layer is not shown). After alignment, the exposed front side of the filament wafer 610 was anodically bonded to the back side of the capping wafer 630 to result in the final substrate with the integral thermal conductivity detector, as shown in FIG. 6O. Alternatively, adhesive bonding (e.g., using epoxy or polyimide adhesive) can be effected (in which case the Pyrex layer is not required). Capillaries 642, 644 were then connected to the inlet and outlet ports 512', 514' using polyimide glue. Glass soldering can also be used for capillary bonding to the substrate 600. The final, assembled thermal conductivity microdetector is illustrated in FIG. 6P, with reference numerals corresponding to those of FIGS. 5L and 5M.

In an alternative process embodiment to that discussed above, one may instead of using KOH-etching (step 30) use TMAH-etching (25% solution). TMAH attacks Pyrex, however, so use of TMAH skips the steps 25–29 and 34 (one deposition, one lithography, two etching).

EXAMPLE 2

Microfabrication of Integral Thermal Conductivity Detector

In an alternative embodiment, an array comprising microfabricated thermal conductivity detectors was made using substantially known prior art microfabrication techniques. Briefly, with reference to FIGS. 10A through 10E, (and where indicated, also to FIGS. 7F and 7G), fabrication was effected as follows:

1. A wafer (filament wafer 680 (FIGS. 7F and 7G), 400 μm thick) was provided. The wafer was single-crystal silicon: <100> oriented; 125 mm diameter; 400 μm thickness; and double-sided polished.
2. A SiN layer was deposited on both sides (LPCVD, 1 μm thickness) (See FIG. 10A).
3. The top side of the filament wafer 680 was subseqently patterned, and the filament 520 and contact pads 523, 524 were formed as Cr/Pt layers, substantially as described in Example 1. (See FIG. 10B).
4. Both sides of the SiN were then patterned (using photolithography and etching) in preparation for formation of the detection cavity lower portion 516b and the inlet and outlet ports 512, 514. (See FIG. 10C).
5. Pyrex layer was deposited on the front side, and planarized substantially as described in Example 1.
6. The exposed silicon on both sides of the wafer were then etched using KOH, substantially as described in Example 1, to form the detection cavity lower portion 516b and the inlet and outlet ports 512, 514. (See FIG. 10D, for simplicity, Pyrex layer is not shown).
7. A capping wafer was formed substantially as described in Example 1.
8. The capping wafer and the filament wafer were anodically bonded, substantially as described in Example 1.

Figure 10A:
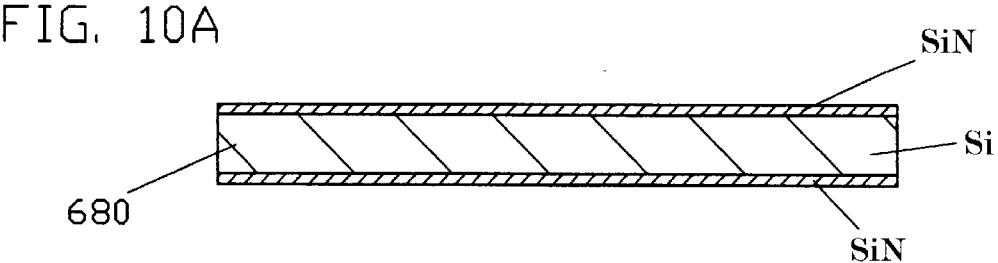
FIGS. 10A through 10E are schematic, cross-sectional views showing various stages of one micro fabrication approach for forming a microfabricated detection cavity having a thin-film detection filament.
Figure 10B:
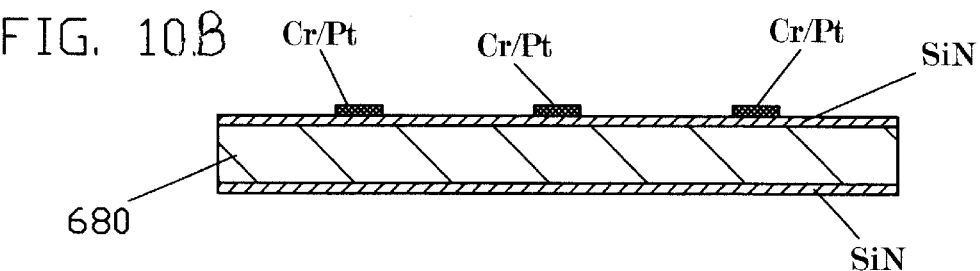
Figure 10C:
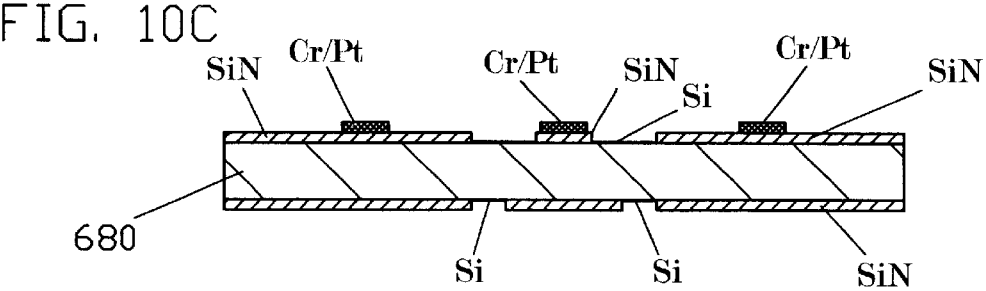
Figure 10D:
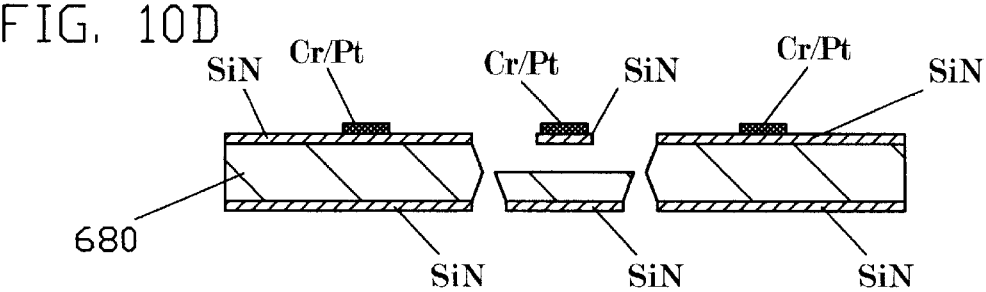
Figure 10E:
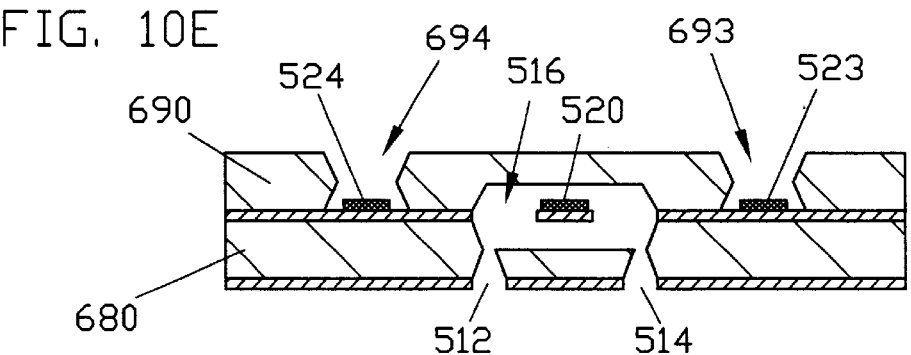

The final, assembled thermal conductivity microdetector is illustrated in FIG. 10E, with reference numerals corresponding to those of FIGS. 7F and 7G.

EXAMPLE 3

Analysis of Liquid Samples

Figure 9:
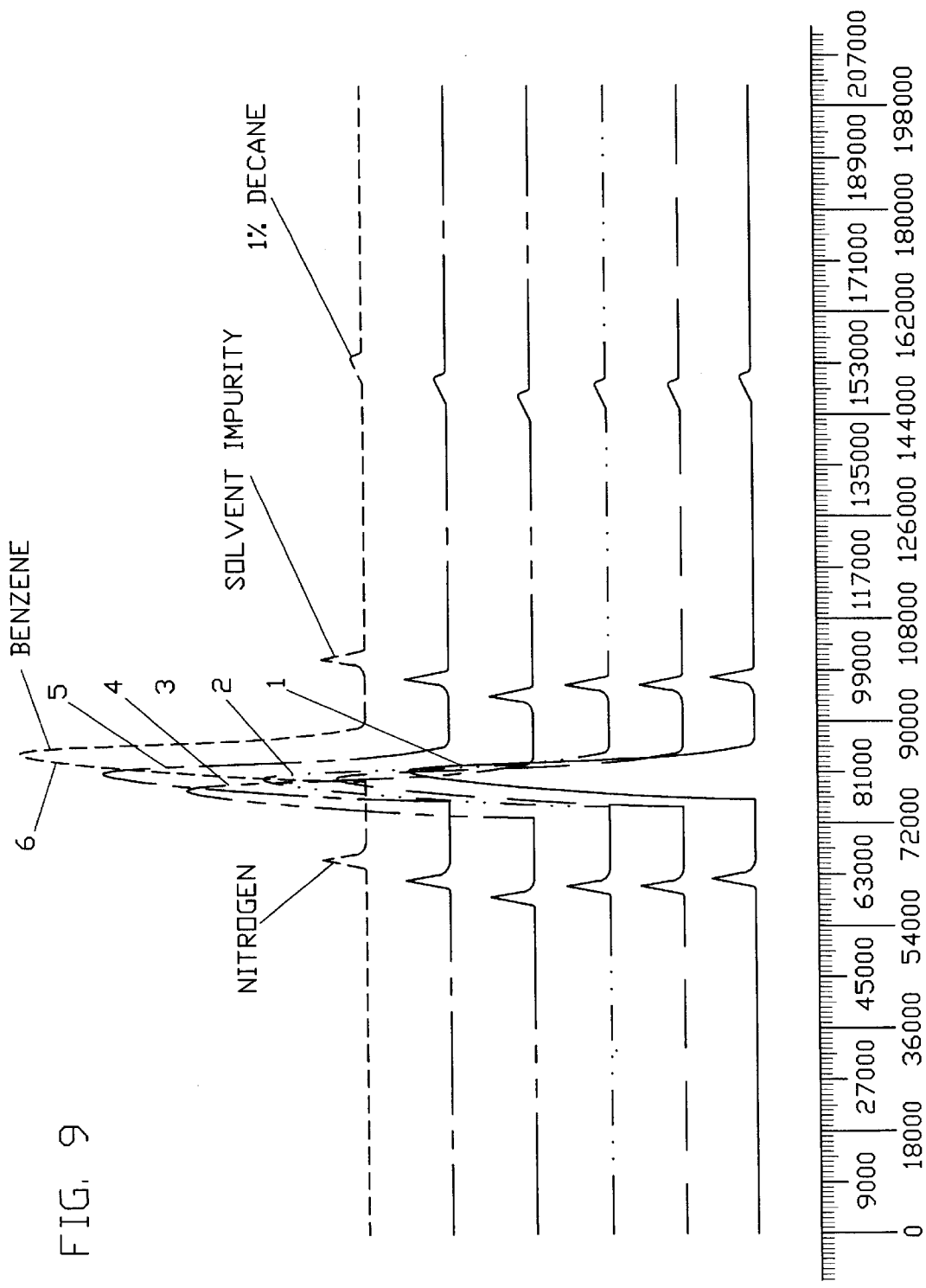
FIG. 9 is a graph showing the detector response (y-axis) versus time (x-axis) as the results of simultaneous analysis of a liquid sample (1% decane in benzene) in a six-channel gas chromatograph having a microfabricated thermal conductivity detector with a thin-film filament.

A six-channel gas chromatograph instrument comprising an array of microdetctors as disclosed herein was used to screen a 96-sample microtiter plate using a 1% decane in benzene mixture in every well of the plate. The results of the chromatogram for six channels of a single run are shown in FIG. 9. The nitrogen peak is the residual purge gas present in the injection block and does not interfere with the chromatogram. Conventional gas chromatograms (GC's) use helium as the purge gas, which cannot be distinguished from the carrier gas which is also helium. The nitrogen peak in the parallel GC offers the ability to monitor for misinjections. The nitrogen peak is typically very large in case of a bad injection (not shown in FIG. 9). The variation in peak area from run to run (after calibration) is less than 10%. The total run-time for the 96 samples was ~58 minutes total, which is less than a factor of six compared with what would have been required using a single channel GC instrument and running the samples in series. The example also demonstrates channel to channel reproducibility.

EXAMPLE 4

Comparative Analysis of Gaseous Sample

A gaseous sample comprising CO (5%), $CO_2$ (5%), $C_2H_6$ (15%), $C_2H_4$ (5%) and $N_2$ (70%) was evaluated using a single-channel gas chromatograph configured to have a thermal conductivity microdetector of the present invention. For comparative purposes, the same sample was detected using a conventional thermal conductivity detector. Specifically, a sample (120 μl sample loop) was injected into a carrier gas stream (2 sccm) and sent through a gas chromatography column (PLOT Q). The sample was analyzed in series using: (1) the thermal conductivity microdetector of the present invention (TCD body temperature 25° C.; detection temperature 280° C.) and (2) a conventional (thermistor-type) Valco thermal conductivity detector (TCD body temperature 25° C.; detection temperature 400° C.).

Figure 12:
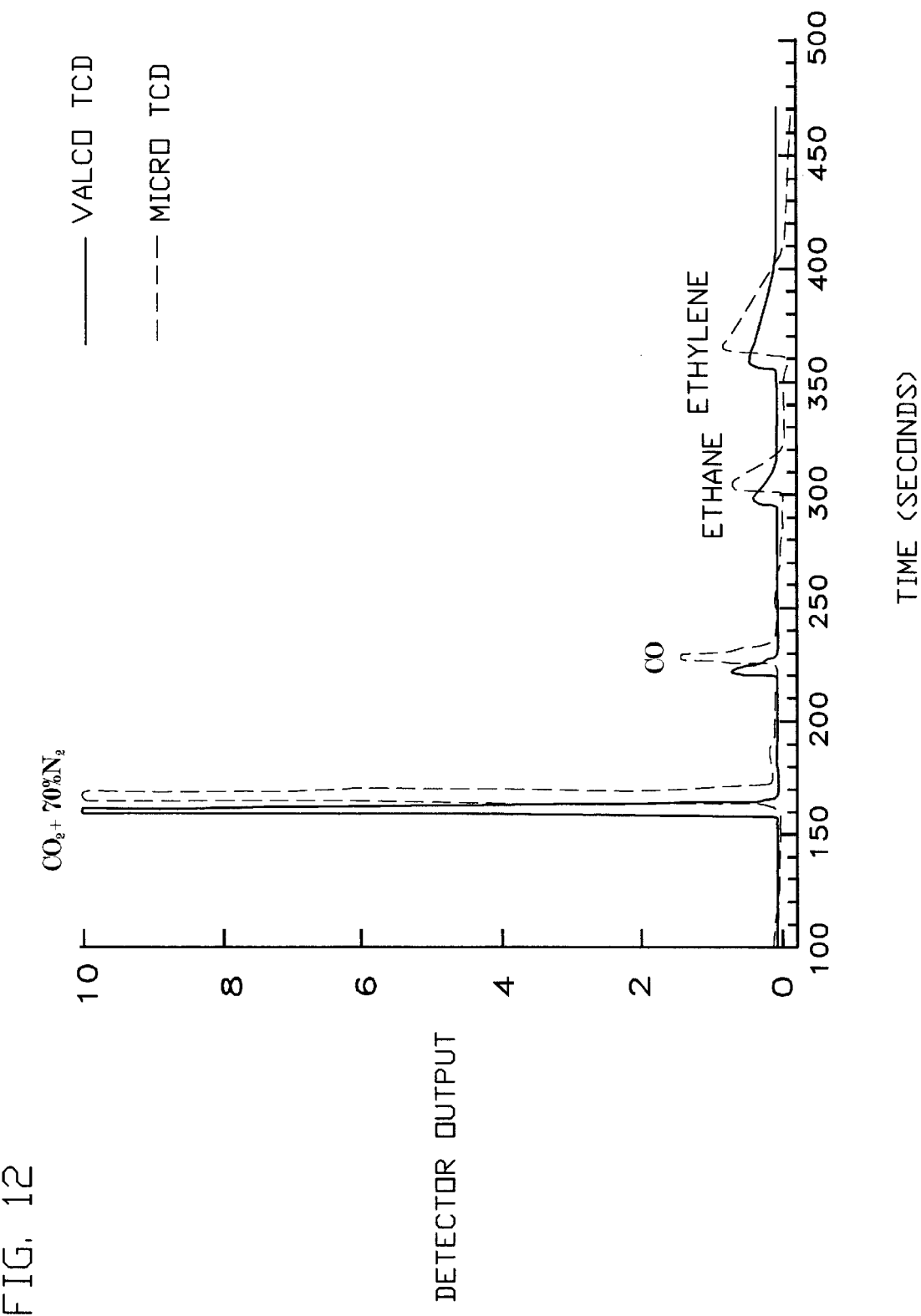
FIG. 12 is a graph showing detector response versus time for a gaseous sample CO (5%), $CO_2$ (5%), $C_2H_6$ (15%), $C_2H_4$ (5%) and $N_2$ (70%) for a single-channel using a thermal conductivity microdetector and, for comparison, a conventional, thermistor-type thermal conductivity detector.

The results, shown in FIG. 12, demonstrate the operability of the thermal conductivity of the microdetector, and in particular, relatively higher sensitivity of the same relative to the conventional thermal conductivity detector.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A gas chromatograph having four or more analysis channels for simultaneous analysis of four or more fluid samples, the gas chromatograph comprising
    four or more gas chromatography columns, each of the four or more gas chromatography columns comprising an inlet for receiving a gaseous mobile phase that includes a gaseous sample, a separation media effective for separating at least one separated component of the gaseous sample from other components thereof, and an outlet for discharging the separated gaseous sample, and
    a microdetector array comprising four or more thermal conductivity microdetectors for detecting the thermal conductivity of said at least one separated component of the gaseous sample, said thermal conductivity microdetectors being detachably mounted on a substrate, each of the four or more thermal conductivity microdetectors having an inlet port in fluid communication with the outlet of one or more of the gas chromatography columns for receiving a separated gaseous sample, a detection cavity, a thin-film detection filament within the detection cavity for detecting at least one separated component of the separated gaseous sample, and an outlet port for discharging the separated gaseous sample.

2. The gas chromatograph of claim 1 wherein the four or more thin-film detection filaments have a temperature-dependent resistance, and the four or more thermal conductivity microdetectors each have a thermal coefficient of resistance that varies less than about 10% between the four or more thermal conductivity microdetectors.

3. The gas chromatograph of claim 1 wherein the thin-film detection filament of each of the four or more thermal conductivity microdetectors has a resistance that varies less than about 25% between the four or more thermal conductivity microdetectors.

4. The gas chromatograph of claim 1 wherein the thin-film detection filament comprises a film of material having a temperature-dependent resistance on a support bridge.

5. The gas chromatograph of claim 1 wherein each of four or more separated gaseous samples flows past a corresponding thin-film detection filament for direct contact with said corresponding thin-film detection filament.

6. The gas chromatograph of claim 5 wherein each of the thin-film detection filaments is arranged within the corresponding detection cavity such that a separated gaseous sample moving through the detection cavity from the inlet port to the outlet port moves around said thin-film detection filament.

7. The gas chromatograph of claim 1 wherein the four or more thermal conductivity microdetectors are mounted individually on the substrate.

8. The gas chromatograph of claim 1 wherein the four or more thermal conductivity microdetectors are mounted on the substrate as one or more modules, each of the one or more modules comprising two or more thermal conductivity microdetectors.

9. The gas chromatograph of claim 1 wherein the four or more thermal conductivity microdetectors are integral with one or more microchip bodies detachably mounted on the substrate, each of the one or more microchip bodies comprising one or more thermal conductivity microdetectors.

10. The gas chromatograph of claim 9 wherein the microdetector array further comprises
    four or more pairs of passages formed in the substrate for fluid communication with the four or more thermal conductivity microdetectors, respectively, each pair of passages comprising a first inlet passage for fluid communication with the inlet port of one of the thermal conductivity microdetectors, and a second outlet passage for fluid communication with the outlet port of the one of the thermal conductivity microdetectors, and
    one or more releasable seals situated between the substrate and the one or more microchip bodies.

11. The gas chromatograph of claim 10 wherein the one or more releasable seals comprises four or more pairs of o-rings for releasably sealing the inlet passages and outlet passages of the substrate with the corresponding inlet ports and outlet ports of the thermal conductivity microdetectors, respectively.

12. The gas chromatograph of claim 10 wherein the one or more releasable seals comprises one or more gaskets for releasably sealing the inlet passages and outlet passages of the substrate with the corresponding inlet ports and outlet ports of the thermal conductivity microdetectors, respectively.

13. The gas chromatograph of claim 1 wherein the each of the four or more thermal conductivity microdetectors further comprise first and second electrical contacts for electrical communication with an integral or an external signal-processing circuit, a first conductive path between the first electrical contact and a first end of the thin-film detection filament, and a second conductive path between the second electrical contact and a second end of the thin-film detection filament.

14. The gas chromatograph of claim 1 wherein the microdetector array further comprises at least one reference thermal conductivity microdetector, the at least one reference thermal conductivity microdetector having an inlet port in fluid communication with a reference gas source for receiving a reference gas, a detection cavity, a thin-film detection filament within the detection cavity for detecting the reference gas, and an outlet port for discharging the detected reference gas, the ratio of the number of gaseous sample thermal conductivity microdetectors to the number of reference thermal conductivity microdetector(s) being at least 2:1.

15. The gas chromatograph of claim 1 wherein the four or more thermal conductivity microdetectors are arranged to have a planar density of at least about 1 thermal conductivity microdetector per 10 $cm^2$.

16. The gas chromatograph of claim 1 wherein the four or more thermal conductivity microdetectors comprise six or more thermal conductivity microdetectors.

17. The gas chromatograph of claim 1 wherein the four or more thermal conductivity microdetectors comprise six or more thermal conductivity microdetectors arranged to have a planar density of at least about 1 thermal conductivity microdetector per 1 $cm^2$.

18. The gas chromatograph of claim 1 wherein the volume of the detection cavity of each of the four or more thermal conductivity microdetectors ranges from about 1 $\mu l$ to about 500 $\mu l$.

19. A gas chromatograph for simultaneous analysis of six or more fluid samples, the gas chromatograph comprising
    six or more gas chromatography columns, each of the six or more gas chromatography columns comprising an inlet for receiving a gaseous mobile phase that includes a gaseous sample, a separation media effective for separating at least one component of the sample from other components thereof, and an outlet for discharging the mobile phase and the separated sample, and a microdetector array comprising six or more sample thermal conductivity microdetectors and at least one reference thermal conductivity microdetector, each of the sample and reference thermal conductivity microdetectors being detachably mounted on a substrate with a planar density of at least about 1 thermal conductivity detector per 1 cm$^2$, the ratio of sample detectors to reference detector(s) being at least 2:1, each of the six or more sample thermal conductivity microdetectors having an inlet port in fluid communication with the outlet of one of the gas chromatography columns for receiving a separated sample, a detection cavity having a volume ranging from about 1 ml to about 500 ml for detecting at least one component of the separated sample, a thin-film detection filament within the detection cavity, the thin-film detection filament having a temperature-dependent resistance, an outlet port for discharging the sample, a first conductive path between the a first end of the thin-film detection filament and a first electrical contact, and a second conductive path between a second end of the thin-film detection filament and a second electrical contact, the first and second electrical contacts being adapted for electrical communication with one or more integral or external signal-processing circuits, the at least one reference thermal conductivity microdetector having an inlet port in fluid communication with a reference gas source for receiving a reference gas, a detection cavity comprising a thin-film detection filament within the detection cavity for detecting the reference gas, and an outlet port for discharging the detected reference gas, the six or more sample thermal conductivity detectors each having a thermal coefficient of resistance that varies less than about 10% between the six or more thermal conductivity detectors.

20. The gas chromatograph of claim 19 wherein the six or more sample thermal conductivity microdetectors are integral with one or more microchip bodies, each of the one or more microchip bodies comprising one or more thermal conductivity microdetectors, the microchip bodies being detachably mounted on a first mounting surface of the substrate, the first and second electrical contacts being situated on a first exposed surface of the microchip bodies, the first exposed surface of the microchip bodies being substantially parallel to a second mounting surface of the microchip bodies, the inlet port and the outlet port of the sample thermal conductivity microdetectors being substantially normal to the second mounting surface of the microchip bodies, the microdetector array further comprising six or more pairs of passages formed in the substrate for fluid communication with the six or more thermal conductivity microdetectors, respectively, each pair of passages comprising a first inlet passage for fluid communication with the inlet port of one of the thermal conductivity microdetectors, and a second outlet passage for fluid communication with the outlet port of one of the thermal conductivity microdetectors, one or more releasable seals situated between the first mounting surface of the substrate and the second mounting surface of the one or more microchip bodies, one or more signal processing circuits for measuring the temperature-dependent resistance of each of the thin-film detection filaments, and an array of electrical contact pins adapted to contact the electrical contacts at the first exposed surface of the one or more microchip bodies for providing electrical communication between the one or more signal processing circuits and the first and second electrical contacts of the six or more thermal conductivity microdetectors.

21. The gas chromatograph of claim 1 further comprising a parallel injector, the parallel injector comprising one or more injection valves adapted to substantially simultaneous inject four or more gaseous samples into the respective mobile phase of the four or more gas chromatography columns.

22. The gas chromatograph of claim 21 further comprising a parallel vaporizer, the parallel vaporizer comprising four or more injection ports for receiving four or more liquid samples, respectively, and four or more vaporization chambers for substantially simultaneously vaporizing four or more liquid samples to form the four or more gaseous samples.

23. The gas chromatograph of claim 22 wherein the parallel vaporizer is integral with the parallel injector.

24. The gas chromatograph of claims 1 or 10 wherein the four or more gas chromatography columns are capillary gas chromatography columns.

25. The gas chromatograph of claims 1 or 10 wherein the four or more gas chromatography columns are microfluidic channels comprising the separation medium.

26. The gas chromatograph of claim 1 wherein the gas chromatograph comprises eight or more gas chromatography columns in a heated environment, the heated environment comprising a convection zone for directed flow of a fluid in a substantially uniform direction past the eight or more gas chromatography columns.

27. The gas chromatograph of claim 1 wherein the detection cavity comprises two or more thin-film detection filaments.

28. The gas chromatograph of claims 1 or 10 in an apparatus further comprising a parallel flow reactor having four or more reaction vessels, each of the four or more reaction vessels comprising an inlet for feeding reactants into the reaction vessel, a reaction zone for effecting a chemical reaction, and an outlet for discharging reaction products and unreacted reactants, if any, the outlets of the four or more reaction vessels being in at least sampling fluid communication with the inlets of the four or more gas chromatography columns, respectively.

29. A microdetector array comprising four or more thermal conductivity microdetectors detachably mounted on a substrate with a planar density of at least about 1 thermal conductivity microdetector per 10 cm$^2$, each of said thermal conductivity microdetectors comprising a detection cavity having a volume of not more than about 500 µl, an inlet port for admitting a fluid sample into the detection cavity, a thin-film detection filament within the detection cavity, the thin-film detection filament having a temperature-dependent resistance, an outlet port for discharging a fluid sample from the detection cavity, first and second electrical contacts for electrical communication with a signal-processing circuit, a first conductive path between the first electrical contact and a first end of the thin-film detection filament, and a second conductive path between the second electrical contact and a second end of the thin-film detection filament.

30. The array of claim 29 wherein the four or more thermal conductivity microdetectors each have a thermal coefficient of resistance that varies less than about 10% between the four or more thermal conductivity microdetectors.

31. The array of claim 29 wherein the thin-film detection filament of each of the four or more thermal conductivity microdetectors has a resistance that varies less than about 25% between the four or more thermal conductivity microdetectors.

32. The array of claim 29 wherein the four or more thermal conductivity microdetectors are integral with one or more microchip bodies detachably mounted on the substrate, each of the one or more microchip bodies comprising one or more microdetectors.

33. The array of claim 32 wherein the microdetector array further comprises four or more pairs of passages formed in the substrate for fluid communication with the four or more thermal conductivity microdetectors, respectively, each pair of passages comprising a first inlet passage for fluid communication with the inlet port of one of the thermal conductivity microdetectors, and a second outlet passage for fluid communication with the outlet port of the one of the thermal conductivity microdetectors, and one or more releasable seals situated between the substrate and four or more thermal conductivity microdetectors.

34. The array of claim 32 wherein the first and second electrical contacts are situated on a first exposed surface of the one or more microchip bodies, and the inlet port and the outlet port of the thermal conductivity microdetectors are substantially normal to an opposing second surface of the microchip bodies.

35. The array of claim 29 wherein the four or more thermal conductivity microdetectors are arranged to have a planar density of at least about 2 thermal conductivity microdetector per 1 cm$^2$.

36. The array of claim 29 wherein the volume of the detection cavity of each of the four or more thermal conductivity microdetectors ranges from about 1 to about 500 $\mu$l.

37. A method for parallel analysis of four or more fluid samples by gas chromatography, the method comprising injecting four or more gaseous samples into respective mobile phases of four or more gas chromatography columns, contacting the four or more gaseous samples with separation media in the respective gas chromatography columns to separate at least one analyte from other constituents of the gaseous samples, and detecting the four or more separated analytes with a microdetector array comprising four or more microfabricated, thin-film thermal conductivity microdetectors detachably mounted on said microdetector array.

38. A method for using the gas chromatograph of claim 1 or 10 for parallel analysis of four or more fluid samples by gas chromatography, the method comprising injecting four or more gaseous samples into respective mobile phases of the four or more gas chromatography columns, contacting the four or more gaseous samples with separation media in the respective gas chromatography columns to separate at least one analyte from other constituents of the gaseous samples, and detecting the four or more separated analytes with the microdetector array.

39. A method for using the gas chromatograph of claims 1 or 10 for parallel analysis of four or more fluid samples by gas chromatography, the method comprising injecting four or more gaseous samples into respective mobile phases of the four or more gas chromatography columns, contacting the four or more gaseous samples with separation media in the respective gas chromatography columns to separate at least one analyte from other constituents of the gaseous samples, and detecting the four or more separated analytes with the microdetector array.

40. The method of claim 37 wherein the four or more fluid samples are four or more liquid samples, the method further comprising injecting the four or more liquid samples into the injection ports of the parallel vaporizer, and substantially simultaneously vaporizing the four or more liquid samples to form four or more gaseous samples.

41. The method of claim 37 wherein the four or more fluid samples are four or more gaseous samples discharged from a parallel flow reactor comprising four or more reaction channels.

42. A method as set forth in claim 39 further comprising contacting the four or more separated analytes directly with a corresponding thin-film detection filament of the microdetector array.

43. A gas chromatograph having eight or more analysis channels for simultaneous analysis of eight or more fluid samples, the gas chromatograph comprising eight or more gas chromatography columns residing in a heated environment, each of the eight or more gas chromatography columns comprising an inlet for receiving a gaseous mobile phase that includes a gaseous sample, a separation media effective for separating at least one component of the sample from other components thereof, and an outlet for discharging the separated sample, the heated environment comprising a forced convection zone for directed flow of a fluid in a substantially uniform direction past the eight or more gas chromatography columns, and a microdetector array comprising eight or more thermal conductivity microdetectors detachably mounted on said microdetector array, the eight or more thermal conductivity microdetectors each having an inlet port in fluid communication with the outlet of one or more of the gas chromatography columns for receiving a separated sample, a detection cavity for detecting at least one component of the separated sample, and an outlet port for discharging the sample.

44. The gas chromatograph of claim 43 wherein the convection zone is defined by a zone of substantially uniformly directed turbulent fluid flow between two or more convection fans.

45. The gas chromatograph of claim 43 wherein the convection zone is defined by a zone of substantially uniformly directed turbulent fluid flow created by two or more convection fans on opposing sides of the eight or more gas chromatography columns.

46. The gas chromatograph of claim 45 wherein the convection zone is further defined by a chimney adapted to direct the fluid flow within the chimney from one or more convection fans on first side of the eight or more gas chromatography columns to one or more opposing convection fans on an opposing second side of the eight or more gas chromatography columns, with the gas chromatography columns being internal or external to the chimney.

47. The gas chromatograph of claim 46 wherein a first convection fan is a radial convection fan and a second convection fan is an axial convection fan.

48. The gas chromatograph of claim 43 comprising sixteen or more gas chromatography columns in the heated environment.

49. The gas chromatograph of claim 19 wherein the six or more gas chromatography columns are capillary gas chromatography columns.

50. The gas chromatograph of claim 19 wherein the six or more gas chromatography columns are microfluidic channels comprising the separation medium.

51. A method for using the gas chromatograph of claim 32 for parallel analysis of six or more fluid samples by gas chromatography, the method comprising injecting six or more gaseous samples into respective mobile phases of the six or more gas chromatography columns, contacting the six or more gaseous samples with separation media in the respective gas chromatography columns to separate at least one analyte from other constituents of the gaseous samples, and detecting the six or more separated analytes with the microdetector array.

* * * * *

UNITED STATES PATENT AND TRADEMARK OFFICE
CERTIFICATE OF CORRECTION

PATENT NO. : 6,701,774 B2
DATED : March 9, 2004
INVENTOR(S) : Srinivasan et al.

It is certified that error appears in the above-identified patent and that said Letters Patent is hereby corrected as shown below:

Title page,
Item [75], Inventors, change to read:

-- Ravi Srinivasan, Mountain View, CA (US);
Daniel Meron Pinkas, Kensington, CA (US);
Shenheng Guan, Palo Alto, CA (US); Michael Myslovaty, San Jose, CA (US); Mikhail Spitkovsky, Sunnyvale, CA (US); James R. Engstrom, Ithaca, NY (US); H. Sam Bergh, San Francisco, CA (US)

Column 39,
Line 42, delete "2" and insert --1 --
Line 46, insert -- µl -- after "1"

Signed and Sealed this

Fifth Day of October, 2004

JON W. DUDAS
*Director of the United States Patent and Trademark Office*